United States Patent
Rohl et al.

(10) Patent No.: US 11,020,228 B2
(45) Date of Patent: Jun. 1, 2021

(54) ANCHOR DELIVERY SYSTEM AND METHODS FOR VALVE REPAIR

(71) Applicants: Boston Scientific Scimed, Inc., Maple Grove, MN (US); MAYO FOUNDATION FOR MEDICAL EDUCATION AND RESEARCH, Rochester, MN (US)

(72) Inventors: James P. Rohl, Prescott, WI (US); Joel T. Eggert, Plymouth, MN (US); Katherine L. Baldwin, Minneapolis, MN (US); Craig M. Wilson, Minneapolis, MN (US); Lance A. Freeseman, Greenfield, MN (US); James K. Cawthra, Jr., Ramsey, MN (US); Dennis B. Werner, Big Lake, MN (US); Daniel Shuey, Pine City, MN (US); Jonathan P. Fettig, Blaine, MN (US); Todd College, Little Canada, MN (US); Gurpreet S. Sandhu, Rochester, MN (US); Joseph A. Dearani, Rochester, MN (US); Aaron Abbott, Columbia Heights, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 167 days.

(21) Appl. No.: 16/104,085

(22) Filed: Aug. 16, 2018

(65) Prior Publication Data
US 2019/0053903 A1 Feb. 21, 2019

Related U.S. Application Data

(60) Provisional application No. 62/546,766, filed on Aug. 17, 2017.

(51) Int. Cl.
*A61F 2/24* (2006.01)
*A61B 17/122* (2006.01)
(Continued)

(52) U.S. Cl.
CPC ........ *A61F 2/2454* (2013.01); *A61B 17/1227* (2013.01); *A61B 17/1285* (2013.01);
(Continued)

(58) Field of Classification Search
CPC ... A61B 17/1285; A61B 17/128; A61B 17/29; A61B 2017/0409; A61B 17/10;
(Continued)

(56) References Cited

U.S. PATENT DOCUMENTS

| 5,634,936 A | 6/1997 | Linden et al. |
| 5,853,422 A | 12/1998 | Huebsch et al. |

(Continued)

FOREIGN PATENT DOCUMENTS

| EP | 0809469 A1 | 12/1997 |
| EP | 2829240 A1 | 1/2015 |

(Continued)

OTHER PUBLICATIONS

International Search Report and Written Opinion for application No. PCT/US2018/046822, dated Mar. 19, 2019, 24 pages.

*Primary Examiner* — Katherine M Shi
(74) *Attorney, Agent, or Firm* — Kacvinsky Daisak Bluni PLLC

(57) ABSTRACT

Anchor delivery systems and methods for repairing a valve inside a body, such as a heart valve, may include a delivery catheter having a distal end comprised of two or more rotatably coupled knuckles. An anchor delivery mechanism is disposed distally of the two or more knuckles, and includes a first pincer arm having a distal end and a proximal end rotatably coupled to a distal end of the anchor delivery (Continued)

mechanism at a first connection point, and a second pincer arm having a distal end and a proximal end rotatably coupled to the distal end of the anchor delivery mechanism at a second connection point opposite the first connection point. In a closed position, the distal ends of the first and second pincer arms are positioned together. In an open position, the distal ends of the first and second pincer arms are rotated apart from each other.

20 Claims, 51 Drawing Sheets

(51) Int. Cl.
*A61B 17/128* (2006.01)
*A61B 90/00* (2016.01)
*A61B 34/20* (2016.01)
*A61B 17/00* (2006.01)
*A61B 90/30* (2016.01)
*A61B 17/29* (2006.01)

(52) U.S. Cl.
CPC .............. *A61B 34/20* (2016.02); *A61B 90/37* (2016.02); *A61F 2/2442* (2013.01); *A61F 2/2466* (2013.01); *A61B 2017/00243* (2013.01); *A61B 2017/00292* (2013.01); *A61B 2017/00314* (2013.01); *A61B 2017/00323* (2013.01); *A61B 2017/00327* (2013.01); *A61B 2017/00331* (2013.01); *A61B 2017/00336* (2013.01); *A61B 2017/00349* (2013.01); *A61B 2017/00398* (2013.01); *A61B 2017/00477* (2013.01); *A61B 2017/00783* (2013.01); *A61B 2017/00867* (2013.01); *A61B 2017/2908* (2013.01); *A61B 2017/2927* (2013.01); *A61B 2034/2055* (2016.02); *A61B 2034/2057* (2016.02); *A61B 2034/2063* (2016.02); *A61B 2090/309* (2016.02); *A61B 2090/3925* (2016.02); *A61B 2217/007* (2013.01); *A61F 2/2445* (2013.01); *A61F 2210/0014* (2013.01); *A61F 2220/0016* (2013.01); *A61F 2220/0025* (2013.01); *A61F 2220/0058* (2013.01); *A61F 2230/0006* (2013.01); *A61F 2230/0063* (2013.01)

(58) Field of Classification Search
CPC ........ A61B 2017/2927; A61B 17/0469; A61B 17/0218; A61B 2017/06052; A61B 17/08; A61B 2017/2929; A61B 18/1445; A61B 2017/00243; A61B 2017/00292; A61B 2017/00314; A61B 2017/00323; A61B 2017/00327; A61B 2017/00349; A61B 2017/2908; A61B 2034/2055; A61B 2034/2057; A61B 2034/2063; A61B 2090/3925; A61B 34/20; A61B 90/37; A61F 2/2427; A61F 2/2445; A61F 2/2466; A61F 2220/0016; A61F 2/2454

See application file for complete search history.

(56) References Cited

U.S. PATENT DOCUMENTS

| | | | |
|---|---|---|---|
| 6,024,756 A | 2/2000 | Huebsch et al. | |
| 6,117,159 A | 9/2000 | Huebsch et al. | |
| 6,270,515 B1 | 8/2001 | Linden et al. | |
| 6,312,446 B1 | 11/2001 | Huebsch et al. | |
| 7,689,320 B2 | 3/2010 | Prisco et al. | |
| 8,357,193 B2 | 1/2013 | Phan et al. | |
| 8,454,632 B2 | 6/2013 | Binmoeller et al. | |
| 8,961,594 B2 | 2/2015 | Maisano et al. | |
| 8,961,596 B2 | 2/2015 | Maisano et al. | |
| 9,044,246 B2 | 6/2015 | Goldfarb et al. | |
| 9,241,702 B2 | 1/2016 | Maisano et al. | |
| 2002/0087148 A1 | 7/2002 | Brock et al. | |
| 2003/0055442 A1 | 3/2003 | Laufer et al. | |
| 2003/0199974 A1 | 10/2003 | Lee et al. | |
| 2004/0193186 A1* | 9/2004 | Kortenbach | A61B 17/1285 606/142 |
| 2005/0192633 A1* | 9/2005 | Montpetit | A61B 17/0469 606/232 |
| 2005/0250986 A1 | 11/2005 | Rothe et al. | |
| 2005/0250988 A1 | 11/2005 | Ewers et al. | |
| 2005/0251177 A1* | 11/2005 | Saadat | A61F 5/0086 606/153 |
| 2007/0066863 A1* | 3/2007 | Rafiee | A61B 17/0401 600/37 |
| 2007/0073337 A1 | 3/2007 | Abbott et al. | |
| 2008/0308607 A1* | 12/2008 | Timm | A61B 17/07207 227/176.1 |
| 2010/0113873 A1* | 5/2010 | Suzuki | A61B 1/00183 600/106 |
| 2010/0217283 A1 | 8/2010 | St Goar et al. | |
| 2012/0143173 A1* | 6/2012 | Steege | A61B 17/29 606/1 |
| 2012/0296349 A1 | 11/2012 | Smith et al. | |
| 2014/0194898 A1 | 7/2014 | Kirschenman et al. | |
| 2015/0045879 A1 | 2/2015 | Longoria et al. | |
| 2016/0213228 A1* | 7/2016 | Rohl | A61B 8/12 |

FOREIGN PATENT DOCUMENTS

| | | |
|---|---|---|
| WO | 2006039199 A2 | 4/2006 |
| WO | 2007009021 A2 | 1/2007 |
| WO | 2007070753 A2 | 6/2007 |
| WO | 2008045333 A2 | 4/2008 |
| WO | 2017098273 A1 | 6/2017 |
| WO | 2017106720 A1 | 6/2017 |

* cited by examiner

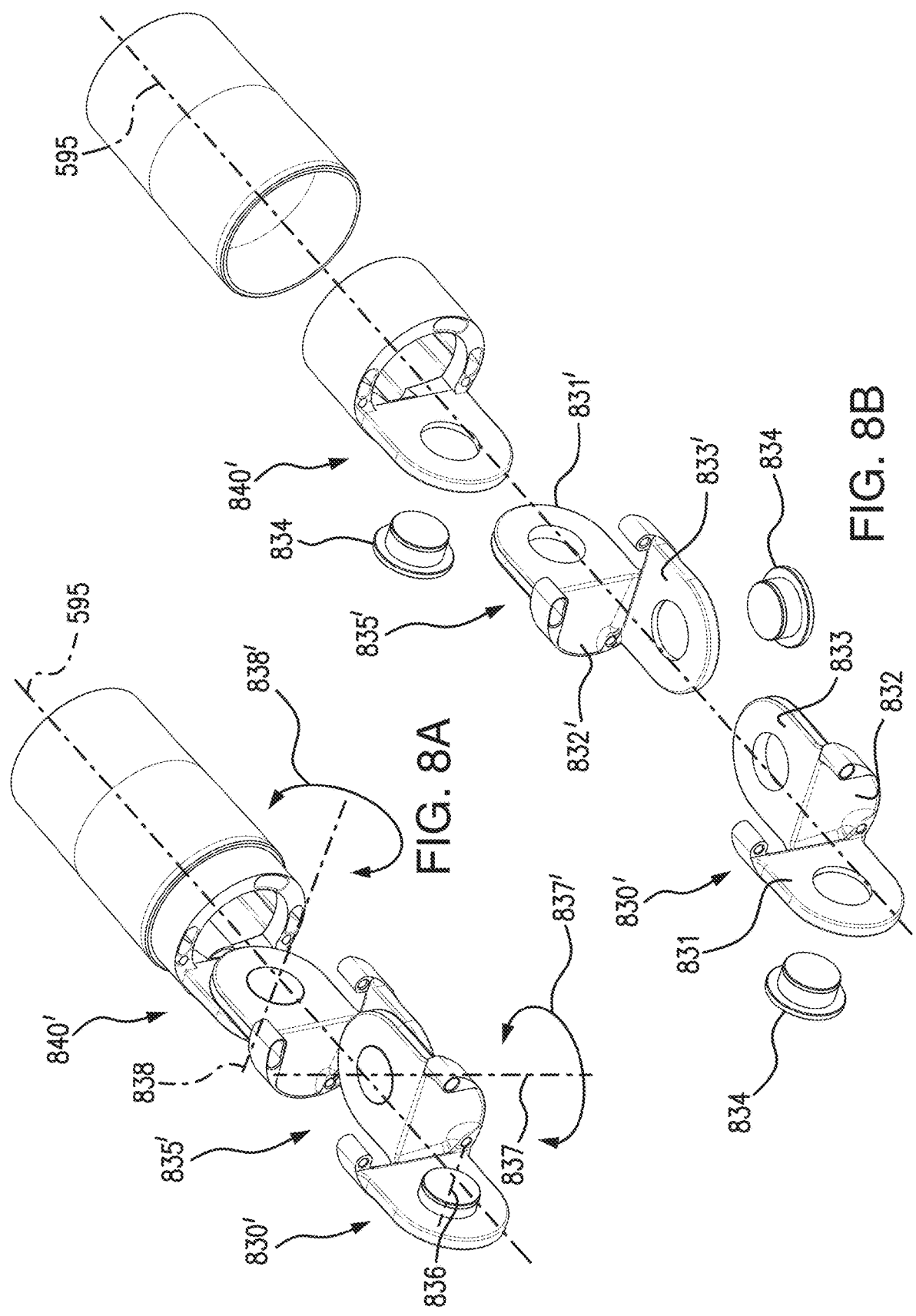

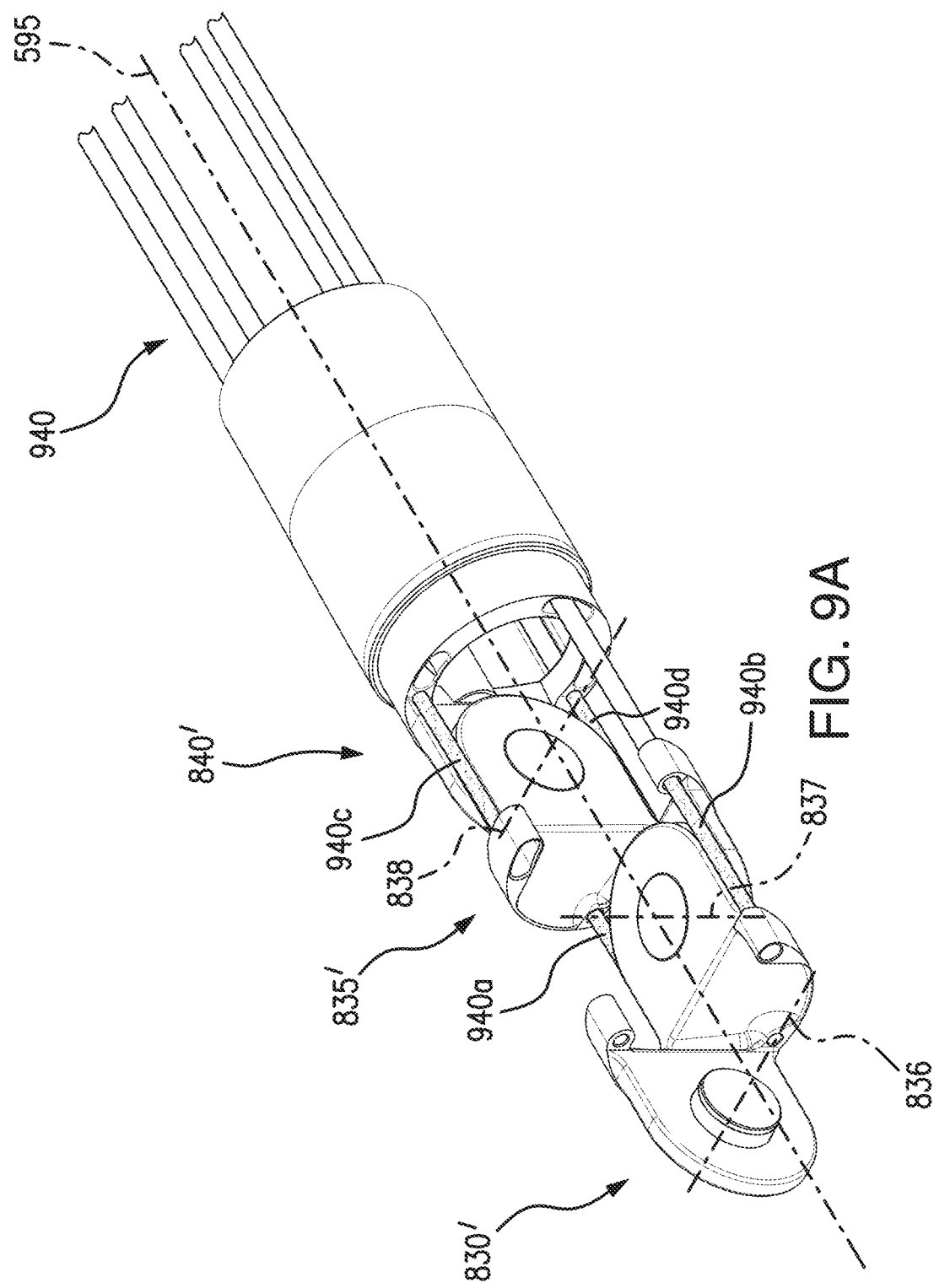

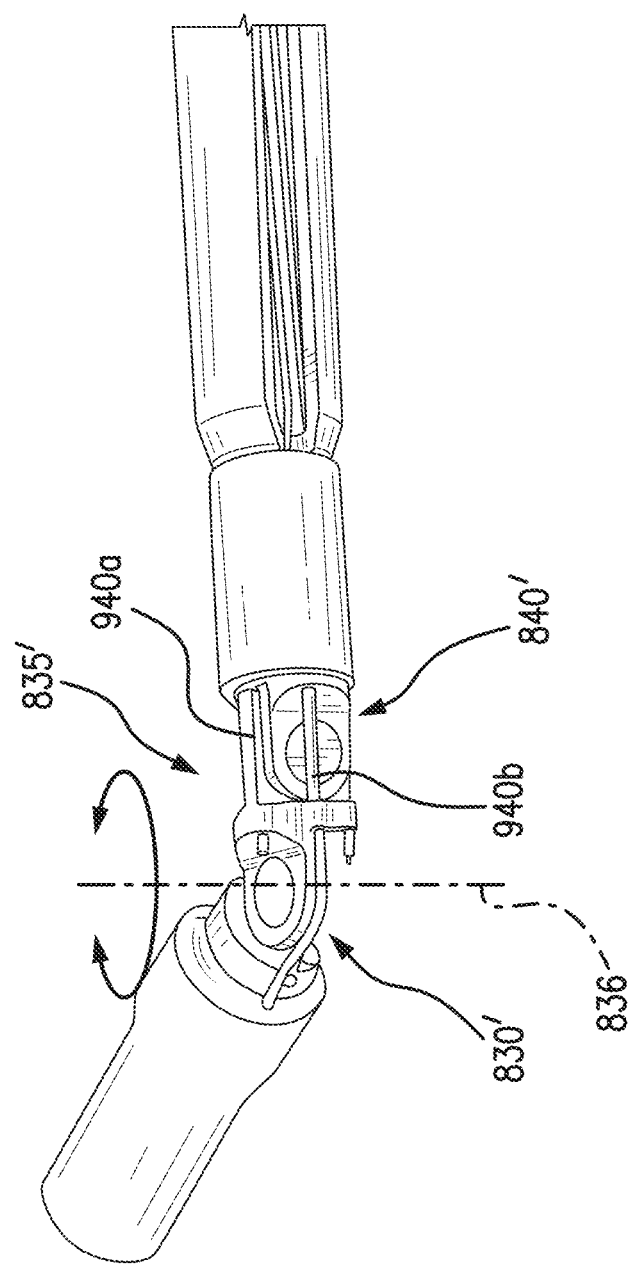

|  | Actuation | Motion | Travel | Load |
|---|---|---|---|---|
| 580a | 1st pincer arm 515a | ⟷ | 1 cm | 1 lb |
| 580b | 2nd pincer arm 515b | ⟷ | 1 cm | 1 lb |
| 935 | 3rd knuckle 840 | ↺ | 1 cm | 1 lb |
| 930 | 2nd knuckle 835 | ↺ | 1 cm | 1 lb |
| 925 | 1st knuckle 830 | ↺ | 1 cm | 1 lb |
| 915 | Helix 540 | ⟷ | 2 cm | 1 lb |
| 920 | Helix 540 | ↷ | 6 turns | .5 in/lbs |
| 910 | Delivery catheter 500 | ⟷ | 150 cm | 10 lbs |
| 905 | Delivery catheter 500 | ↷ | 1 turn | 10 in/lbs |

FIG. 10

ANCHOR DELIVERY SYSTEM AND METHODS FOR VALVE REPAIR

CROSS-REFERENCE TO RELATED APPLICATIONS

This application is a non-provisional application of, and claims the benefit of priority to, U.S. Provisional Application Ser. No. 62/546,766, filed Aug. 17, 2017, entitled "Anchor Delivery System and Methods for Valve Repair," the entirety of which application is expressly incorporated by reference herein.

FIELD

The present disclosure relates generally to systems and methods for valve repair, more particularly, an anchor delivery system for annular reduction of an atrial valve, such as the mitral and tricuspid valves.

BACKGROUND

A valve in the body may have damaged or weakened annular tissue that requires repair to help improve the function of the valve. As an example, atrioventricular valves of the heart include a mitral, or bicuspid, valve, and a tricuspid valve. For example, FIGS. 1A and 1B illustrate a tricuspid valve in various enlarged states, e.g., FIG. 1B shows a tricuspid valve opening greater than a tricuspid valve illustrated in FIG. 1A. The mitral valve 200, 205 is a dual flap valve having an anterior leaflet 220 and a posterior leaflet 225 surrounded by annular tissue, e.g., an annulus 210, 215 disposed between the left atrium and the left ventricle of the heart, and the tricuspid valve 100, 105 has three leaflets (e.g., anterior 120, posterior 125, and septal 130) surrounded by an annulus 110, 115 disposed between the right atrium and the right ventricle of the heart. FIG. 2A shows a mitral valve 200 in a closed, e.g., a normal, position, and FIG. 2B shows a mitral valve 205 in an enlarged position. When the mitral and tricuspid valves function properly, the valves act to prevent backflow of blood from the ventricles to the atria during systole. When a patient has a disorder of the heart, mitral regurgitation (MR) and/or tricuspid regurgitation (TR) may occur where blood leaks backward through the valve when the respective ventricle contracts. For example, an enlarged ventricle may affect the respective valve in that it will not fully close, allowing leakage to occur. This mitral annular dilation and/or tricuspid annular dilation results in mitral regurgitation and/or tricuspid regurgitation.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, an anchor delivery system for repairing a heart valve may include an anchor delivery mechanism disposed at a distal end of a delivery catheter. The anchor delivery mechanism may include a first pincer arm having a distal end and a proximal end rotatably coupled to a distal end of the anchor delivery mechanism at a first connection point, a second pincer arm having a distal end and a proximal end rotatably coupled to the distal end of the anchor delivery mechanism at a second connection point opposite the first connection point. In a closed position, the distal ends of the first and second pincer arms may be positioned together toward a center of the anchor delivery mechanism. In an open position, the distal ends of the first and second pincer arms may be rotated apart from each other.

According to an exemplary embodiment of the present disclosure, an anchor delivery system for repairing a valve in a body of a patient may include a delivery catheter having a distal end comprised of two or more rotatably coupled knuckles, wherein an axis of rotation of a first knuckle is substantially perpendicular to an axis of rotation of a second knuckle such that the two or more knuckles form an articulable distal end of the delivery catheter, and an anchor delivery mechanism disposed distally of the two or more knuckles. The anchor delivery mechanism may include a first pincer arm having a distal end and a proximal end rotatably coupled to a distal end of the anchor delivery mechanism at a first connection point, and a second pincer arm having a distal end and a proximal end rotatably coupled to the distal end of the anchor delivery mechanism at a second connection point opposite the first connection point. In a closed position, the distal ends of the first and second pincer arms may be positioned together toward a center of the anchor delivery mechanism. In an open position, the distal ends of the first and second pincer arms may be rotated apart from each other.

According to exemplary embodiment of the present disclosure, a method for delivering an anchor by an anchor delivery system for repairing a valve in a body of a patient may include inspecting tissue of the valve by a distal end of a delivery catheter, the distal end comprised of two or more rotatably coupled knuckles, and a plurality of cables operable by a respective motor to form an articulable distal end of the delivery catheter; opening first and second pincer arms of an anchor delivery mechanism disposed distally of the two or more knuckles, the first pincer arm having a distal end and a proximal end rotatably coupled to a distal end of the anchor delivery mechanism at a first connection point, and the second pincer arm having a distal end and a proximal end rotatably coupled to the distal end of the anchor delivery mechanism at a second connection point opposite the first connection point; rotating the first and second pincer arms into a closed position to pierce the tissue and position the distal ends of the first and second pincer arms together toward a center of the anchor delivery mechanism; delivering an anchor to the first and second pincer arms; opening the first and second pincer arms to retract from the tissue, the delivered anchor remaining in the tissue; and inserting additional anchors around the tissue as necessary to repair the valve.

In various of the foregoing and other embodiments of the present disclosure, the systems and methods may include that the distal ends of the first and second pincer arms may be configured to pierce a tissue of the heart valve. An anchor may be deliverable to the first and second pincer arms when the first and second pincer arms are in the closed position. The first and second pincer arms may be retractable to the open position such that the anchor remains in the tissue. The anchor may be configured to reduce a perimeter of the heart valve. The first and second pincer arms may be formed of at least one of a rigid material and a superelastic material. The first pincer arm may be formed of an at least partially open tube and the second pincer arm may have an open curvature, such that the one or more anchors may be towable through the first and the second pincer arms. The anchor delivery mechanism may be disposed distally of the distal end of the delivery catheter and rotatably coupled to a distal end of a first knuckle. The anchor delivery system may further comprise a second knuckle having a distal end rotatably coupled to a proximal end of the first knuckle. The anchor delivery system may further comprise a third knuckle having a distal end rotatably coupled to a proximal end of the second knuckle. A proximal end of the knuckle may be coupled to the distal end of the delivery catheter. The distal end of the anchor delivery mechanism may include any of a five degree-of-freedom (DOF) navigation sensor, a six DOF navigation sensor, a camera, a light, and an ultrasonic sensor. The anchor delivery system may include a plurality of cables each connected at a distal end to a respective first, second, and third knuckle. The cables may each be operable by a motor connected at a proximal end of the cables. The distal end of the delivery catheter may be movable by flexing joints between the first, second, or third knuckle, or combinations thereof, and may minimize tension on the respectively connected cable. The anchor delivery system may further comprise a fixation device disposed at the distal end of the anchor delivery mechanism, and may be insertable into a valve to anchor the anchor delivery mechanism. The valve may be a heart valve.

In various of the foregoing and other embodiments of the present disclosure, the systems and methods may include that the anchor delivery system may further comprise one or more anchors deliverable to tissue of the valve by the first and second pincer arms. The first and second pincer arms may be configured to pierce the tissue by the distal ends of the first and second pincer arms to the closed position. One or more anchors may be deliverable through a first pincer arm and a second pincer arm. The first and second pincers arms may be retractable to the open position such that the one or more anchors remain in the tissue. The one or more anchors may be configured to reduce a perimeter of the valve. The distal end of the anchor delivery mechanism may include a weeping saline balloon. The one or more anchors may be deliverable to the first and second pincer arms by at least one of a stylet and a suture. The anchor delivery system may further comprise a fixation device disposed at the distal end of the anchor delivery mechanism, and insertable into tissue to anchor the delivery catheter to the tissue. The valve may be a mitral or tricuspid valve and the tissue of the mitral or tricuspid valve may be annulus tissue.

In various of the foregoing and other embodiments of the present disclosure, the systems and methods may include that upon opening the first and second pincer arms for piercing the tissue, the delivery catheter may be translatable such that the first and second pincer arms pierce into the tissue at a repeatable tissue depth. The anchor may be delivered by towing the anchor by at least one of a stylet and a suture. A stylet may tow the anchor through the first and the second pincer arms such that a portion of the anchor may extend out of the tissue. In each of the foregoing and other embodiments of the present disclosure, the systems and methods may further comprise inserting a fixation device in the tissue to anchor the delivery catheter before delivering the anchor, and disengaging the delivery catheter from the tissue by retracting the fixation device after delivering the anchor. An axis of rotation of a first knuckle may be substantially perpendicular to an axis of rotation of a second knuckle. The method may further include expanding a first bulb of an anchor by retracting an inner coil extended through the stylet and the anchor, rotating the second pincer arm out of the tissue, retracting the inner coil from a remaining portion of the anchor such that a second bulb of the anchor expands to plicate the tissue, and rotating the first pincer arm out of the tissue.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 8A-8B illustrate an exemplary embodiment of knuckles of an anchor delivery device in accordance with the present disclosure;

FIGS. 9A-9D illustrate an exemplary embodiment of knuckles and a cable system of an anchor delivery device in accordance with the present disclosure;

FIG. 10 is a chart illustrating movement of an exemplary embodiment of the anchor delivery device of FIG. 9;

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

While emphasis and discussion is focused in the present disclosure on embodiments of a device, systems, and anchor configurations to reduce annular tissue around mitral and/or tricuspid valves, the breadth of the disclosure is intended to encompass such devices, systems, and methods to deliver various configurations of anchors for anchoring tissue to reduce and repair valves generally in various parts of a human or animal body. An annuloplasty ring or band may be placed around a valve and held in place by sutures. The annuloplasty ring or band may create one or more tissue plications, or folds in the annular tissue, to reduce the perimeter of the annulus and to induce leaflet coaptation. Existing repairs for mitral and tricuspid valves by sutures may be disadvantageous because the sutures may split or tear over time, requiring a patient to undergo further surgical repairs. Additionally, an improper band or ring size may increase the likelihood of tearing thereby requiring surgical repairs sooner than desired. When the annuloplasty ring or band dislodges, the valve may once again leak blood back into the respective atrium, causing the patient discomfort and weakness.

Figure 1A:
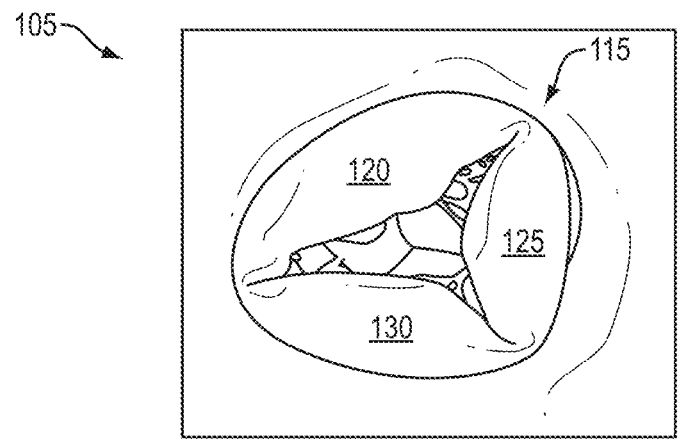
FIGS. 1A-1B illustrate a tricuspid valve in enlarged states.
Figure 1B:
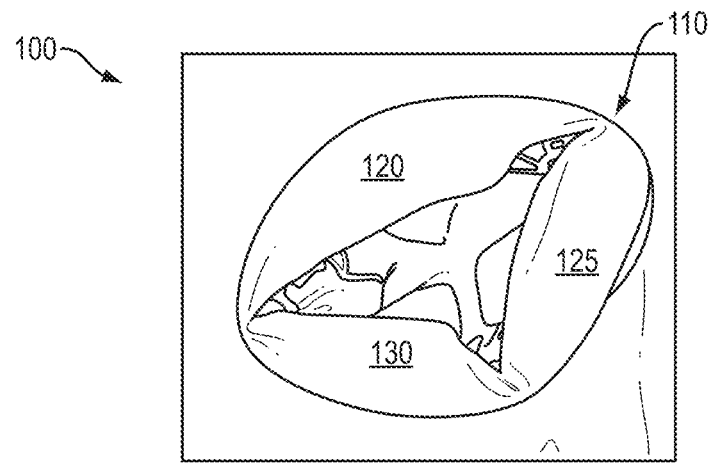
Figure 2A:
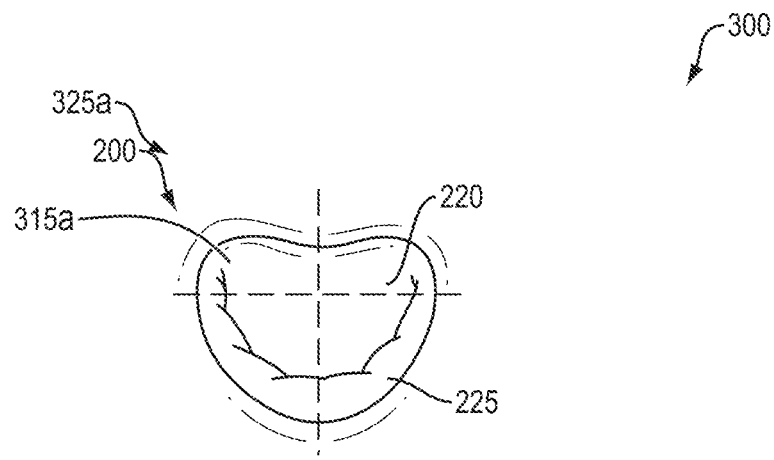
FIGS. 2A-2B illustrate a bicuspid valve in a closed state and an enlarged state.
Figure 2B:
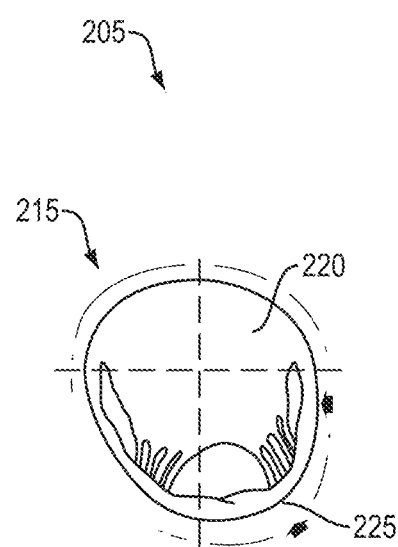
Figure 3A:
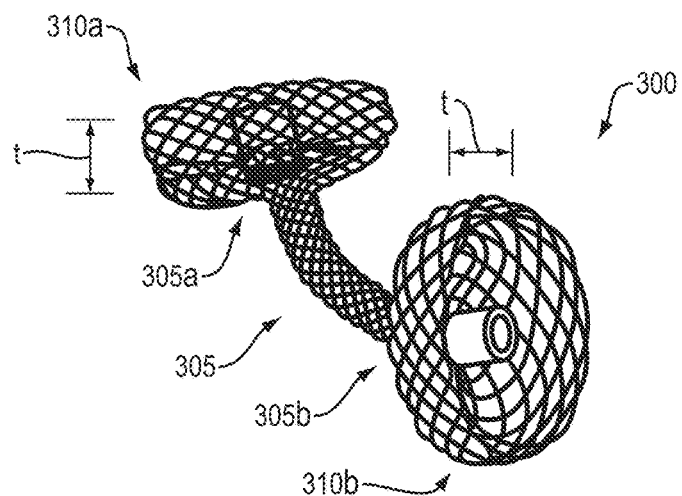
FIGS. 3A-3C illustrate an exemplary embodiment of an anchor in accordance with the present disclosure.
Figure 3B:
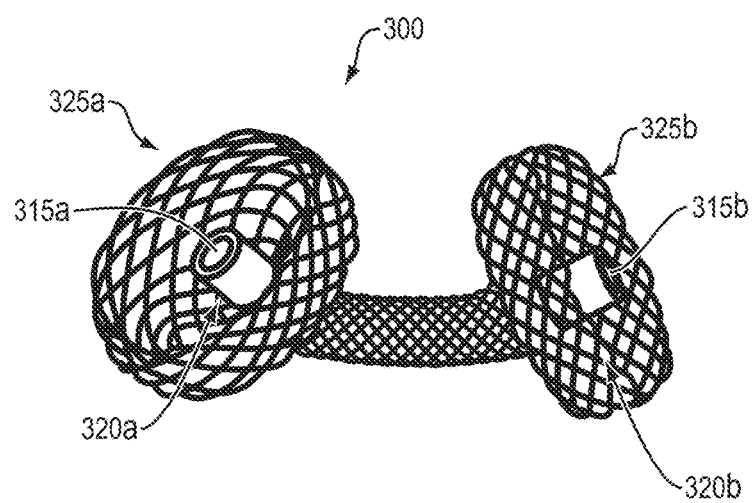
Figure 3C:
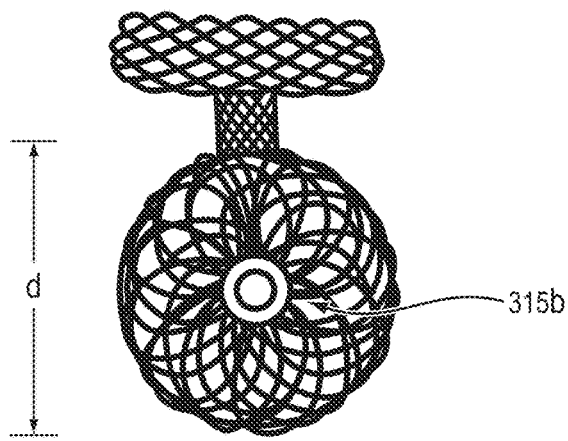

The systems and methods described herein are intended to overcome the disadvantages in existing valve repair devices and processes by delivering one or more anchors to the annular tissue around the valve, thereby allowing for a partial or full reduction so that the valve may close. Referring now to FIGS. 3A-3C, an exemplary embodiment of a mitral and/or tricuspid annular reduction anchor (MARA/TARA) 300 in accordance with the present disclosure is shown. In some embodiments, the anchor 300 may include a connector 305 having a first end 305a and a second end 305b opposite the first end 305a. For example, the connector 305 may be a tube. A first bulb, or disk 310a, may be disposed at the first end 305a and a second bulb, or disk 310b, may be disposed at the second end 305b. The first and second disks 310a, 310b may be substantially circular in shape having a diameter d, although the bulbs, or disks, may be any other shape, including but not limited to oval, square, polygonal, and the like. It is understood that bulbs or disks may be used interchangeably throughout. The first and second disks 310a, 310b may have the same diameter, or may have different diameters. As described below, the diameter of the first and second disk 310a, 310b should be large enough to spread the force of the anchor 300 to prevent tearing out of the annulus. The first and second disks 310a, 310b may have a thickness $t_a$ and $t_b$, where in some embodiments $t_a$ and $t_b$, may be equal to each other, and in other embodiments $t_a$ and $t_b$, may be different from each other. The thickness t may be thick enough to provide structural support to the first and second disk 310a, 310b to prevent the anchor 300 from tearing out of the annulus. In some embodiments, disk 310a, 310b may include a lip 325a, 325b (FIG. 3C).

The connector 305 may connect at a center 315a, 315b of the respective disk 310a, 310b, the connector 305 being a tube and having a smaller outer diameter than an outer diameter d of the first and second disks 310a, 310b. In some embodiments, the connector 305, first disk 310a, and the second disk 310b may be integrally formed, although in other embodiments the anchor 300 may be formed by coupling at least one of the connector 305, the first disk 310a, and the second disk 310b together. In some embodiments, a weld 320a, 320b may be disposed at the center 315a, 315b of the disk 310a, 310b at each end 305a, 305b of the connector 305. In some embodiments, the weld 320a, 320b may be a gathering or termination of respective ends of the first disk 310a and the second disk 310b. The weld 320a, 320b may extend a length from the respective first or second end 305a, 305b of the connector 305 in the center 315a, 315b of the disk 310a, 310b. For example, the weld 320a, 320b may extend the same thickness t as the respective first or second disk 310a, 310b, such that it does not extend beyond the lips 325a, 325b of the disk 310a, 310b. In other embodiments, the weld 320a, 320b may be disposed outward from the disk at the center 315a, 315b.

The anchor 300 may be formed of a flexible braided nitinol, to promote tissue growth in and around the anchors. In some embodiments, the anchor 300 may be electropolished. Promoting tissue growth may be advantageous as it may prevent the anchors from tearing out over time. Additionally, the annulus size may be fixed by the tissue growth. As will be described in detail below, the anchor 300 may be of a flexible material, e.g. a shape memory material, so that the anchor may be deliverable in a compressed state, and expanded or expandable or self-expanding to the formed shape described above. The components of the anchor 300, including but not limited to the connector 305, the first disk 310a, and the second disk 310b, may be formed of the same braided nitinol material. For example, the first disk 310a and the second disk 310b may be braided in a manner differently than the connector 305. The weld 320a, 320b may be formed of a metal material to provide structural support to the anchor 300. The weld 320a, 320b may be coupled to the anchor 300 by threading at least a portion of braided nitinol through an aperture of the weld 320a, 320b. The weld 320a, 320b may also be coupled to the anchor by adhesive or another bonding technique.

Additional exemplary embodiments of an anchor are illustrated in FIGS. 4A-4G. Anchor 400a shown in FIG. 4A may be similar to anchor 300 illustrated in FIGS. 3A-3C, including a connector 405, a first disk 410a disposed at a first end 405a of the connector 405, and a second disk 410b disposed at a second end 405b of the connector 405. The first disk 410a may have a first inward surface 875a, and the second disk 410b may have a second inward surface 875b, so that the first and second inward surfaces 875a, 875b face each other. The first and the second disks 410a, 410b may be sized the same and have a diameter $d_a$ and a thickness $t_a$, although it is understood that in some embodiments the first and second disks 410a, 410b may each have different diameters and/or thicknesses. The first and second disks 410a, 410b may have a range of approximately 1 mm to 15 mm. The thickness $t_a$ may have a range of approximately 0.01 mm to approximately 10 mm. A weld 420a, 420b may be disposed at a respective center 415a, 415b of the disk 410a, 410b, along a central horizontal axis 430. In contrast to anchor 300, the disks 410a, 410b may include a first and second extended end 435a, 435b, extending outward and connected to the respective weld 420a, 420b. For example, the braided nitinol may form an integral anchor 400 including a first extended end 435a, a first disk 410a, a connector 405, a second disk 410b, and a second extended end 435b.

Figure 4A:
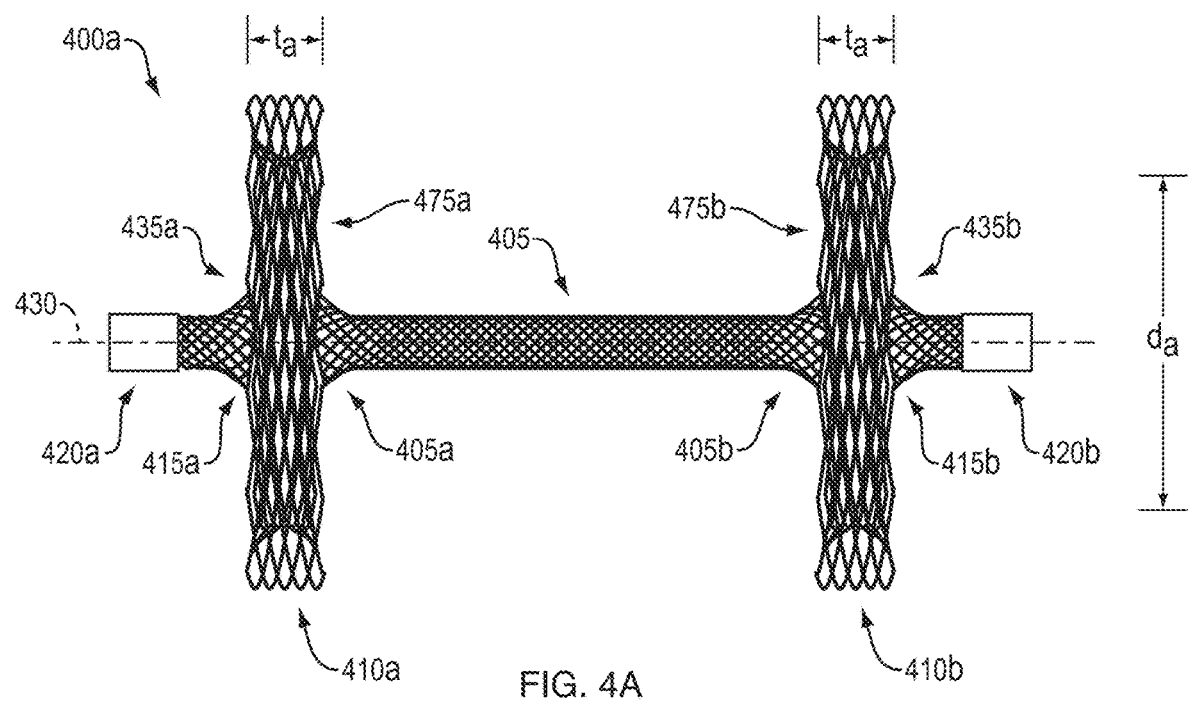
FIGS. 4A-4I illustrate exemplary embodiments of an anchor in accordance with the present disclosure.
Figure 4B:
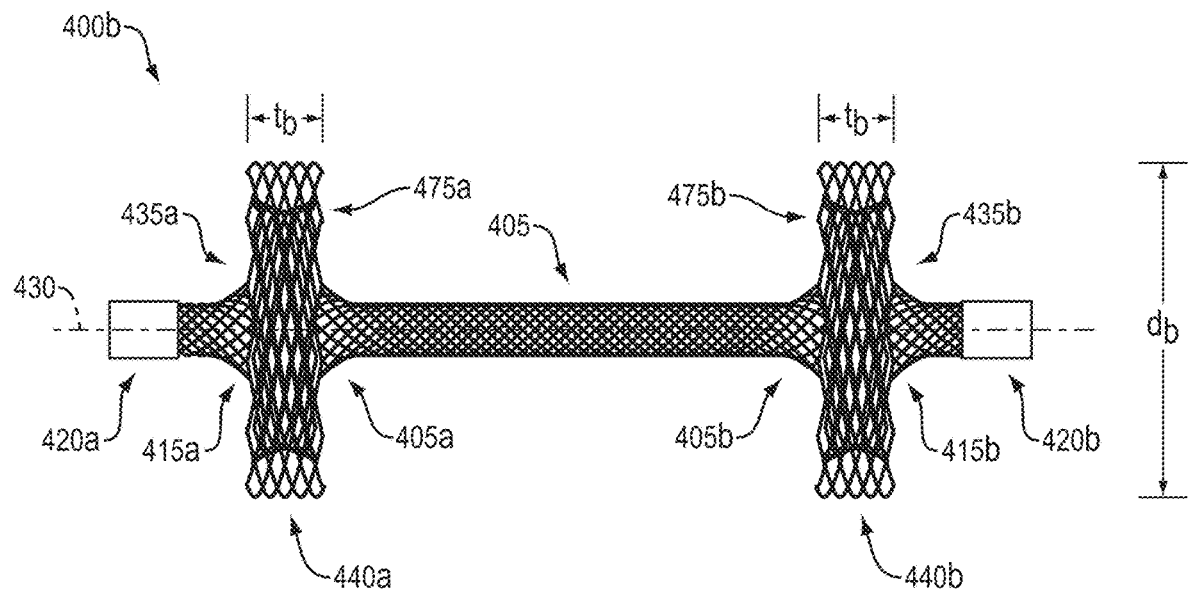
Figure 4C:
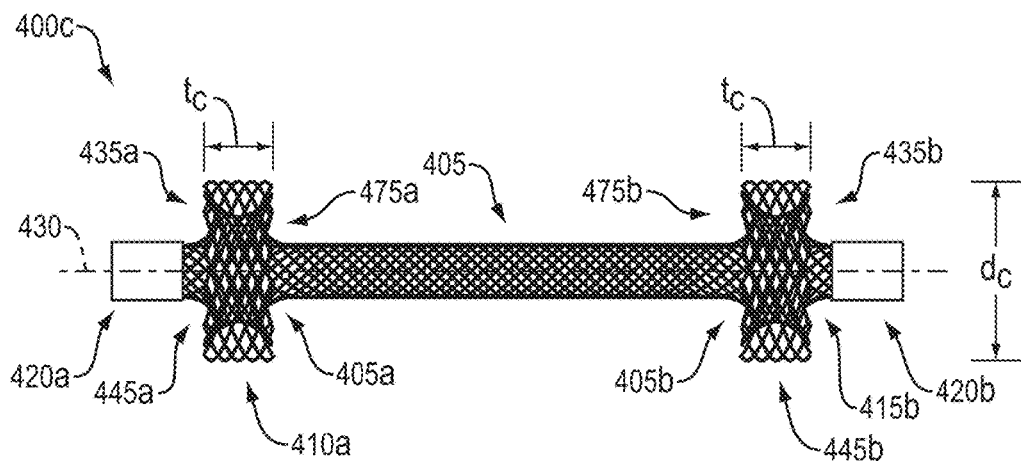
Figure 4D:
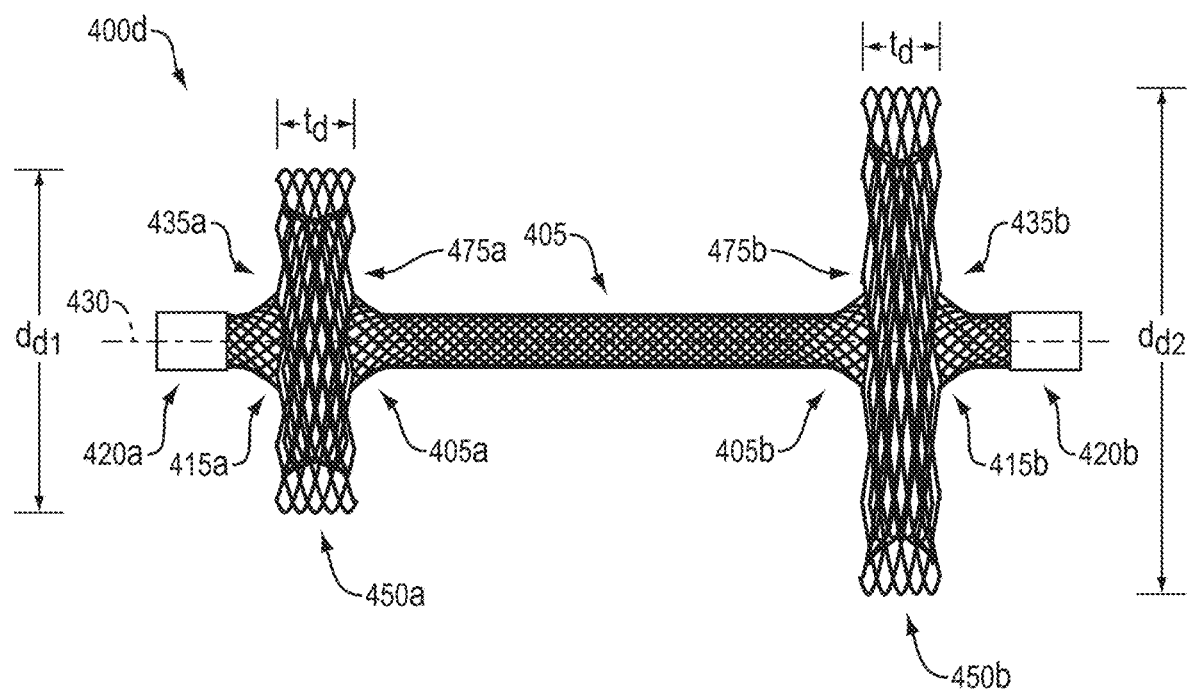

FIG. 4B illustrates an anchor 400b substantially similar to anchor 400a shown in FIG. 4A, except for first disk 440a and second disk 440b having a diameter $d_b$, which may be smaller than diameter $d_a$ of first and second disks 410a, 410b. For example, diameter $d_a$ may be approximately 10 mm, and diameter $d_b$ may be approximately 7 mm. FIG. 4C illustrates an anchor 400c substantially similar to anchors 400a and 400b shown in FIGS. 4A and 4B, except for first disk 445a and second disk 445b having a diameter $d_c$, which may be smaller than diameters $d_a$ of first and second disks 410a, 410b, and $d_b$ of first and second disks 440a, 440b. For example, diameter $d_c$ may be approximately 4 mm. FIG. 4D illustrates an anchor 400d substantially similar to anchors 400a, 400b, and 400c shown in FIGS. 4A, 4B, and 4C, except for first disk 450a and second disk 450b. The first disk 450a may have a first diameter $d_{d1}$, and the second disk 450b may have a second diameter $d_{d2}$. In contrast to anchors 300, 400a, 400b, and 400c, the first disk 450a may be sized differently from the second disk 450b. As illustrated, the first diameter of the first disk 450a may be smaller than the second diameter of the second disk 450b, $d_{d1}<d_{d2}$, although it is understood that in other embodiments the first diameter may be larger than the second diameter, $d_{d2}<d_{d1}$. Different diameters may be advantageous in that larger diameters may distribute the stress of the plication across the surface area of the respective disk, which may be beneficial for managing weaker areas of tissue and preventing tissue damage or tearing.

Figure 4E:
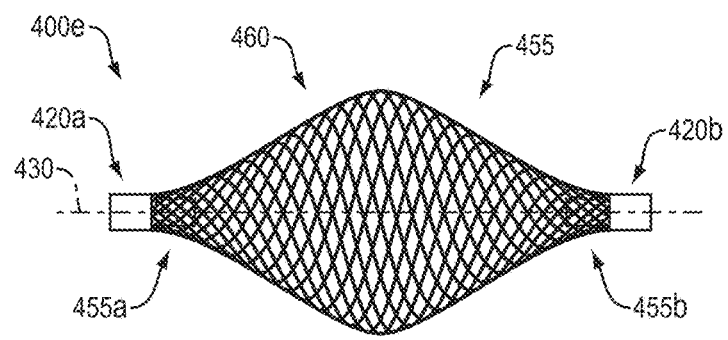

Anchor 400e illustrated in FIG. 4E may be a single bulb form 455 having a first end 455a and a second end 455b along central horizontal axis 430 and bounded by a first weld 420a and a second weld 420b. The single bulb form 455 may expand to a bulge 460 at a midpoint between the first end 455a and the second end 455b, which may expand to a diameter between 1 and 15 mm.

Figure 4F:
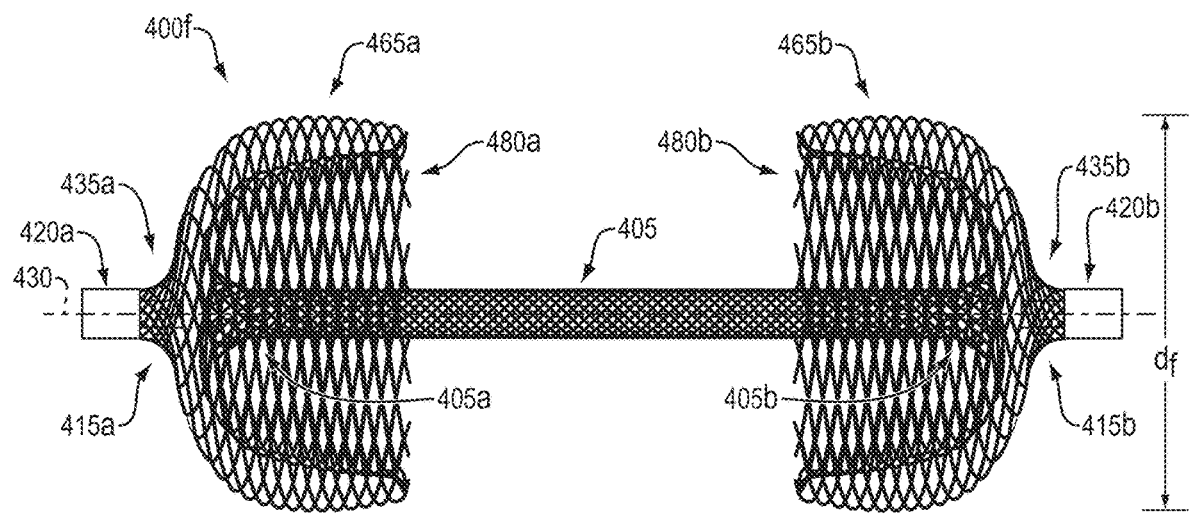

Anchor 400f illustrated in FIG. 4F may be similar to anchors 300 and 400a-400d, except instead of a first and second disk formed at respective ends of the connector, the anchor 400f may include a first umbrella, mushroom, or reverse concave end 465a and a second umbrella, mushroom, or reverse concave end 465b. For example, the first and second umbrella ends 465a, 465b may extend inward and away from the first and second welds 420a, 420b, over the respective first and second ends 405a, 405b, and a portion of the connector 405, like an umbrella. A first and second bottom portion 480a, 480b may extend inward along axis 430, and may be configured for displacement adjacent an annulus tissue. The first and second umbrella ends 465a, 465b may have a diameter $d_f$, and it is understood that the diameter of the first umbrella end 465a may be the same as or different from the second umbrella end 465b. Umbrella ends 465a, 465b may be advantageous in that they may be easily compressible in the delivery catheter described below, and self-expandable upon insertion into the annulus.

Figure 4G:
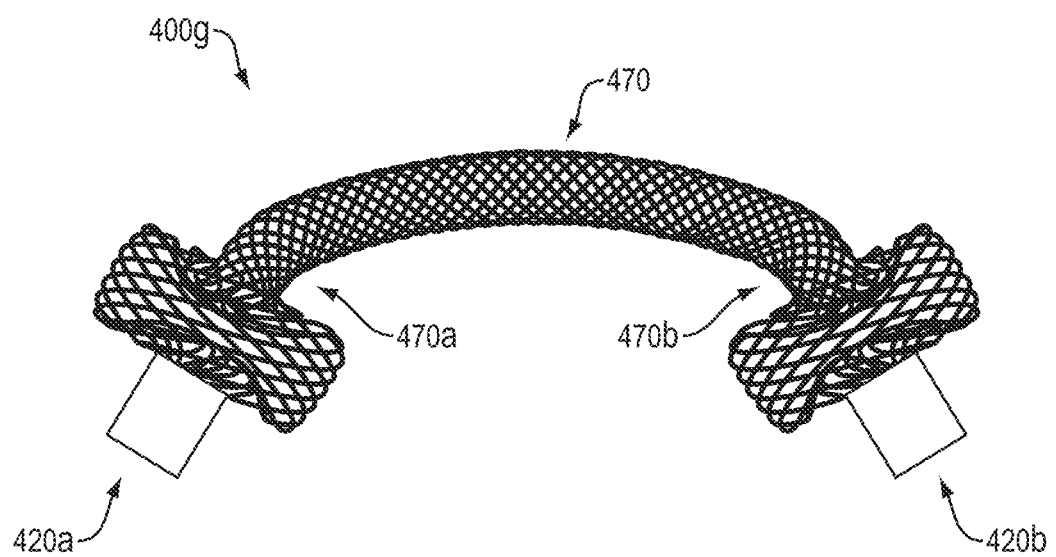

FIG. 4G illustrates anchor 400g, having a curved connector 470 having a first end 470a and a second end 470b. A first disk and a second disk may be coupled to the respective first and second end 470a, 470b via welds 420a, 420b, and may be any of disks 410a-410b, 440a-440b, 445a-445b, 450a-450b, or umbrella ends 465a-465b. As described above, the anchors 300 and 400a-400h may be formed of a flexible material, e.g., braided nitinol material. For example, the anchors 300 and 400a-400f may be flexible to bend in a curve. However, it may be advantageous to form a connector 470 having an initial curvature so that the anchor 400g has less elasticity to revert to an unbended shape. This may help prevent the anchor 400g from tearing out of the annulus once inserted, as will be described below.

Figure 4H:
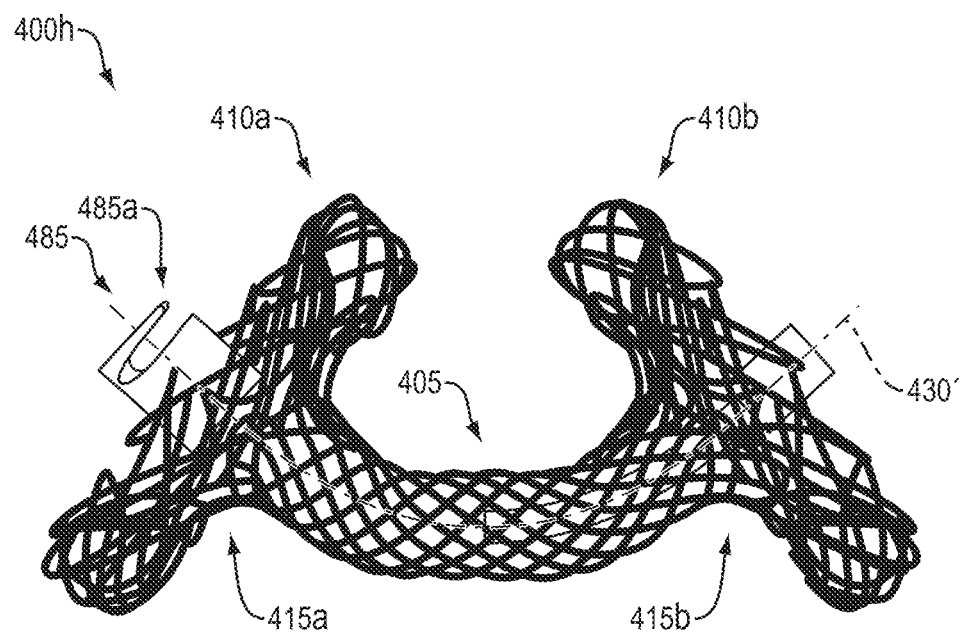
Figure 4I:
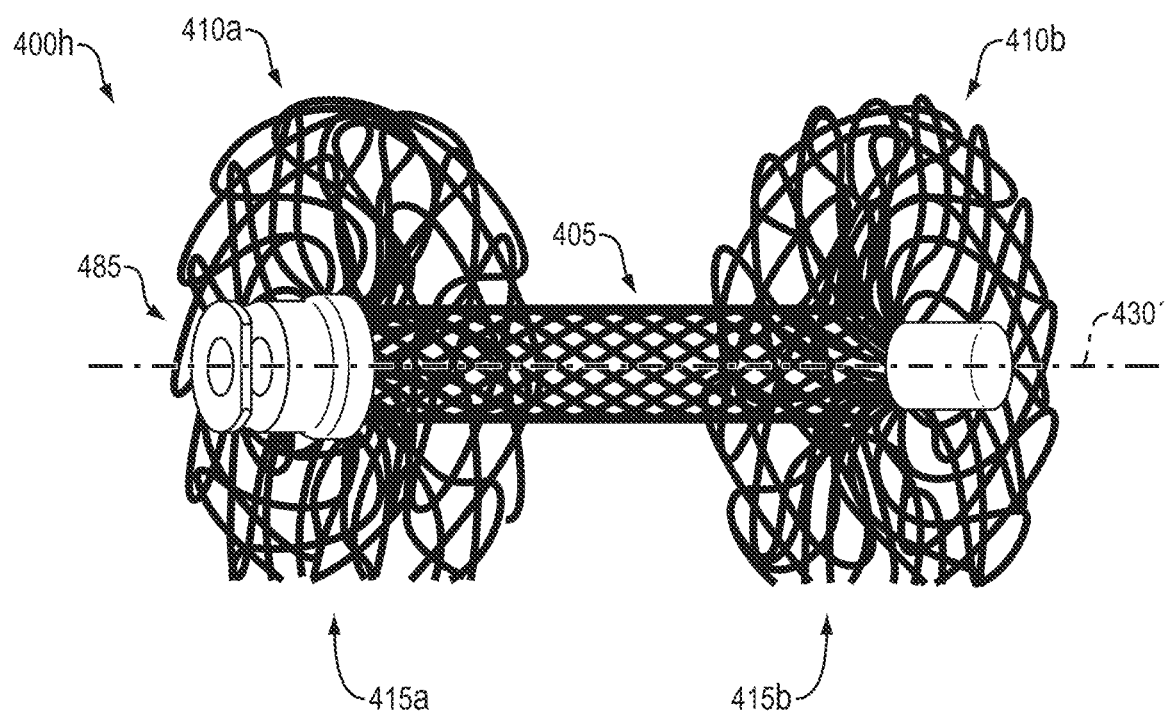

As shown in FIGS. 4H-4I, in addition or alternative to a weld 420a, 420b disposed on respective ends 415a, 415b of the bulbs 410a, 410b, a connector 485 may be disposed on an anchor 400h. It is understood that any anchor 300, 400a-400h may include a connector 485. The connector 485 may be disposed on either of the first or second ends 415a, 415b of the anchor 300, 400a-400h.

A connector 485 may be any connection feature to detachably couple an anchor to a distal end 486b of a stylet 486. In some embodiments, the connector 485 may be hooks 485a, which may be formed relative to the central axis 430' of the anchor. A hook 485a may extend in a first direction. As shown in FIG. 4H, the hook 485a may extend outward from the bulb 410a, longitudinally and parallel relative to the central axis 430' of the anchor. In this manner, a mating configuration may engage and/or disengage for locking and/or unlocking the anchor from the distal tip 486c of the stylet 486.

Figure 17:
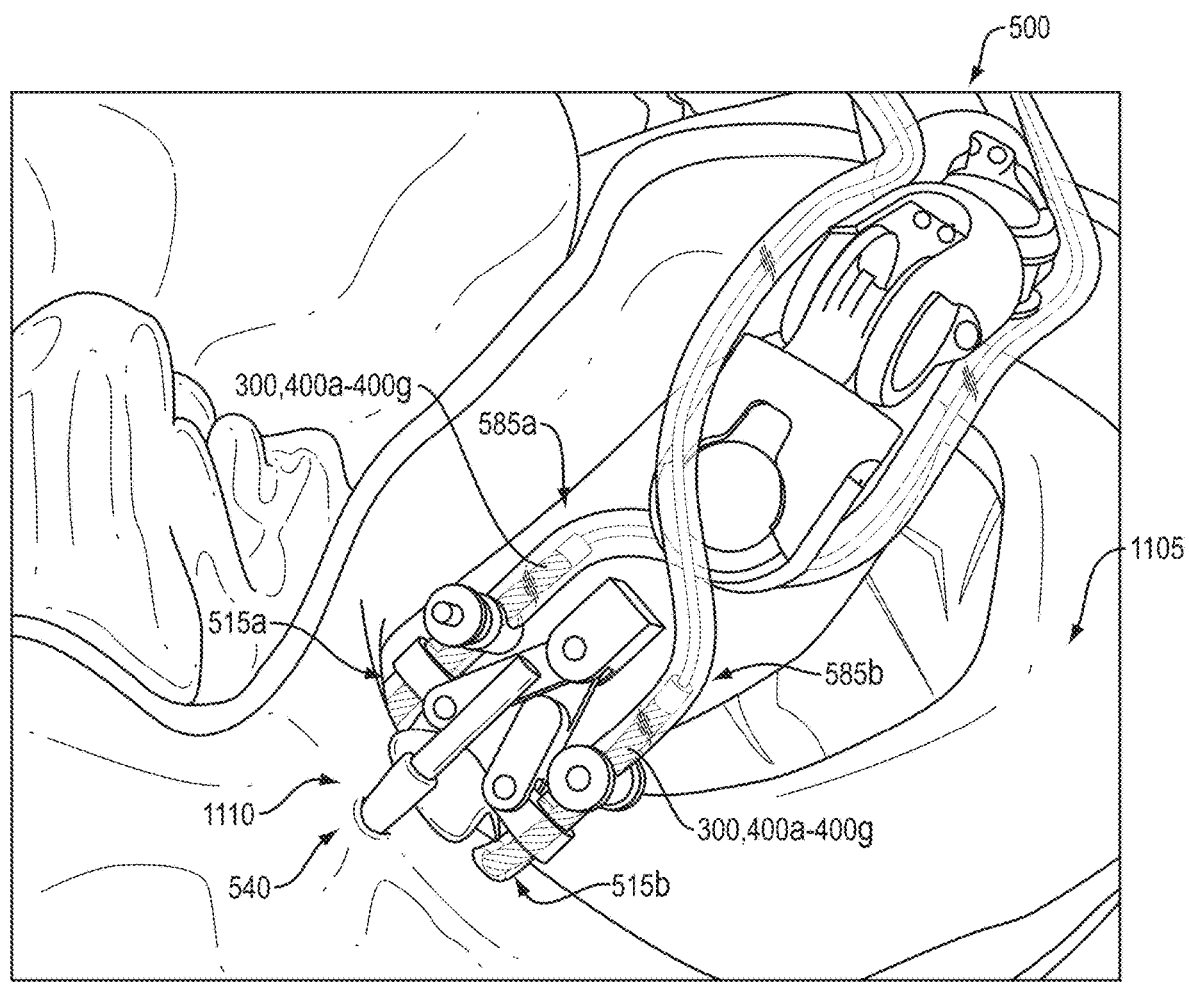
Figure 17A:
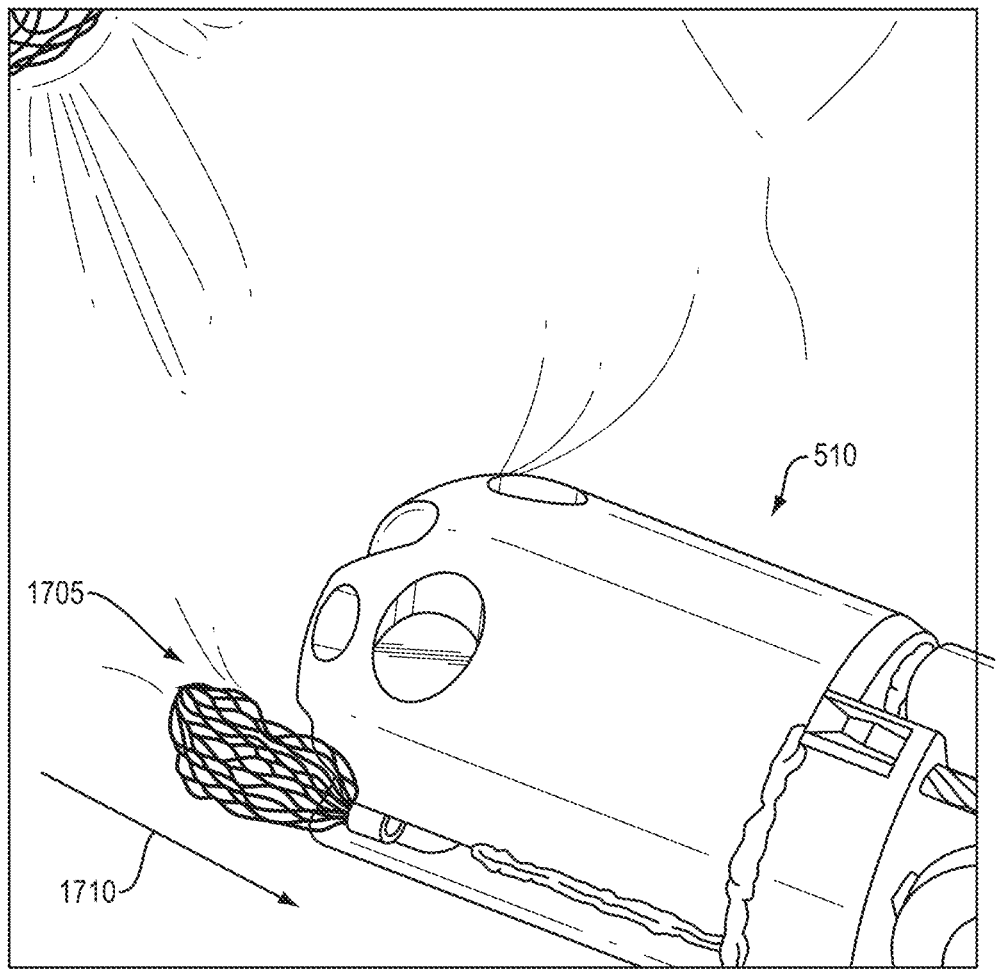
FIGS. 17A-17D illustrate another exemplary embodiment of an anchor delivery method in accordance with the present disclosure.
Figure 17B:
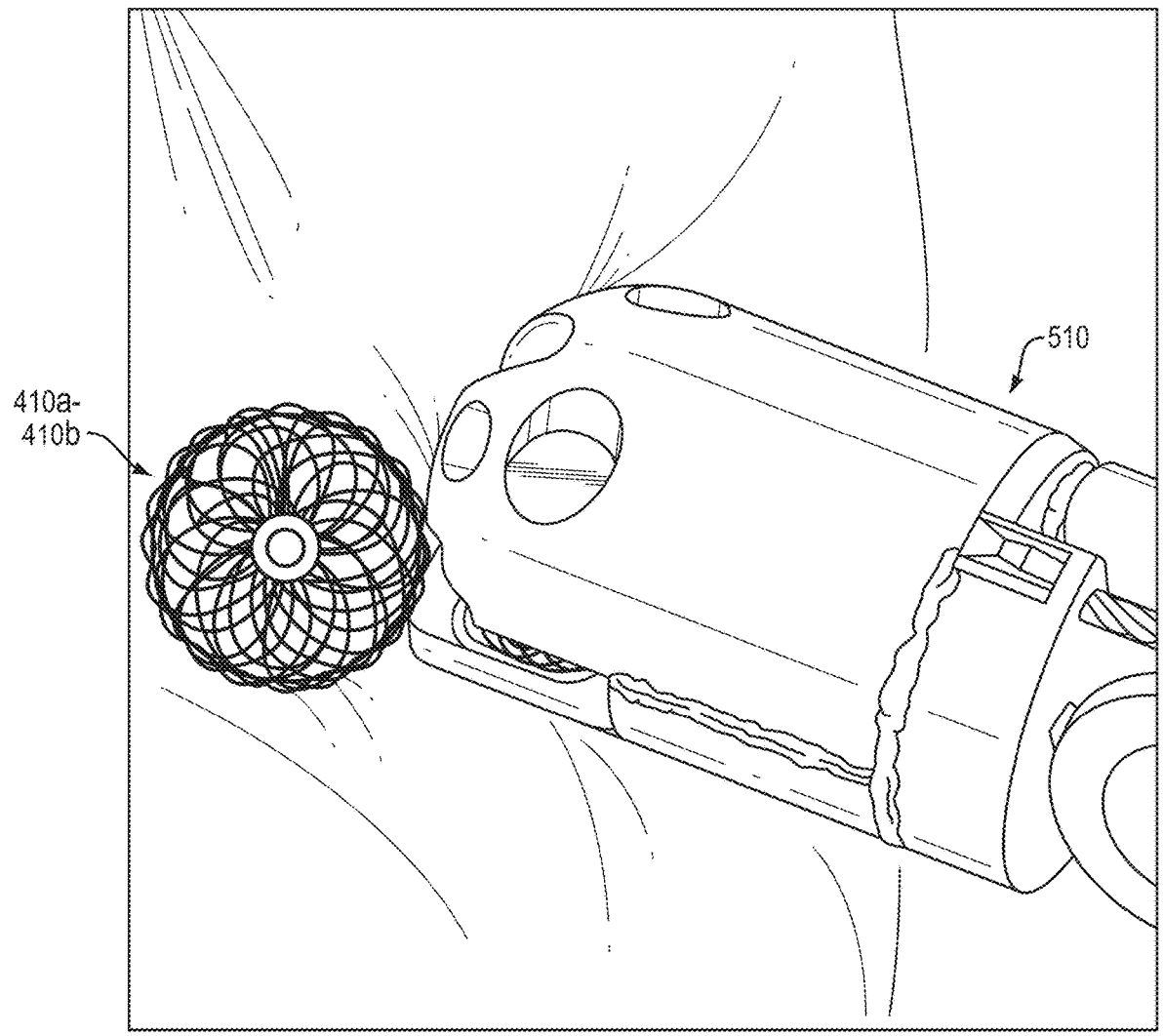
Figure 17C:
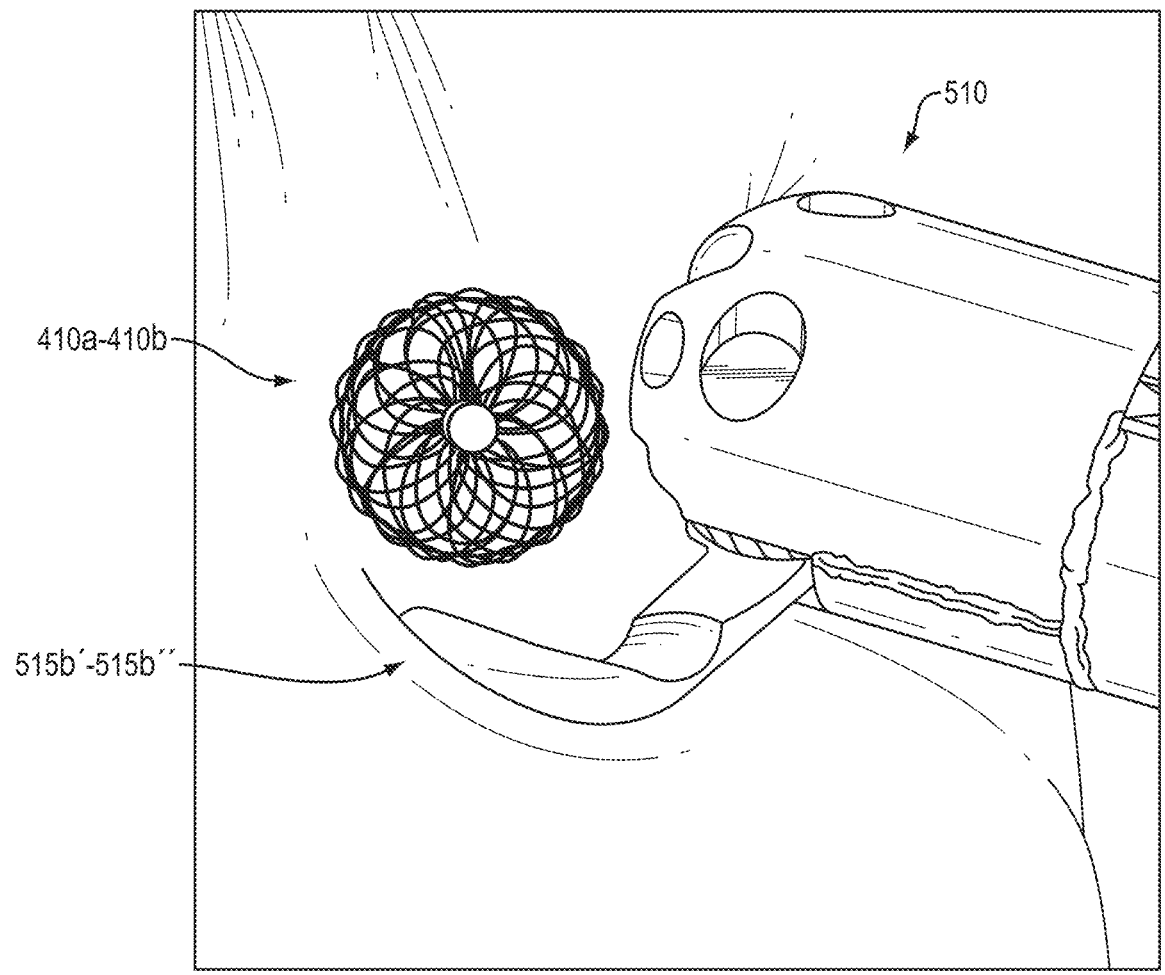
Figure 17D:
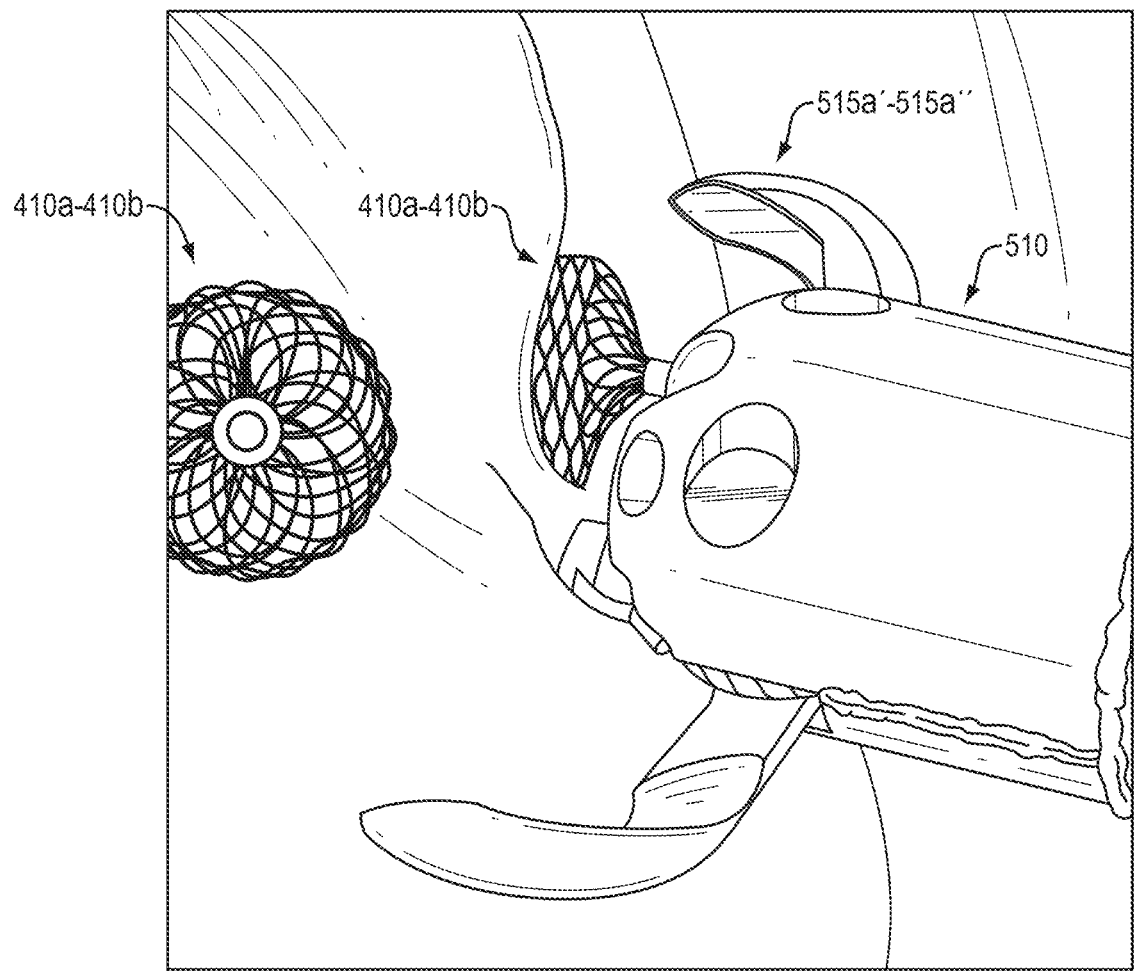
Figure 17E:
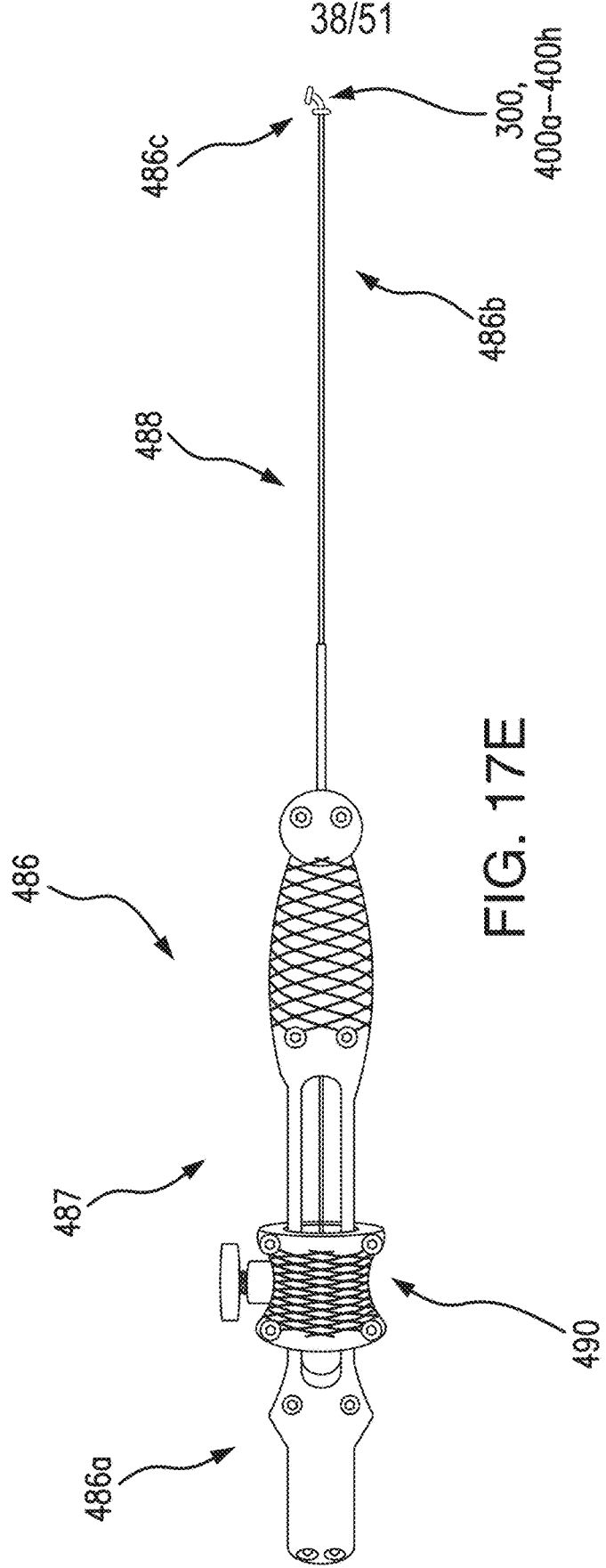
FIGS. 17E-17I illustrate an exemplary embodiment of a stylet for anchor delivery in the method of FIGS. 17A-17D.
Figure 17F:
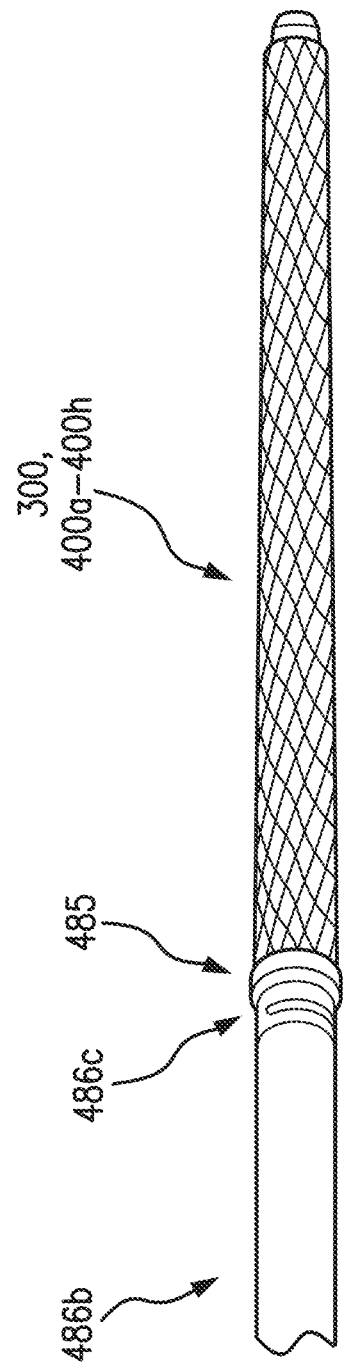
Figure 17G:
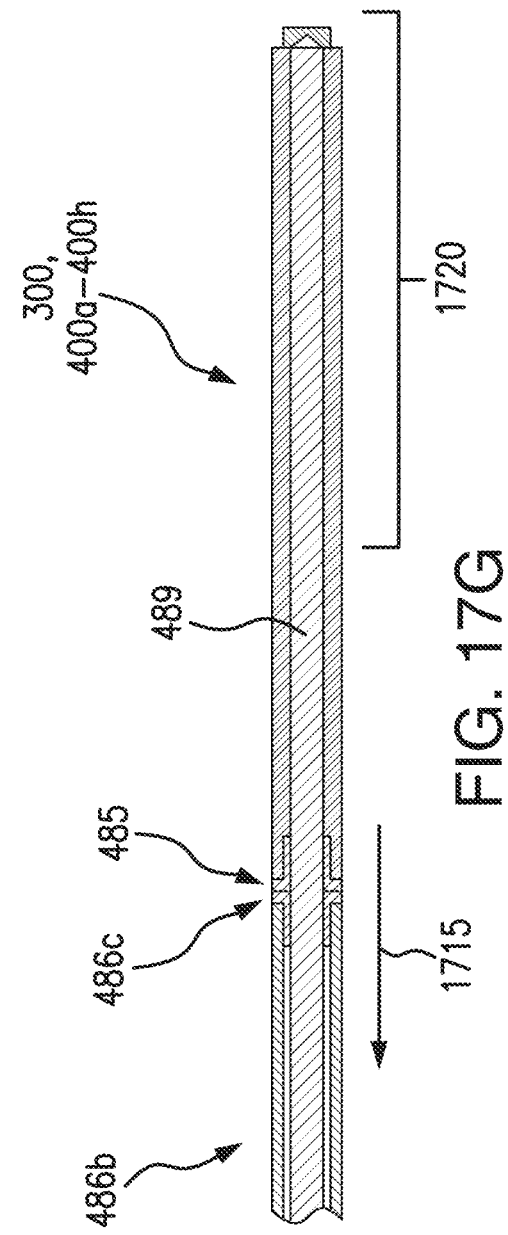

As shown in FIGS. 17E-17G, a stylet 486 may be configured for delivering an anchor 300, 400a-400h though a delivery catheter device as described below. In some embodiments, the stylet 486 may have a handle 487 disposed at a proximal end 486a and a delivery catheter 488 disposed at the distal end 486b. A user may manipulate the handle 487 of the stylet for locking and/or unlocking an anchor 300, 400a-400h detachably coupled to a distal tip 486c of the stylet 486. In some embodiments, the distal tip 486c may be configured to mate with the connector 485 of the anchor 300, 400a-400h. For example, the distal tip 486c may include one or more projections for mating with the hook 485a. A projection on the distal tip 486c may mate in the hook 485a, and a projection on the hook 485a may mate in an indent of the distal tip 486c (see FIGS. 17H-17I). In some embodiments, the projection on the connector 485 or the distal tip 486c may include a taper, a chamfer, or other lead-in feature to aid in alignment of the stylet 486 and the anchor 300, 400a-400h during engagement/disengagement.

In embodiments, the stylet 486 may tow an anchor 300, 400a-400h through the delivery catheter for placement in the patient. The anchor 300, 400a-400h may be deliverable in a compressed or unexpanded first state, and may include an inner coil 489 extending through the delivery catheter 488 and through the anchor 300, 400a-400h. The inner coil 489 may pin a proximal end of the anchor 300, 400a-400h to the distal tip 486c of the stylet 486 in a "locked" position (e.g., the anchor 300, 400a-400h may be coupled to the distal tip 486c of the stylet 486). The inner coil 489 may be movable by a medical professional by a movable portion 490 of the handle 487 to retract the inner coil from within the anchor, allowing the anchor to detach from the distal end of the delivery catheter.

Figure 5:
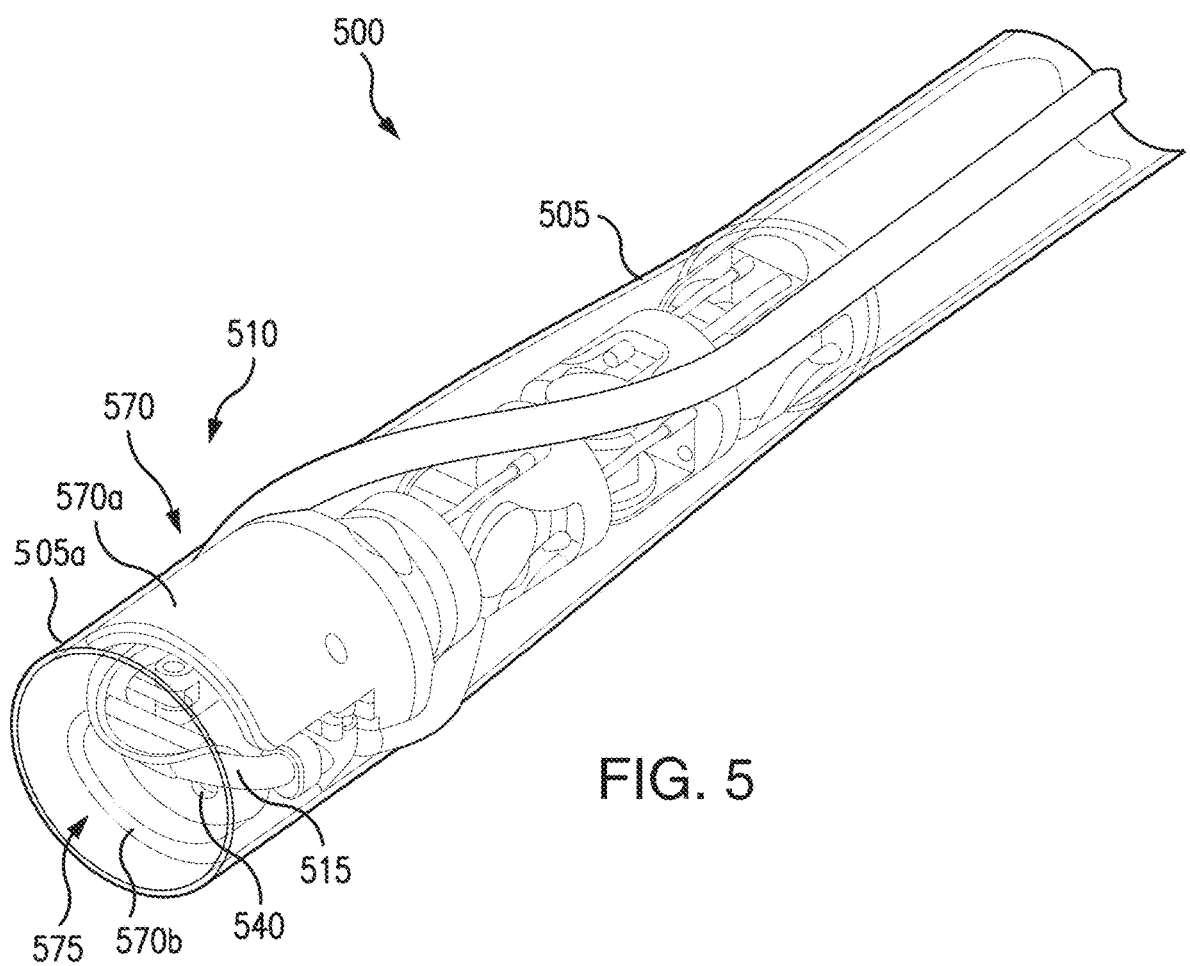
FIG. 5 is a perspective view of an exemplary embodiment of an anchor delivery device in accordance with the present disclosure.
Figure 6:
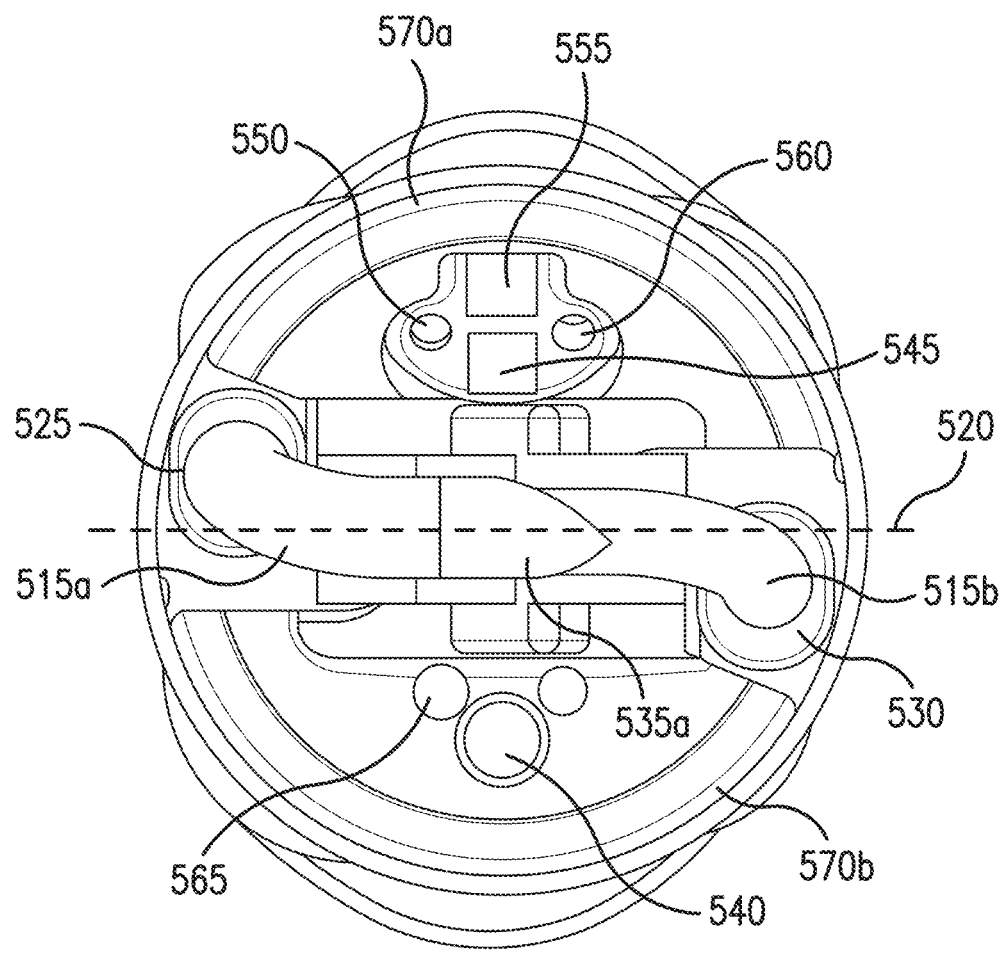
FIG. 6 is a front view of an exemplary embodiment of the anchor delivery device of FIG. 5.

Referring now to FIGS. 5-10, an exemplary embodiment of a delivery catheter device in accordance with the present disclosure is illustrated. The delivery catheter may be used in an anchor delivery system for repairing a heart valve. FIG. 5 illustrates a perspective view of a distal end 510 of delivery catheter 500, the delivery catheter 500 having a sheath 505, which is transparent only for illustrative purposes. The sheath 505 may have a flexible distal portion 505a, that may be expandable in response to the delivery catheter 500 preparing to deliver an anchor, such as anchor 300, 400a-400h. The delivery catheter 500 may be configured to deliver a single type of anchor 300, 400a-400h, although the delivery catheter 500 may deliver any combination of anchors, e.g., as exemplary embodiments of anchors 300, 400a-400h. In some embodiments, the flexible distal portion 505a may be an outer balloon that is expandable, clearing a view for camera 545 to verify anchor placement, so that a user may verify both bulbs, or disks. For example, FIG. 5 shows pincers 515a, 515b in a closed position, and FIG. 6 illustrates a front view of the distal end 510 of the delivery catheter 500, and shows pincers 515 in the closed position.

Figure 7:
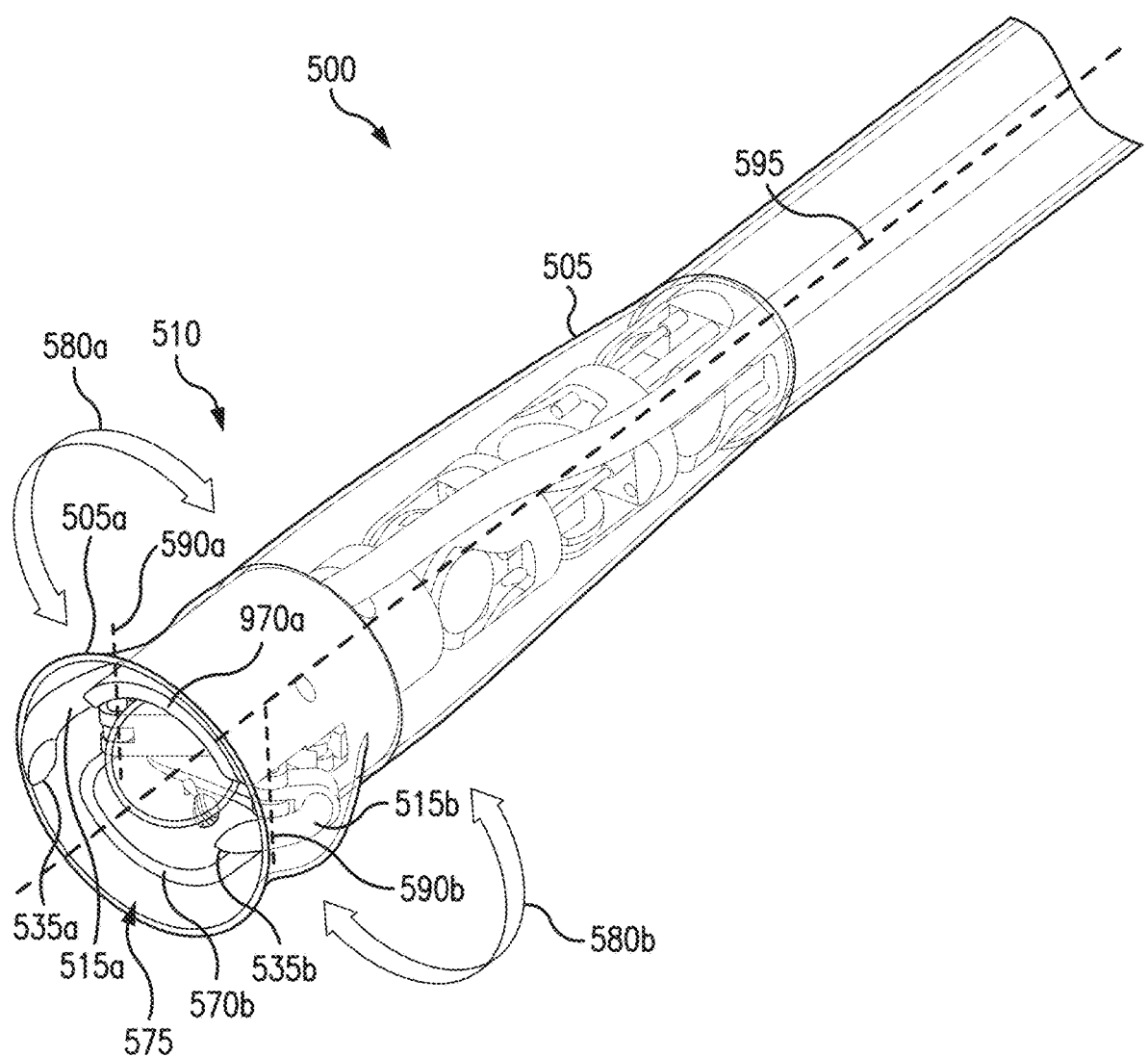
FIG. 7 is a perspective view of an exemplary embodiment of the anchor delivery device of FIG. 5 in an open configuration.

Pincer arms 515a, 515b may be disposed on a head 511 at the distal end 510 of the delivery catheter 500. A first pincer arm 515a may be disposed on a diameter of the delivery catheter directly opposite from a second pincer arm 515b, and actuatable, e.g., rotatable, between an open position extending distally of the distal end 510 (see FIG. 7), and a closed position (see FIG. 5). In some embodiments, the first and second pincer arms 515a, 515b may be retractable to an open position via a rotating pulley cable mechanism. It is understood that the first and second pincer arms 515a, 515b, as well as first and second pincer arms 515a', 515a", 515b', 515b" may be rotatable about respective axes, such as axes 590a, 590b, relative to the distal end 510 or head 511, 511', as illustrated in FIG. 7. The first and second pincer arms 515a, 515b may each be formed of a hollow tube having a sharp, pointed distal end 535a, 535b. In some embodiments, the distal end 535a, 535b may be traumatic, or may include a burr, or other mechanism configured for piercing tissue. Anchor delivery tubes 585a, 585b may be attached to the respective first and second pincer arms 515a, 515b, for delivering an anchor, such as anchor 300, 400a-400h, described below with respect to FIGS. 11-26, and extend to a proximal portion of the delivery catheter 500. In some embodiments, the first and second pincer arms 515a, 515b may be formed of a rigid material, including but not limited to metal, composite, plastic, or the like. A rigid material may be advantageous so that pincer arms 515a, 515b may have a reliable and repeatable shape. In some embodiments, the first and second pincer arms 515a, 515b may be formed of a superelastic material. It may be advantageous to use a superelastic material so that the pincer arms 515a, 515b may be easier to fit within a catheter lumen, in that the pincer arms 515a, 515b may have a lower profile when retracted.

FIGS. 5A-5F illustrate other embodiments of pincer arms 515a, 515b that may be included in the delivery catheter 500. It is understood that pincer arms 515a, 515b, 515a', 515b', and 515a", 515b" may have similar features except as described. Referring now to FIGS. 5A-5D, a first pincer arm 515a' may be formed as an at least a partially open tube 516. For example, the at least partially open tube may be open along a length of the arm 515a', forming a slide or canoe-like shape. As described below, an anchor 300, 400a-400h, in a compressed, or unexpanded, state may be towed along an inner surface 517 of the at least partially open tube 516. When the pincer arms 515a', 515b' are in a closed position (see FIG. 5), the anchor 300, 400a-400h may pass through the first pincer arm 515a' into the second pincer arm 515b'. In some embodiments, the first pincer arm 515a' may be a pass-through needle.

The second pincer arm 515b' may also be an at least partially open tube, and may have an open curvature 518, for example, an inner surface 519 of the open curvature 518 may be curved for receiving an anchor 300, 400a-400h from the first pincer arm 515a'. In some embodiments, the open curvature 518 may extend at least partially around the body of the tube to form a partial tube diameter towards the distal end 535b' (see FIG. 5C). The open curvature 518 may include an opening 518a, so that an anchor 300, 400a-400h may be towed through from the first pincer arm 515a' to the second pincer arm 515b'. As described below, when the anchor 300, 400a-400h is delivered to the tissue, the open curvature 518 of the second pincer arm 515b' may allow the arm to rotate, or retract, outward to separate from the anchor 300, 400a-400h (see FIGS. 17A-17D). In embodiments, the opening 518a may be configured to align an end of the anchor 300, 400a-400h, so that a bulb of the anchor 300, 400a-400h extending through tissue during deployment may be substantially parallel to longitudinal axis 595. For example, the open curvature 518 and opening 518a may form a "side shooter" opening for the anchor 300, 400a-400h to be deployed into tissue substantially along an axis 512. In some embodiments, pincer arms 515a, 515a', 515b, 515b' may have a curvature "C" formed in the respective arms between the head 511 and the respective distal ends 535a, 535a', 535b, 535b'. In this manner, the curvature "C" of the respective pincer arms may allow the respective distal ends to mate together at a distal end of the delivery catheter when the pincer arms are in a closed position. It is understood that in some embodiments the first and second pincer arms may both include a curvature "C" and may both be actuatable, or rotatable about respective axes 590a, 590b, and relative to the axis 595 (see FIG. 7).

Figure 5A:
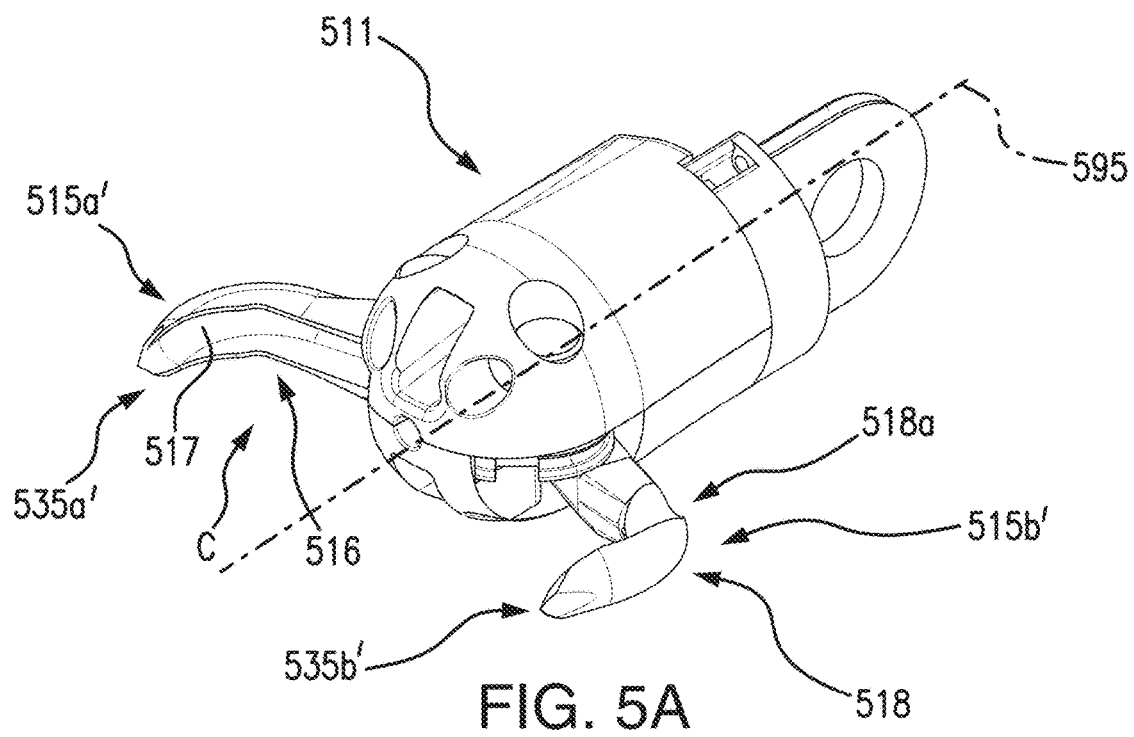
FIGS. 5A-5D illustrate an exemplary embodiment of a distal end of an anchor delivery device in accordance with the present disclosure.
Figure 5B:
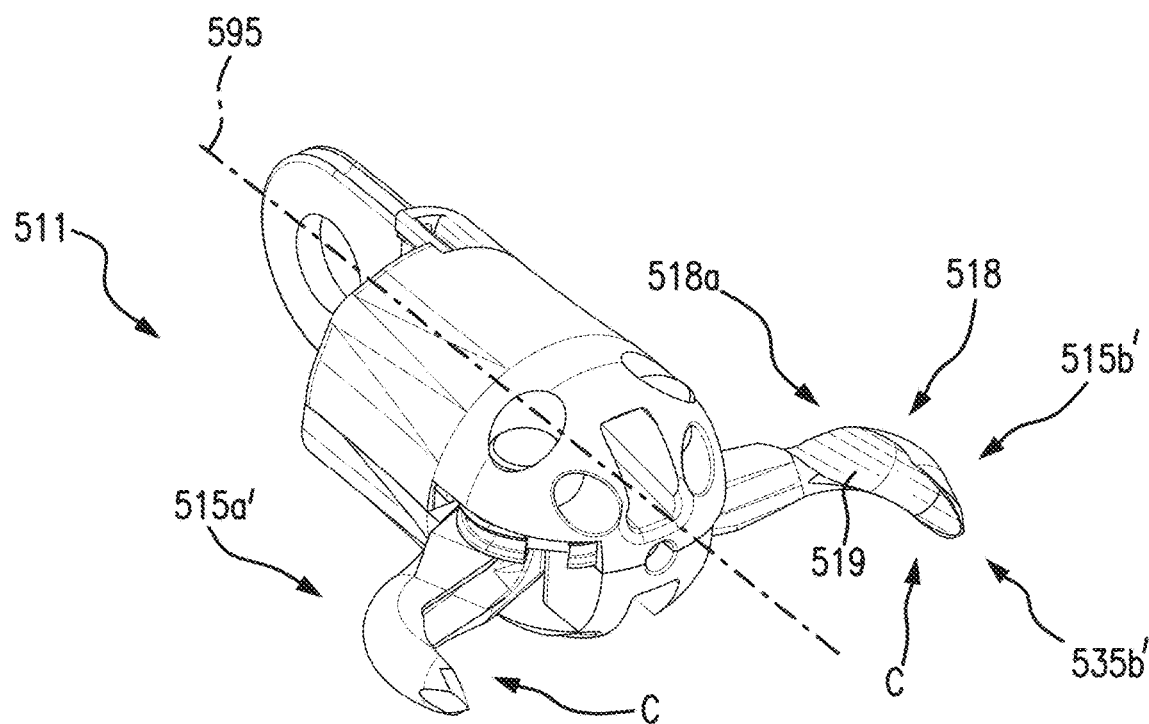
Figure 5C:
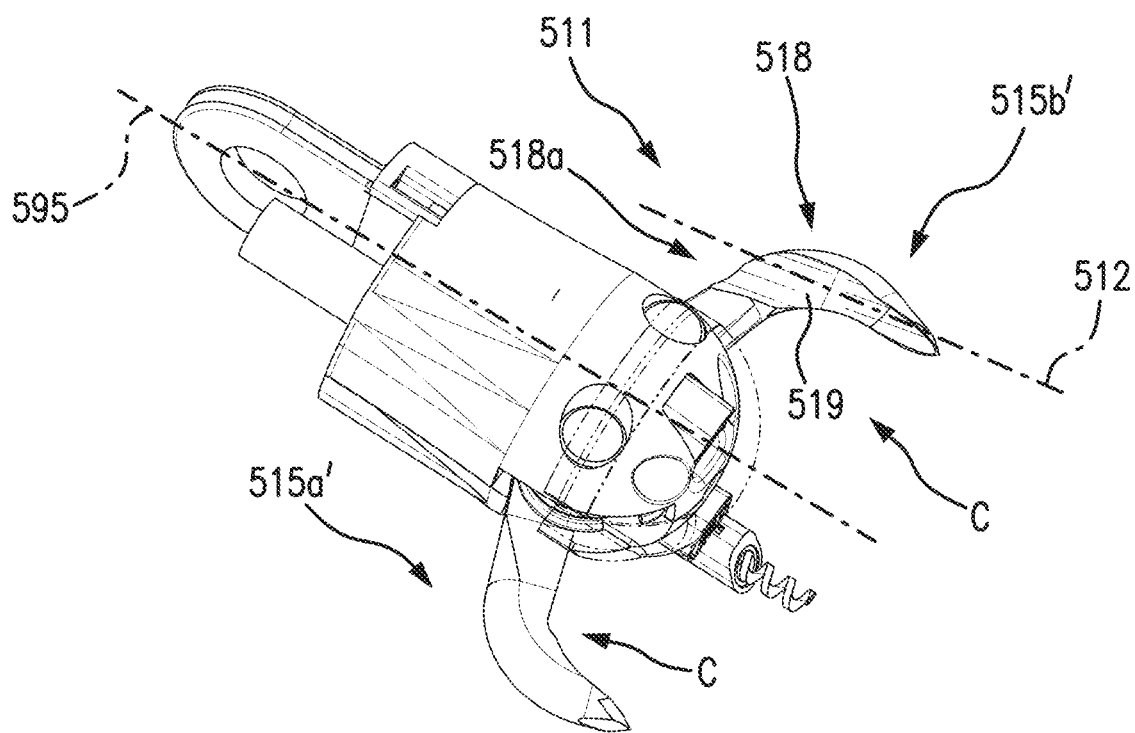
Figure 5D:
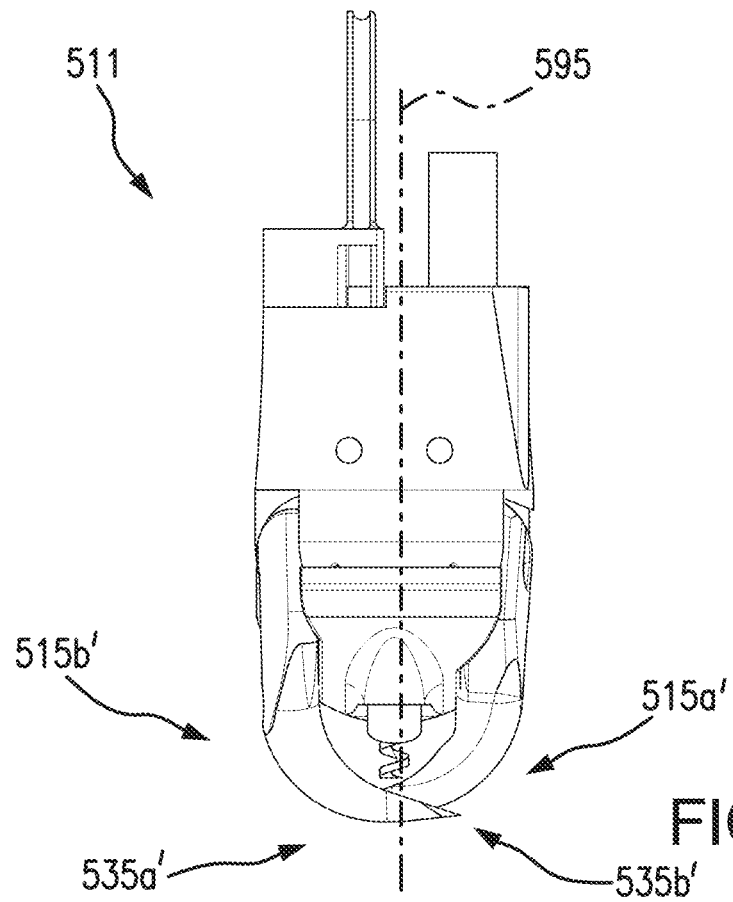
Figure 5E:
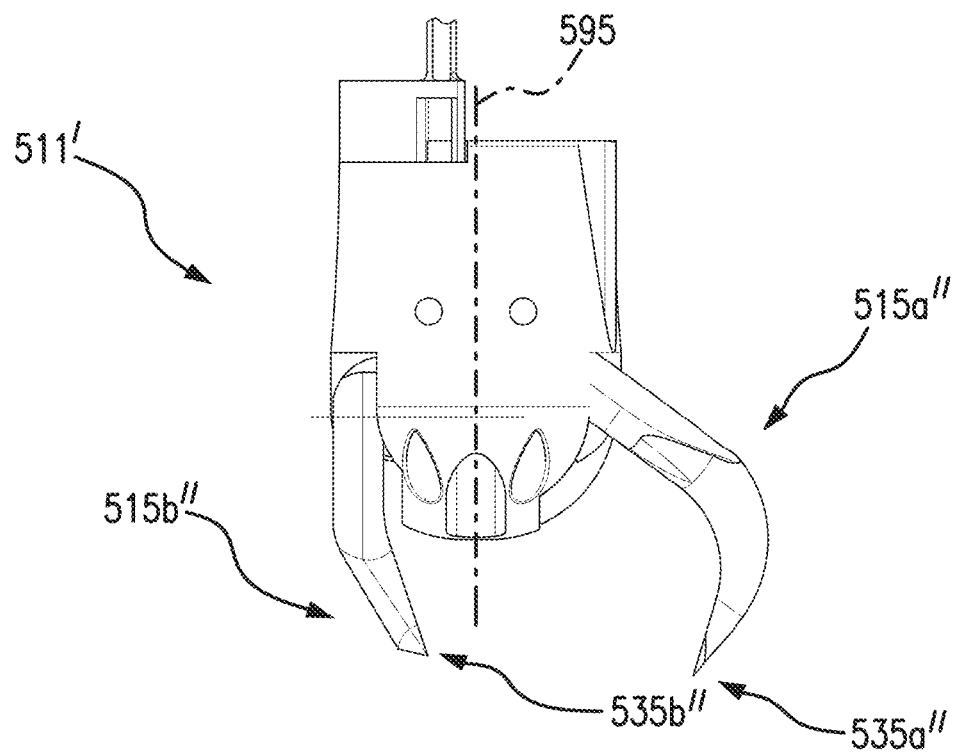
FIGS. 5E-5F illustrate another exemplary embodiment of a distal end of an anchor delivery device in accordance with the present disclosure.
Figure 5F:
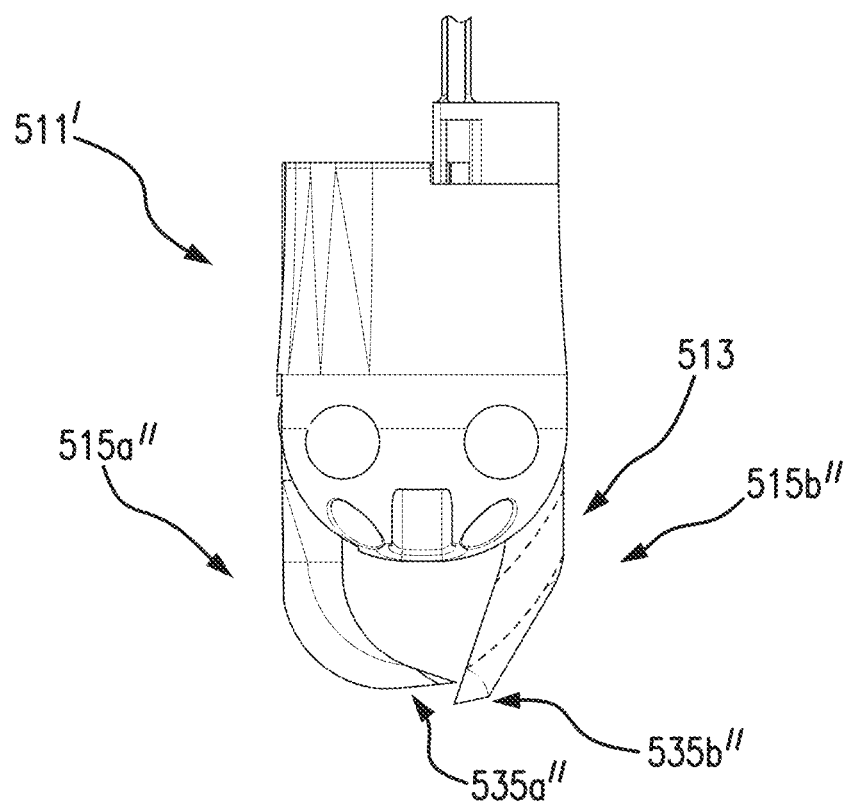

Referring now to FIGS. 5E-5F, another embodiment of pincer arms 515a", 515b" is shown. Instead of both the first and second pincer arms having a curvature "C" to mate together (see FIGS. 5A-5D), a first pincer arm 515a" may have a curvature "C" while a second pincer arm 515b" may be substantially straight, or straighter than the first pincer arm 515a". In embodiments, the first pincer arm 515a" may be similar to the first pincer arm 515a', including having a partially open tube 516. For example, the at least partially open tube may be open along a length of the arm 515a", forming a slide or canoe-like shape. The second pincer arm 515b" may be substantially straight, e.g., extending from the head 511' to the distal tip 535b". In some embodiments, the second pincer arm 515b" may stabilize the first pincer arm 515a" during opening and closing, although it is understood that in other embodiments the second pincer arm 515b" may also be rotatable (see FIG. 7). The second pincer arm 515b" may stabilize the first pincer arm 515a", e.g., so that an anchor may be delivered into the tissue in a controlled manner. For example, the distal ends 535a", 535b" may more repeatably and reliably meet together when only one pincer arm (e.g., the first pincer arm 515a") is movable and the other pincer arm (e.g., the second pincer arm 515b") is stable. Independent movement of the first and second pincer arms 515a", 515b" may improve control over tissue plication for a more standardized anchor placement. It is also understood that arms 515a, 515b, 515a", 515b" may also be independently movable or rotatable, and/or may be movable together, e.g., individually or simultaneously retractable.

The second pincer arm 515b" may have an open curvature 518' and opening 518a' similar to the open curvature 518 in the second pincer arm 515b' as shown in FIGS. 5A-5C. As shown in FIG. 5E, the open curvature 518' and the opening 518a' may form a passage 513, so the anchor may be towed through and delivered into the tissue. In this manner, the second pincer arm 515b" may form a "side shooter" passage.

It is understood that the first and second pincer arms 515a, 515a', 515a", 515b, 515b', 515b" may be interchangeable with each other, and may form any combination in the delivery catheter 500. Additionally, any of the first and second pincer arms 515a, 515a', 515a", 515b, 515b', 515b" may be incorporated in the delivery catheter as illustrated in FIGS. 5-9.

In some embodiments, the delivery catheter 500 may be substantially circular, so that the first pincer arm 515a, 515a', 515a", may be disposed substantially across a diameter of the delivery catheter 500. In some embodiments, the first pincer arm 515a, 515a', 515a" may be offset from the second pincer arm 515b, 515b', 515b". As illustrated in FIG. 6, a horizontal axis 520 may bisects the delivery catheter 500 into an upper portion and a lower portion. A connection point 525 may be at a proximal end of the first pincer arm 515a, 515a', 515a" above the horizontal axis 520, and a connection point 530 may be at a proximal end of the second pincer arm 515b, 515b', 515b", below the horizontal axis 520. The first and/or second pincer arms 515a, 515a', 515a", 515b, 515b', 515b" may include a curvature "C" so that distal ends 535a, 535a', 535a", 535b, 535b', 535b", of the first and second pincer arms 515a, 515a', 515a", 515b, 515b', 515b" may be positionable centrally in the delivery catheter 500. It is understood that in some embodiments, the second pincer arm 515b" may have less of a curvature "C" or no curvature "C", and the distal end 535b" may be positionable to a distal end 535a" of the first pincer arm 515a". For example, the first pincer arm 515a, 515a', 515a" may be foldable with respect to respective pincer arm 515b, 515b', 515b" when in the closed position so that distal ends of the first and second pincer arms 515a, 515a', 515a", 515b, 515b', 515b" are substantially mated with each other or positioned together as described above with respect to the various embodiments.

Figure 11A:
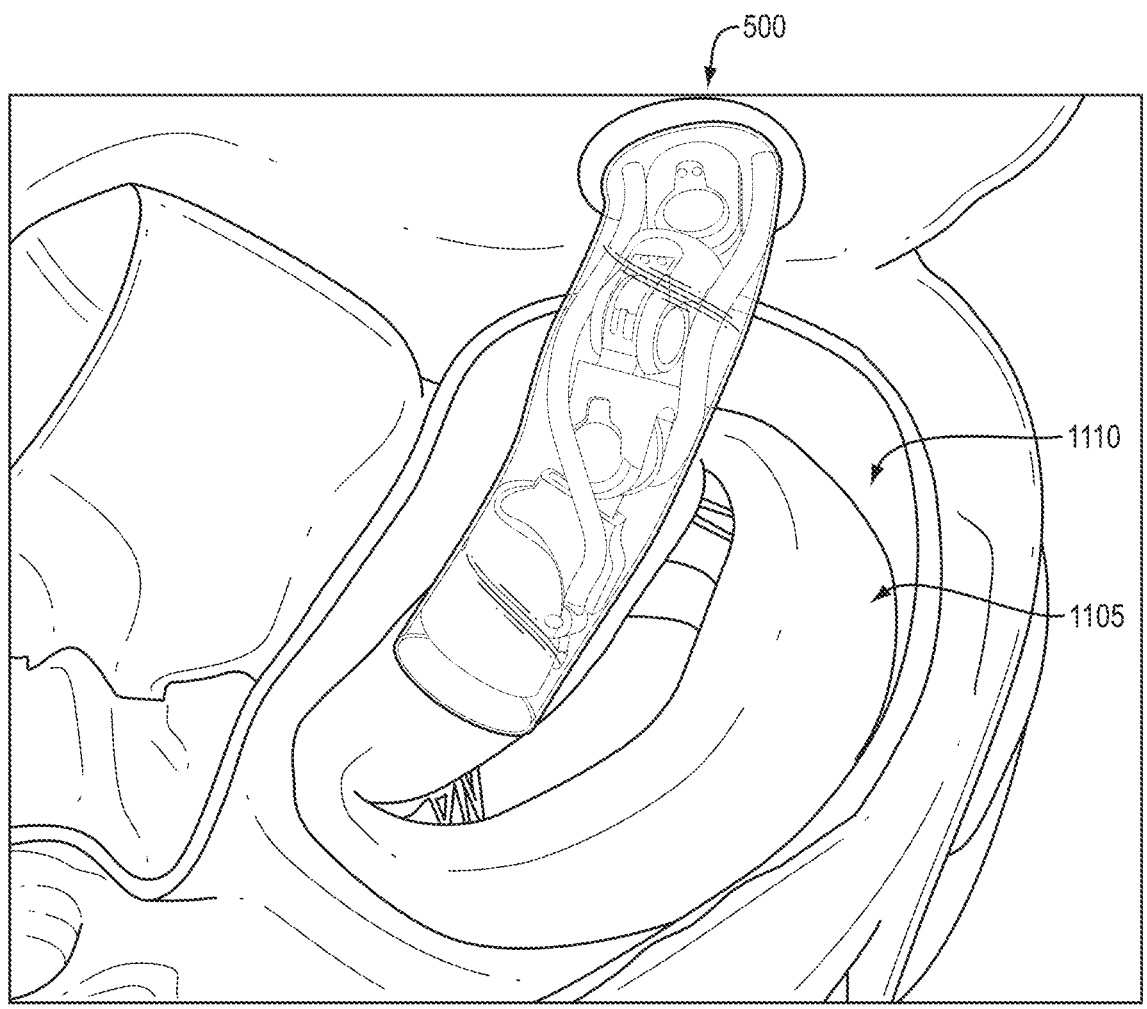
FIGS. 11A-11B illustrate an exemplary embodiment of an anchor delivery method of accessing a valve by an anchor delivery catheter in accordance with the present disclosure.
Figure 11B:
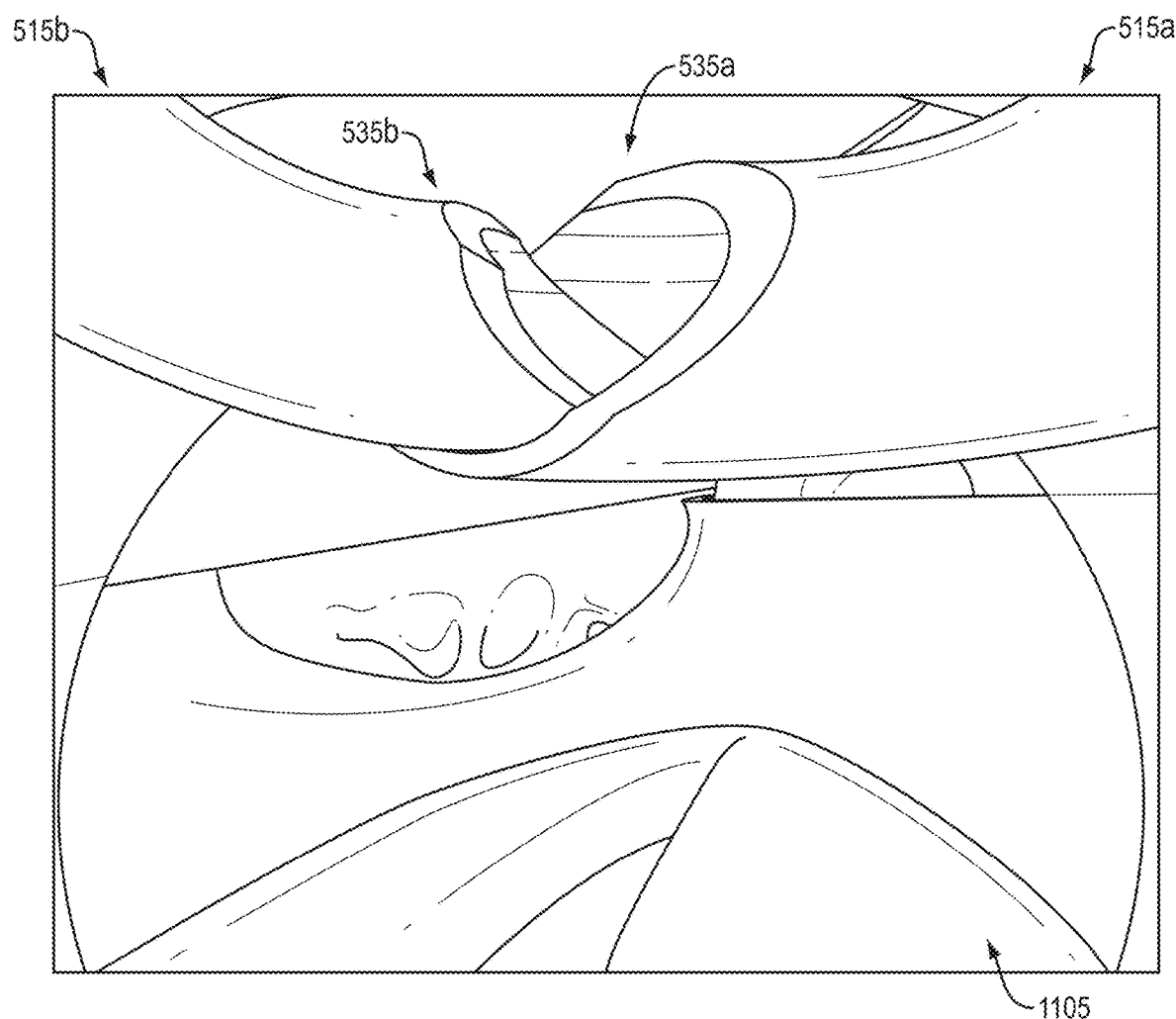

In some embodiments, in a closed position the second pincer arm 515b may have at least a portion of the distal end 535b contacting an inner surface of the distal end 535a of the first pincer arm 515a (FIG. 11B). In the closed position, the distal ends 535a, 535b of the first and second pincer arms 515a, 515b may be mated together substantially central to the delivery catheter 500 (FIG. 6). In other embodiments, at least a portion of the first pincer arm 515a' may contact the inner surface 519 of the second pincer arm 515b'. It is understood that whichever pincer arm the anchor 300, 400a-400h is initially passed through for deployment should be interiorly positioned with respect to the other pincer arm. For example, the "pass through" needle, or pincer arm, should be mated inside of a "side shooter" pincer arm, so that the first distal end 535a' of the first pincer arm 515a' may contact an inner surface 519, and the second distal end 535b' of the second pincer arm 515b' may be disposed outward of the first pincer arm 515a' (see FIG. 5D). In this manner, the distal end 535a' of the first pincer arm 515a' may be nested within the distal end 535b' of the second pincer arm 515b'. This may be advantageous for the anchor to easily slide, or "pass through" the first pincer arm 515a' into the second pincer arm 515b'.

In some embodiments, the first distal end 535a" and the second distal end 535b" may close together without the first and second arms 515a", 515b" mating together. As shown for example in FIG. 5F, the first pincer arm 515a" may have a curvature "C" and be actuatable, or rotatable, with respect to the straighter, second pincer arm 515b". For example, the first and second pincer arms 515a", 515b" may be rotatable about respective axes 590a, 590b, relative to a distal end 510, or head 511, 511'. In this manner, the distal ends 535a", 535b" may close together, so than an anchor 300, 400a-400h may be passed through the first pincer arm 515a" to the side shooter passage 513 of the second pincer arm 515b" for deployment in tissue.

In some embodiments, the first pincer arm 515a, 515a', 515a" and/or the second pincer arm 515b, 515b', 515b" may be configured to be movable, so that the pincers 515 may have an open position and a closed position. The first and/or second pincer arms 515a, 515a', 515a", 515b, 515b', 515b" may open so that the distal ends 535a, 535a', 535a", 535b, 535b', 535b" may be positionable distally of the distal end 510 of the delivery catheter 500. The first connection point 525 at the proximal end of the first pincer arm 515a, 515a', 515a", and/or the second connection point 530 at the proximal end of the second pincer arm 515b, 515b', 515b" may be rotatable, so that the first and second pincer arms 515a, 515a', 515a", 515b, 515b', 515b" may be actuatable between an open position and a closed position. In embodiments, the first connection point 525 and the second connection point 530 may be disposed opposite of each other relative to the diameter of the delivery catheter 500, so that the distal ends 535a, 535a', 535a", 535b, 535b', 535b" of the first and second pincer arms 515a, 515a', 515a", 515b, 515b', 515b" may be mated to each other or positioned together when in a closed position, as described above with respect to the various embodiments.

FIG. 6 further illustrates at the distal end 510 of the delivery catheter a fixation device, or stabilizer 540. The stabilizer 540 may be helical in some embodiments, and may include a helical anchor. The stabilizer 540 may be disposed in a lower portion of the delivery catheter 500 (e.g., in the head 511, 511'), and may be extendable distally out of the distal end 510, described below. For example, the helical stabilizer 540 may be disposed below the horizontal axis 520 and disposed such that the helical stabilizer 540 does not impede movement of the first pincer arm 515a, 515a', 515a" and/or the second pincer arm 515b, 515b', 515b". In use, the helical stabilizer 540 may temporarily secure the delivery catheter 500 to tissue for delivery of an anchor 300, 400a-400h, although it is contemplated that a delivery catheter may be configured to secure to tissue or provide a stable platform for delivery of an anchor to the tissue without the use of a helical or other anchor for the catheter. In some embodiments, the fixation device may be an anchor, helix, barb, tine, t-bar, or combinations thereof, to bring the distal end 510 of the catheter 500 close to or in contact with annulus tissue.

A camera 545, a light 550, and/or sensors 555, 565 may also be disposed at the distal end 510 (e.g., the head 511, 511'), so that a user may see and verify an accurate location of the delivery catheter 500 for insertion of the anchors, e.g., anchors 300, 400a-400g. For example, the camera 545, light 550, and sensors 555, 565 may be disposed so that a surgical area distal of the distal end 510 of the delivery catheter 500 may be monitored by the camera 545, light 550, and/or sensors 555, 565. In some embodiments, the camera 545, light 550, and sensors 555, 565 may be disposed in an upper portion of the distal end 510 of the delivery catheter 500, e.g., above the horizontal axis 520, although they may be located anywhere at the distal end 510 of the delivery catheter 500 so long as the camera 545, light 550, and sensors 555, 565 do not impede movement of the first and second pincer arms 515a, 515a', 515a", 515b, 515b', 515b". The camera 545 may have a field of view of approximately 10 to 16 mm, so that a user may verify anchor placement (e.g., see FIGS. 11B, 12B, 13B, 15B, 19B, 20B, 21B, and 22B). The camera 545 may also allow for a user to differentiate between annulus tissue and atrium wall tissue, to help avoid incorrectly inserting the anchor. If an anchor is inserted in an incorrect position, e.g., too high, or in a leaflet, the valve may not be properly repaired, thereby allowing regurgitation to still occur. This may waste anchors and time for removal and reapplication. In some embodiments, the light 550 may be a LED light. In some embodiments, the sensors 555, 565 may be an ultrasonic sensor, and/or a degree-of-freedom (DOF) sensor. For example, the sensors 555, 565 may be an ultrasonic sensor having a five, or six degrees-of-freedom (DOF). The ultrasonic sensor 555 may be used to verify the delivery catheter 500 location and anchor placement may be determined by the user from the camera 545 and light 550. The DOF sensor 565 may be disposed in a lower portion of the distal end 510 of the delivery catheter 500, and may be used to sense the movement of the delivery catheter 500. In embodiments, the DOF sensor may be a 5 or 6 DOF navigation sensor. A port 560 may also be disposed at the distal end 510 of the delivery catheter 500, for delivering fluid to the surgical site. For example, the port 560 may deliver saline, to flush the desired area in preparation for anchor insertion. The port 560 may be disposed in an upper portion of the distal end 510 of the delivery catheter 500, although it may be located anywhere that does not impede movement of the first and second pincer arms 515a, 515a', 515a", 515b, 515b', 515b". In embodiments, a weeping saline balloon may be disposed at the distal end 510 of the delivery catheter 500 to clear any blood from the area for anchor insertion against tissue so that the user may have a clear view. In some embodiments, the distal end 510 of the delivery catheter 500 may include a balloon to assist in hydraulic crossing of the septal wall when inserting the catheter into the patient.

Any of the camera 545, light 550, sensors 555, 565, and port 560 may be controllable by a user of the delivery catheter 500, although in some embodiments, any of the components may be automatically actuated during a procedure as well. A balloon may aide direct visualization of cardiac structures, e.g., a valve, for the camera 545 and/or light 550 by surrounding the camera 545 and/or the light 550 with saline when the balloon is inflated. The saline-filled balloon may define a field of view and clear vision of the camera 545.

The distal end 510 of the delivery catheter 500 may include an anchor delivery mechanism 570 having a first curved plate 570a and a second curved plate 570b. For example, the first and second curved plates 570a, 570b may form a substantial portion of a circumference at a distal end and forming into an integral anchor delivery mechanism 570 at a proximal end (FIG. 8), thereby forming a cavity 575 in which components including but not limited to the first and second pincer arms 515a, 515a', 515a", 515b, 515b', 515b", helical stabilizer 540, camera 545, light 550, sensors 555, 565, and/or port 560 may be protected during insertion into a patient. For example, as described above, the distal end of the sheath 505a may be formed of a flexible material. The first and second curved plates 570a, 570b may be formed of a rigid material, e.g., metal, composite, or the like, to provide structural support to the distal end 510 of the delivery catheter 500. In this manner, the flexible distal end of the sheath 505a may be prevented from collapsing upon the components disposed in the cavity 575 at the distal end 510 of the delivery catheter 500 (e.g., any of the helical stabilizer 540, camera 545, light 550, sensors 555, 565, and/or port 560). It is understood that in some embodiments, the delivery catheter 500 as an alternative or in addition to the delivery mechanism 570 may include a head 511, 511'.

As described above, any of the first pincer arm 515a, 515a', 515a", and/or the second pincer arm 515b, 515b', 515b" may be configured to retract to an open position, as illustrated in FIGS. 5A-5C, 5E, and 7. The flexible distal end of the sheath 505a may similarly expand to accommodate the open position of the pincers 515. The first connection point 525 at the proximal end of the first pincer arm 515a, 515a', 515a" may be rotatable outward from the delivery catheter 500 in a direction indicated by arrow 580a about rotation axis 590a. The second connection point 530 at the proximal end of the second pincer arm 515b, 515b', 515b" may be rotatable outward from the delivery catheter 500 in a direction indicated by arrow 580b about rotation axis 590b. In embodiments, the rotation axes 590a, 590b may be substantially parallel to each other and perpendicular to a longitudinal axis 595.

Figure 8:
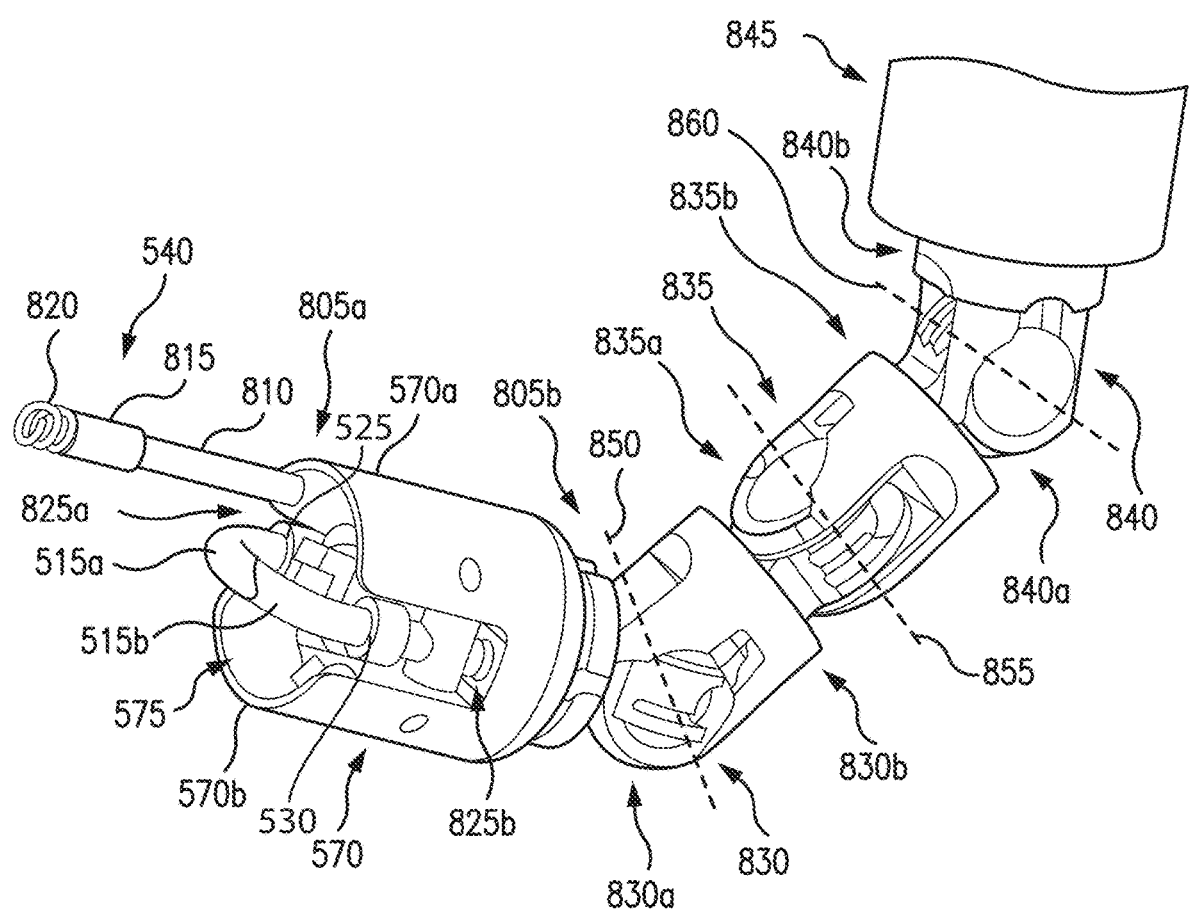
FIG. 8 illustrates a perspective view of an exemplary embodiment of an anchor delivery device in accordance with the present disclosure.
Figure 9:
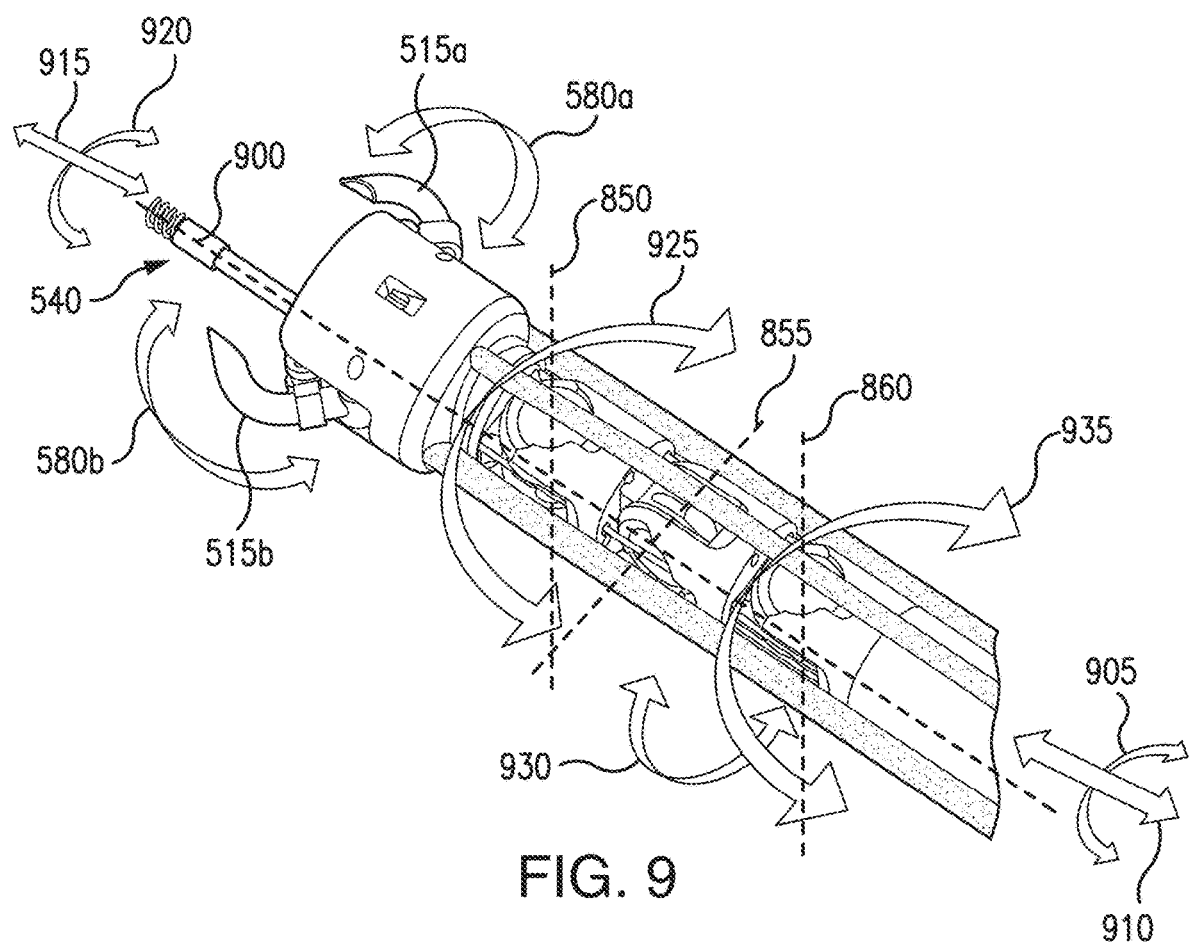
FIG. 9 illustrates another perspective view of an exemplary embodiment of an anchor delivery device in accordance with the present disclosure.
Figure 9C:
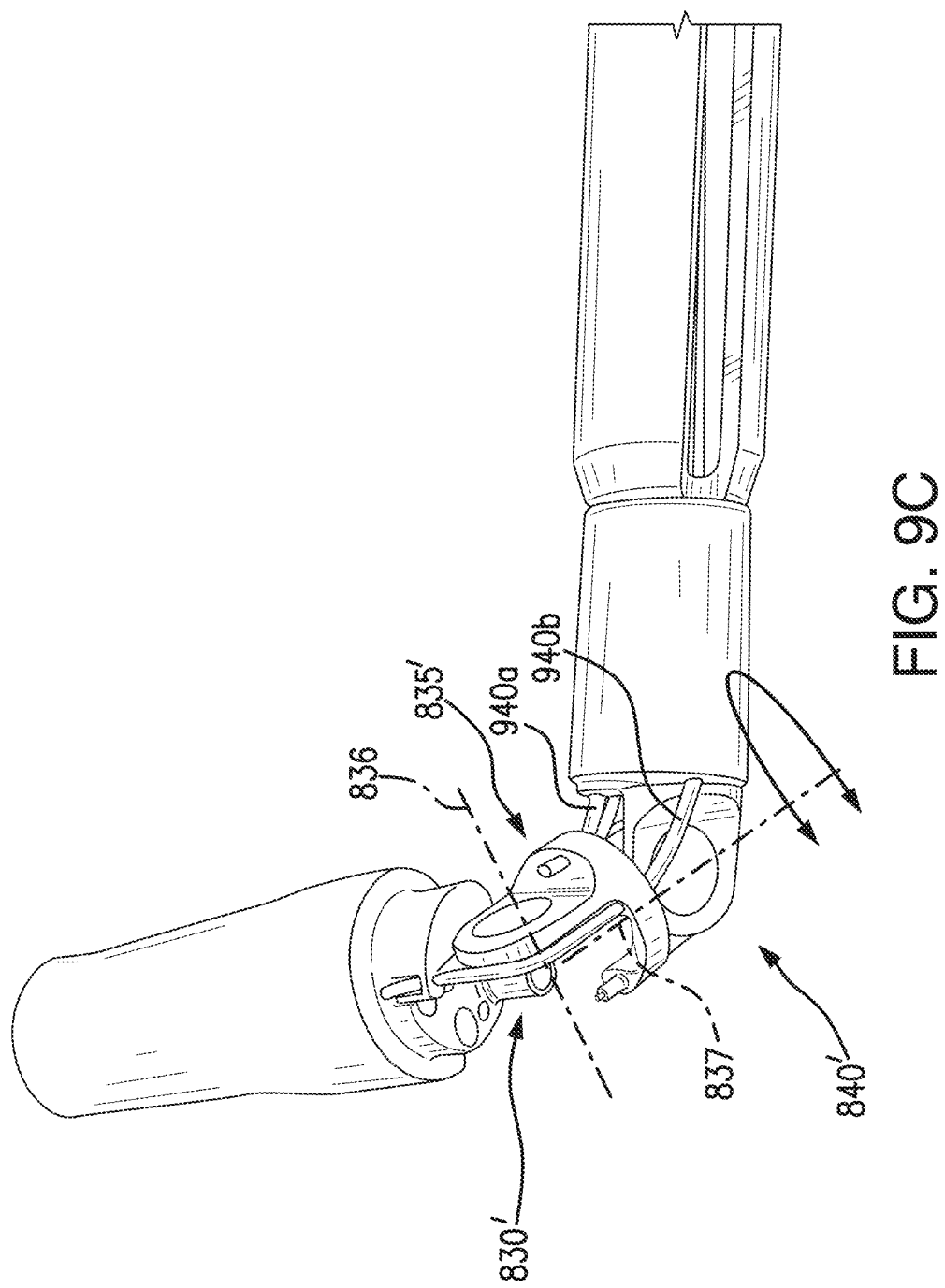
Figure 9D:
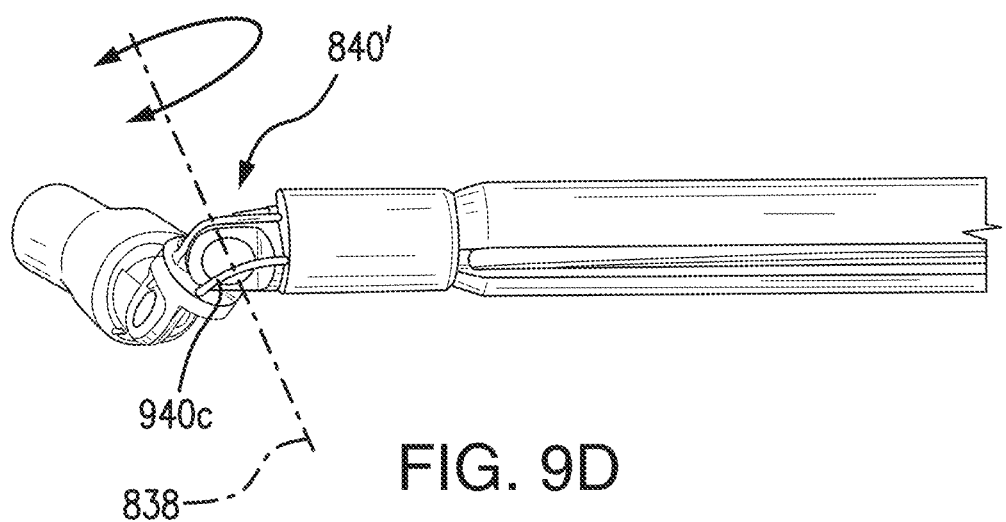

The delivery catheter 500 may be configured to include multiple joints for articulation, thereby resulting in several degrees of freedom of movement to allow for precise placement and alignment for anchor insertion around, e.g., the mitral and/or tricuspid valve. In some embodiments, a user may articulate the delivery catheter via a handle at a proximal end of the catheter for anchor delivery. Referring now to FIG. 8, the distal end 510 of the delivery catheter 500 without the sheath 505 is illustrated. As described above, the anchor delivery mechanism 570 may include a first curved plate 570a and a second curved plate 570b formed at a distal end 805a (e.g., head) of the anchor delivery mechanism 570, and may be integral at the proximal end 805b of the anchor delivery mechanism 570 at the first connection point 525 for the first pincer arm 515a, 515a', 515a" and the second connection point 530 for the second pincer arm 515b, 515b', 515b". The first and second curved plates 570a, 570b may be formed so that gaps 825a, 825b are formed to allow space for the first and second pincer arms 515a, 515a', 515a", 515b, 515b', 515b" to open (FIG. 8).

The helical stabilizer 540 may be extendable out of the cavity 575 formed from the first and second curved plates 570a, 570b of the anchor delivery mechanism 570. The helical stabilizer 540 may include an extension arm 810 and a connecting portion 815 at a distal end of the extension arm 810. The connecting portion 815 may couple a helical anchor 820 to the extension arm 810, so that the helical anchor 820 extends distally from the distal end 510 of the delivery catheter 500. The helical anchor 820 is configured to embed in tissue to stabilize the delivery catheter in a desired position for anchor insertion, described below.

The proximal end 805b of the anchor delivery mechanism 570 may be rotatably coupled to a first knuckle 830 at a distal end 830a of the first knuckle 830. The first knuckle 830 may be rotational about axis 850. In some embodiments, the first knuckle 830 may be rotational 360° around the axis 850, and in other embodiments may be at least partially rotational about the axis 850. For example, the first knuckle 830 may be configured as a u-joint, so that rotation may be at least 180°, or 270°. In some embodiments, the knuckles may be connected as ball and socket joints, for pivotal rotation. The distal end 510, or head 511, 511' may be connectable to a distal end 830a of the first knuckle 830. A proximal end 830b of the first knuckle 830 may be rotatably coupled to a distal end 835a of a second knuckle 835. The second knuckle 835 may be rotational about axis 855. In some embodiments, the second knuckle 835 may be rotational 360° around the axis 855, and in other embodiments may be at least partially rotational about the axis 855. For example, the second knuckle 835 may be configured as a u-joint, so that rotation may be at least 180°, or 270°. A proximal end 835b of the second knuckle 835 may be rotatably coupled to a distal end 840a of a third knuckle 840. The third knuckle 840 may be rotational about axis 860. In some embodiments, the third knuckle 840 may be rotational 360° around the axis 860, and in other embodiments may be at least partially rotational about the axis 860. For example, the third knuckle 840 may be configured as a u-joint, so that rotation may be at least 180°, or 270°. A proximal end 840b of the third knuckle 840 may be coupled to a stationary portion 845 of the delivery catheter 500. The rotational axis 850 of the first knuckle 830 may be substantially perpendicular to the rotational axis 855 of the second knuckle 835, so that that the first, second, and third knuckles 830, 835, 840 may form an articulable distal end of the delivery catheter. The rotational axis 855 of the second knuckle 835 may be substantially perpendicular to the rotational axis 860 of the third knuckle 840, so that the knuckles 835, 840 form an articulable distal end of the delivery catheter. In some embodiments, the rotational axes 850, 860 may be substantially parallel to each other. In embodiments, the first, second, and third knuckles 830, 835, 840 may be successive u-joints to allow for rotation. Although a first, second and third knuckle 830, 835, and 840 are illustrated, it is understood that the delivery catheter 500 may include more or less knuckles to achieve a desired articulation. In some embodiments, the delivery catheter 500 may have three knuckles for having several degrees of freedom so that the delivery catheter 500 may have full access to the valve and an area surrounding the valve. The first, second, and third knuckles 830, 835, 840 may be coupled in a row to form an articulable distal end 510 of the delivery catheter 500. In some embodiments, at least one of the first, second, and third knuckles 830, 835, 840 may be lockable, to hold a position set by a user. The first, second, and third knuckles 830, 835, 840 may be lockable via a respective cable lead or leads coupled to a handle disposed at a proximal end of the delivery catheter 500, to locally hold a position set by the user. For example, the user may manipulate and lock any of the first, second, and third knuckles 830, 835, 840 locally at the handle via the cable leads.

As shown in FIGS. 8A-8B, in some embodiments, the delivery catheter 500 may include one or more knuckles 830', 835', 840'. The knuckles 830', 835', 840' may be formed of substantially planar plates perpendicular to each other, and connectable as ball and socket joints for pivotal rotation. For example, knuckle 835' may include a first plate 831 extending in a first plane relative to the axis 595, a second plate 832 extending in a second plane relative to the axis 595 and substantially perpendicular to the first plate 831, and a third plate 833 extending in a third plane relative to the axis 595 and substantially perpendicular to the first plate 831 and the second plate 832. In embodiments, the knuckles 830', 835' may be formed identically and positionable opposite of each other, so that plate 833 and plate 833' are connectable to each other to pivotably join knuckles 830' and 835'. The knuckles 830', 835', 840' may be connectable by a button 834, to pivotably rotate with respect to each other. As shown in FIG. 8A, the head (see FIGS. 5, 5A-5F, 6-8) may be connectable and rotatable relative to the knuckle 830' about axis 836, knuckles 830', 835' may be rotatable with respect to each other about axis 837 as shown by arrow 837', and the knuckles 835', 840' may be rotatable with respect to each other about axis 838 as shown by arrow 838'. Although knuckles 835', 840' are illustrated, it is understood that any number of knuckles positionable opposite each other may be pivotably coupled to form a distal end of a delivery catheter. It is understood that the knuckles as assembled together may be constrained. For example, the knuckle 835' may be rotatable only to the extent permitted by knuckle 835' and 840' connected at each end. In some embodiments, the distal end 510, or head 511, 511', of the delivery catheter may be actuatable while maintaining a desired coordinate position. For example, first and second pincer arms 515a, 515a', 515a", 515b, 515b', 515b" may be oriented for plication without changing the position of the distal end 510 of the delivery catheter 500.

The multiple rotational axes 850, 855, 860, 900, and/or 836, 837, 838 may allow for several degrees of movement of the distal end 510 of the delivery catheter 500 as shown in FIGS. 9 and 9A-9D, and charted in FIG. 10. In some embodiments, the delivery catheter 500 may have up to nine degrees of freedom. For example, the delivery catheter 500 may be translatable along longitudinal axis 900 in the direction of arrow 910, for insertion into the patient to access the mitral and/or tricuspid valve. In embodiments, longitudinal axis 900 may be coaxial to axis 595, and in other embodiments, longitudinal axis 900 may be substantially parallel to axis 595. Additionally, the delivery catheter 500 may be rotatable about longitudinal axis 900 in a direction indicated by arrow 905.

The helical stabilizer 540 may be translatable along the longitudinal axis 900 in the direction of arrow 915, to embed or anchor into tissue to stabilize the delivery catheter 500 for anchor delivery as discussed above. The helical stabilizer 540 may also be rotatable about longitudinal axis 900 indicated by arrow 920. For example, the helical stabilizer 540 may be rotatable so that the helical anchor 820 (FIG. 8) may be embedded, or anchored, into tissue near the mitral and/or tricuspid valve.

As described above, the first pincer arm 515a, 515a', 515a" may be rotatable in a direction of arrow 580a, and the second pincer arm 515b, 515b', 515b" may be rotatable in a direction of arrow 580b. As illustrated, the first and second pincer arms 515a, 515a', 515a", 515b, 515b', 515b" may open outward from the delivery catheter 500. In some embodiments, the second pincer arm 515b" may remain substantially stationary for at least a portion of the anchor delivery process, while the first pincer arm 515a" rotates between an open and a closed position (see FIGS. 5E-5F). The second pincer arm 515b" may be configured to rotate as described above for at least another portion of the anchor delivery process. An open position may allow for clearance to position the delivery catheter 500 in the desired location of the annulus of the mitral and/or tricuspid valve for anchor delivery. It is understood that other dimensions, loads, distances, performance requirements or tolerances, etc., may be suitable for other applications.

The first knuckle 830 may be rotatable about axis 850, in a direction indicated by arrow 925. The second knuckle 835 may be rotatable about axis 855, in a direction indicated by arrow 930. The third knuckle 840 may be rotatable about axis 860, in a direction indicated by arrow 935. As illustrated, the first, second, and third knuckles 830, 835, and 840 may be rotatably coupled in a manner to have multiple degrees of freedom, thereby allowing an articulation of the distal end 510 of the delivery catheter 500. For example, axis 850 may be substantially perpendicular to axis 855, and axis 855 may be substantially perpendicular to axis 860.

As shown in FIGS. 9 and 9A-9D, a delivery catheter may be positionable by the knuckles 830, 830', 835, 835', 840, 840', and a cable system 940. In embodiments, the distal end of the delivery catheter may be navigated by the cable system and knuckles, so the delivery catheter may have omni-directional steering at the distal end. For example, the distal end 510 may be positionable directly over an annulus for deployment of a series of anchors 300, 400a-400h. The knuckles may provide for fine navigation and control so that the catheter may not damage (e.g., bruise, stress, and/or abrade) tissue during positioning. Known push catheters may deflect off an atrium, which may later contribute to a development of atrial fibrillation. The present disclosure may minimize or avoid long-term damage in patients by self-positioning the distal end of the delivery catheter by the knuckles and the cable system. In embodiments, the system may include a plurality of cables extending from a proximal end of the delivery catheter to the knuckles, e.g., approximately 6-12 cables, and may each be operable by a motor disposed at a proximal end of the delivery catheter and controllable by a medical professional. Cables may be formed of a metal, or polymer, or both, or braided metal or polymer, or both.

In embodiments, the distal end 510 of the delivery catheter may be translatable and/or rotatable for positioning prior to deploying an anchor 300, 400a-400h in annulus tissue. When the delivery catheter is navigated to the desired position, the cables may be driven by one or more motors, such that to rotate the distal end in a desired direction, a cable may require a predetermined force to flex a ball and socket joint connecting the knuckles. For example, up to 15 lbs of force may be necessary to flex the first knuckle 830' by a first cable 940a, e.g., about axis 836 to turn the head at the distal end of the delivery catheter (see FIG. 9B). The delivery catheter may hold this first flexed position prior to moving the second knuckle. In some embodiments, the tension in the first cable 940a may be minimized, or zeroed out. The second ball and socket joint connecting the knuckles may require approximately 8 to 20 lbs to flex. For example, the second knuckle 835' may be flexed by a second cable 940b, e.g., about axis 837 (see FIG. 9C). The delivery catheter may hold this second position by stopping the respective motor, and may minimize, or zero out, the tension in the second cable 940b. The third knuckle 840' may flex about axis 838 in the same manner, e.g., by a third cable 940c, after which the respective motor may stop to hold the delivery catheter in position to minimize, or zero out, the tension in the third cable 940c. It is understood that additional knuckles and cables may similarly flex and minimize, or zero out, tension for positioning of the distal end of the delivery catheter to a desired location. In this manner, the delivery catheter may remain flexible during navigation to the desired position with respect to the annulus, including actuating, or rotating, pincer arms to the desired position for tissue plication, with minimized or no residual forces, thereby minimizing potential bruising, tearing, or other damage of the atrium.

Figure 22A:
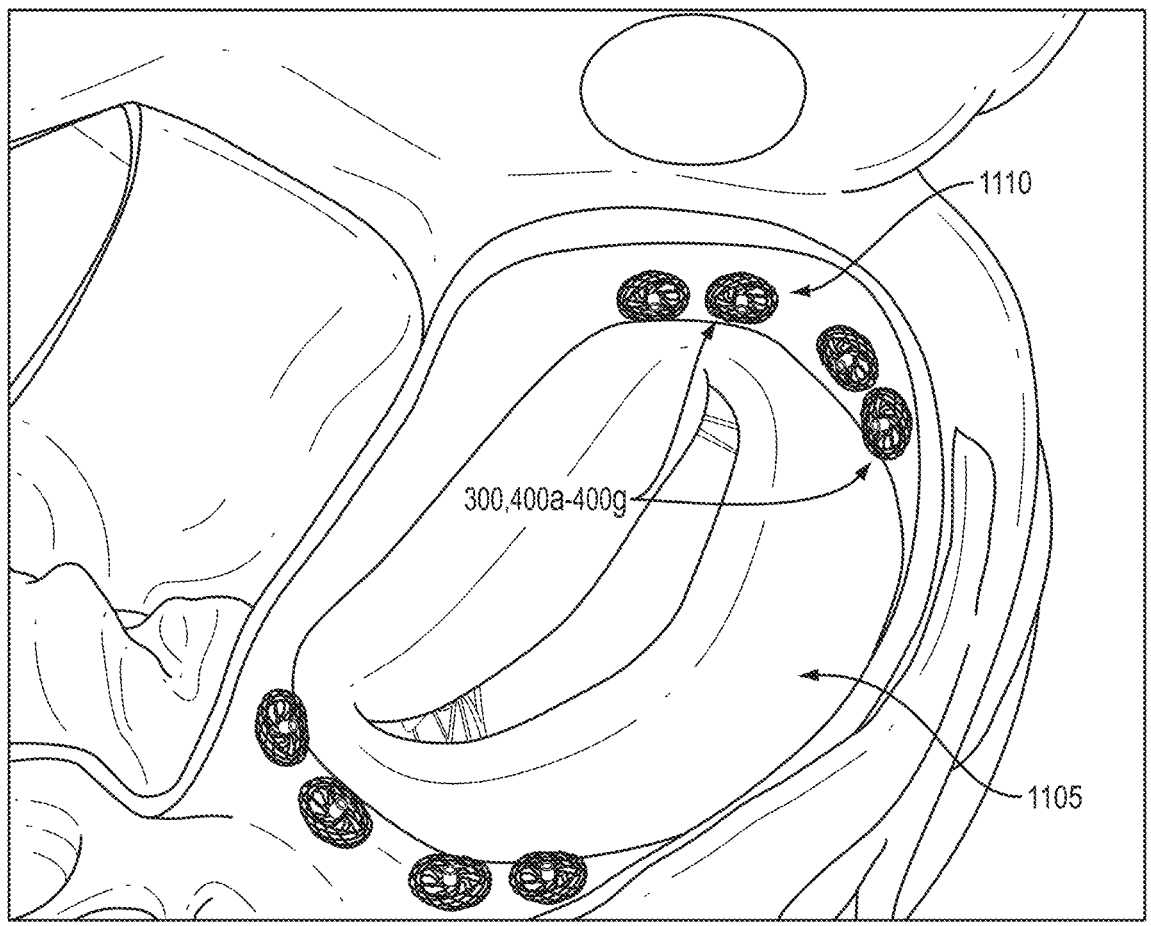
FIGS. 22A-22B illustrate an exemplary embodiment of an anchor delivery method of additional anchor placement in accordance with the present disclosure.
Figure 22B:
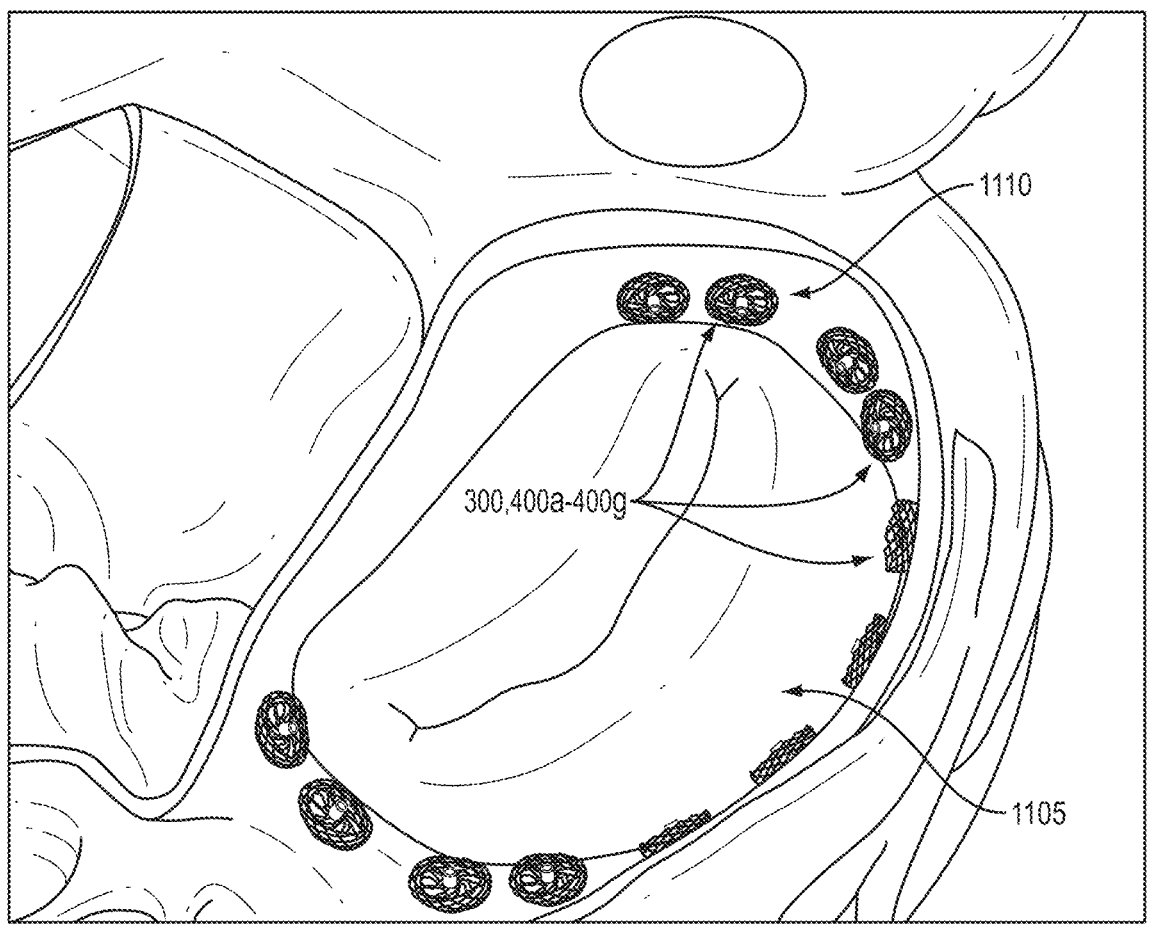
Figure 23:
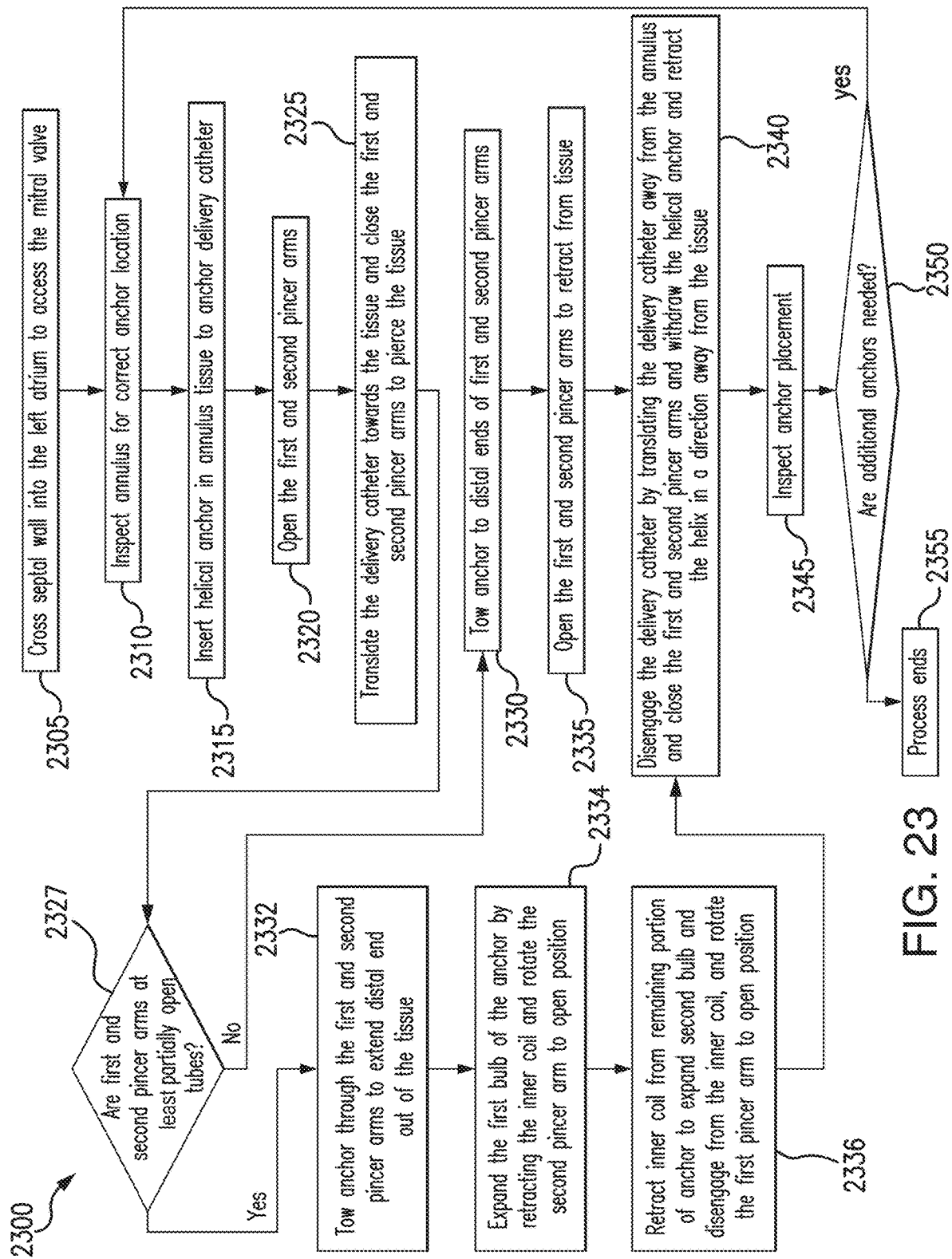
FIG. 23 is a flow chart illustrating an exemplary embodiment of an anchor delivery method in accordance with the present disclosure.

Referring now to FIGS. 11A-22B, an exemplary embodiment of a method for delivering one or more anchors to an annulus of a mitral and/or tricuspid valve in accordance with the present disclosure is illustrated, and FIG. 23 shows flowchart 2300 for exemplary processes. Although a valve 1105 is shown as a mitral valve, it is understood that the method may be used for a mitral/bicuspid valve and a tricuspid valve. To access the heart of a patient, intravenous access may be established through the femoral vein, and the delivery catheter 500 may be advanced to the right atrium of the patient's heart. The distal end 510 of the delivery catheter 500 may cross the atrial septal wall into the left atrium to access the valve 1105 at step 2305, and shown in FIGS. 11A-11B. FIG. 11B is a perspective view of the valve 1105 from the distal end 510 of the delivery catheter 500, e.g., via the camera 545. The distal ends 535a, 535a', 535a", 535b, 535b', 535b" of the first and second pincer arms 515a, 515a', 515a", 515b, 515b', 515b" may be mated together, or in proximity to each other in a closed position as described above with respect to the various embodiments (see FIGS. 5, 5A-5F) as the delivery catheter 500 is positioned at the valve 1105. Although the valve 1105 is shown and described in the present embodiment, it is understood that the delivery catheter 500 may also access the tricuspid valve in a similar manner.

Figure 12A:
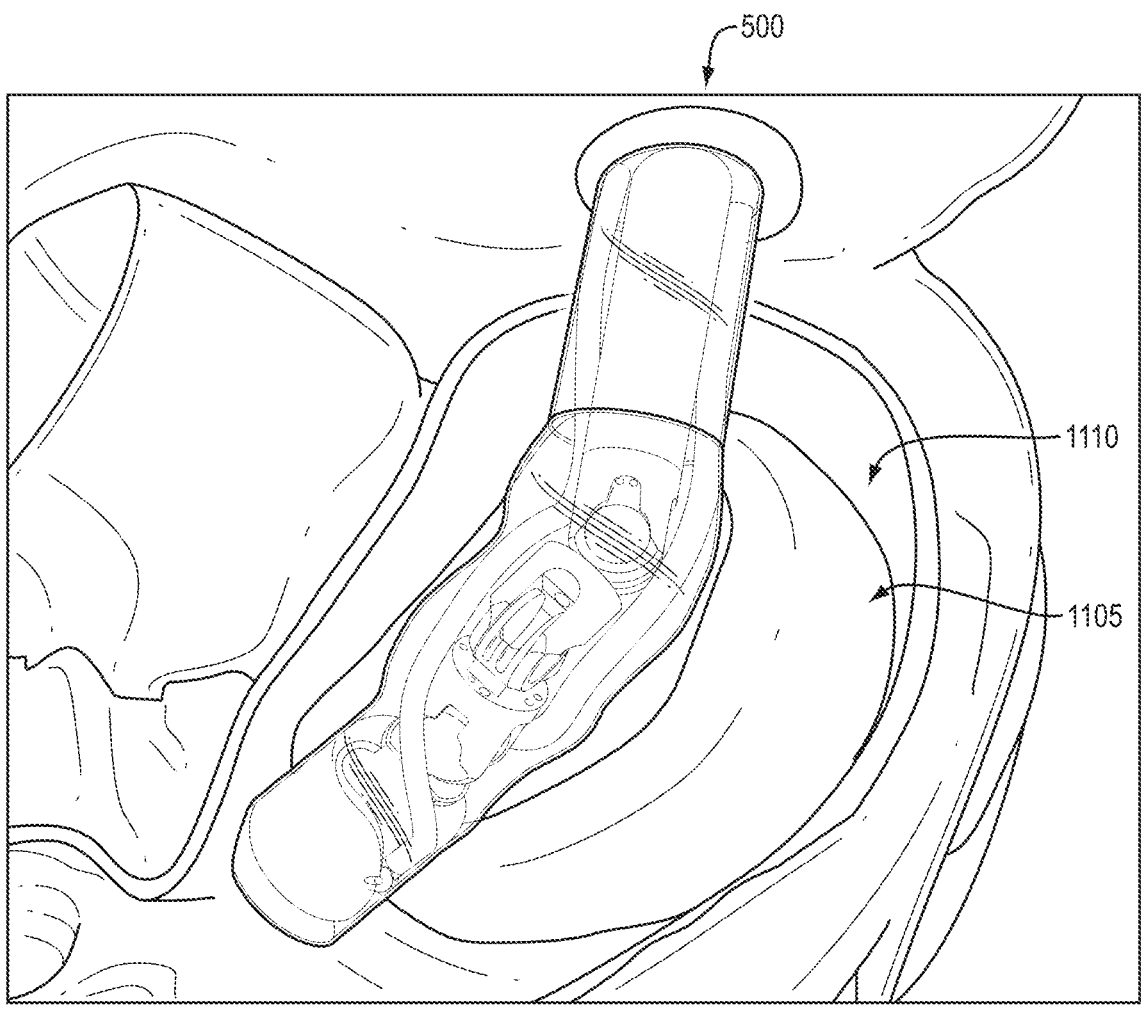
FIGS. 12A-12B illustrate an exemplary embodiment of an anchor delivery method of determining an anchor position to a valve by an anchor delivery catheter in accordance with the present disclosure.
Figure 12B:
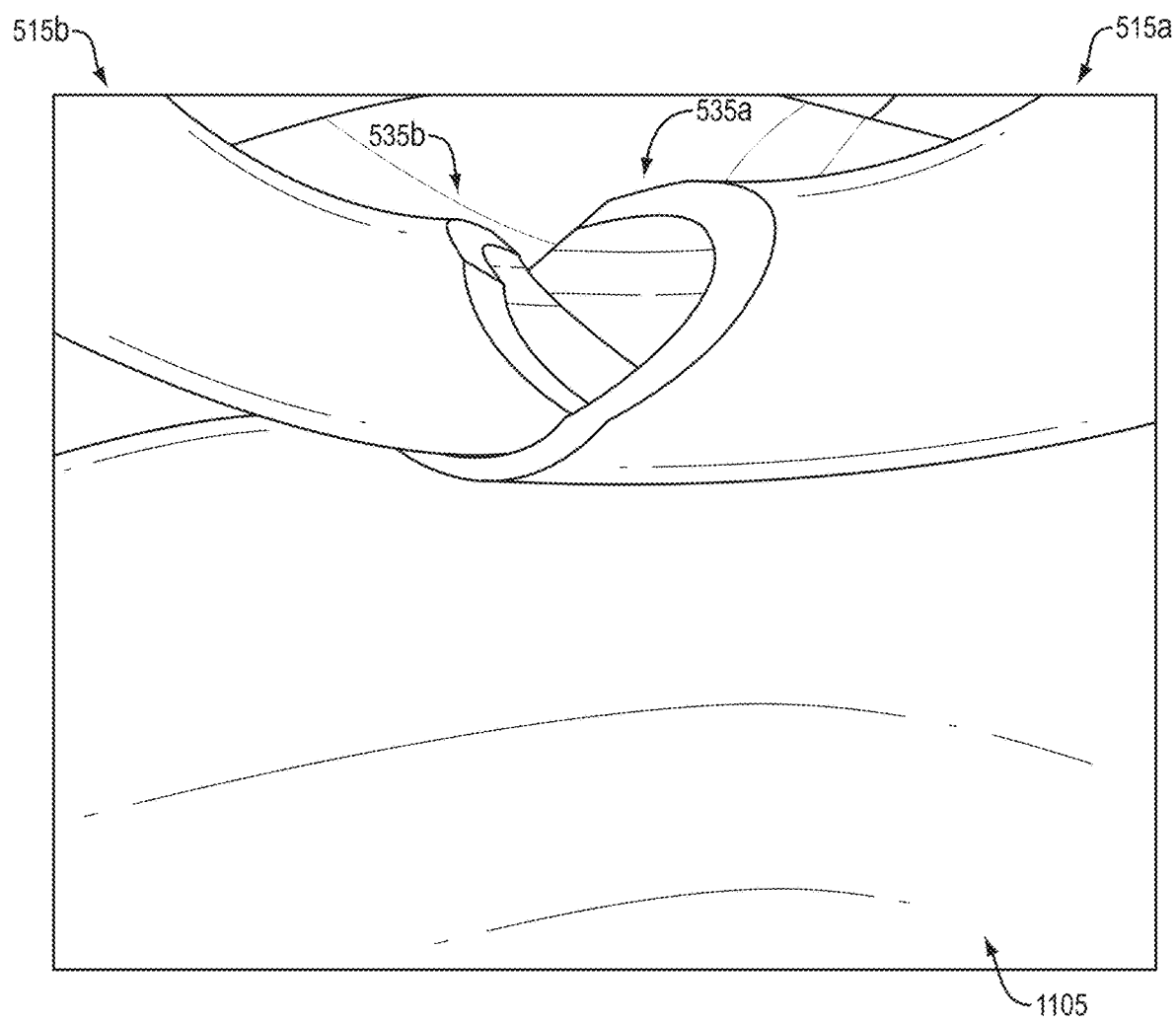

Once the valve 1105 is accessed by the distal end 510 of the delivery catheter 500, one or more locations may be inspected to determine the proper location for anchor delivery at step 2310 and illustrated in FIGS. 12A-12B. The camera 545 and light 550 may be utilized by a user to visualize the valve 1105 and annulus 1110, to inspect and determine the desired location to insert an anchor 300, 400a-400h. For example, it may be advantageous to insert a first anchor 300, 400a-400h in the annulus 1110 adjacent to the fibrous trigone, near an A1-P1 leaflet commissure of the valve 1105, e.g., where the anterior leaflet and the posterior leaflet are joined. As illustrated by FIGS. 9A-9D, the delivery catheter has omnidirectional steering capabilities and may be positionable by the knuckles 830, 830', 835, 835', 840, 840' and/or the cables 940 and by shifting and/or minimizing, or zeroing out, tension in cables after rotation of the respective knuckles to minimize potential tissue damage.

Figure 13A:
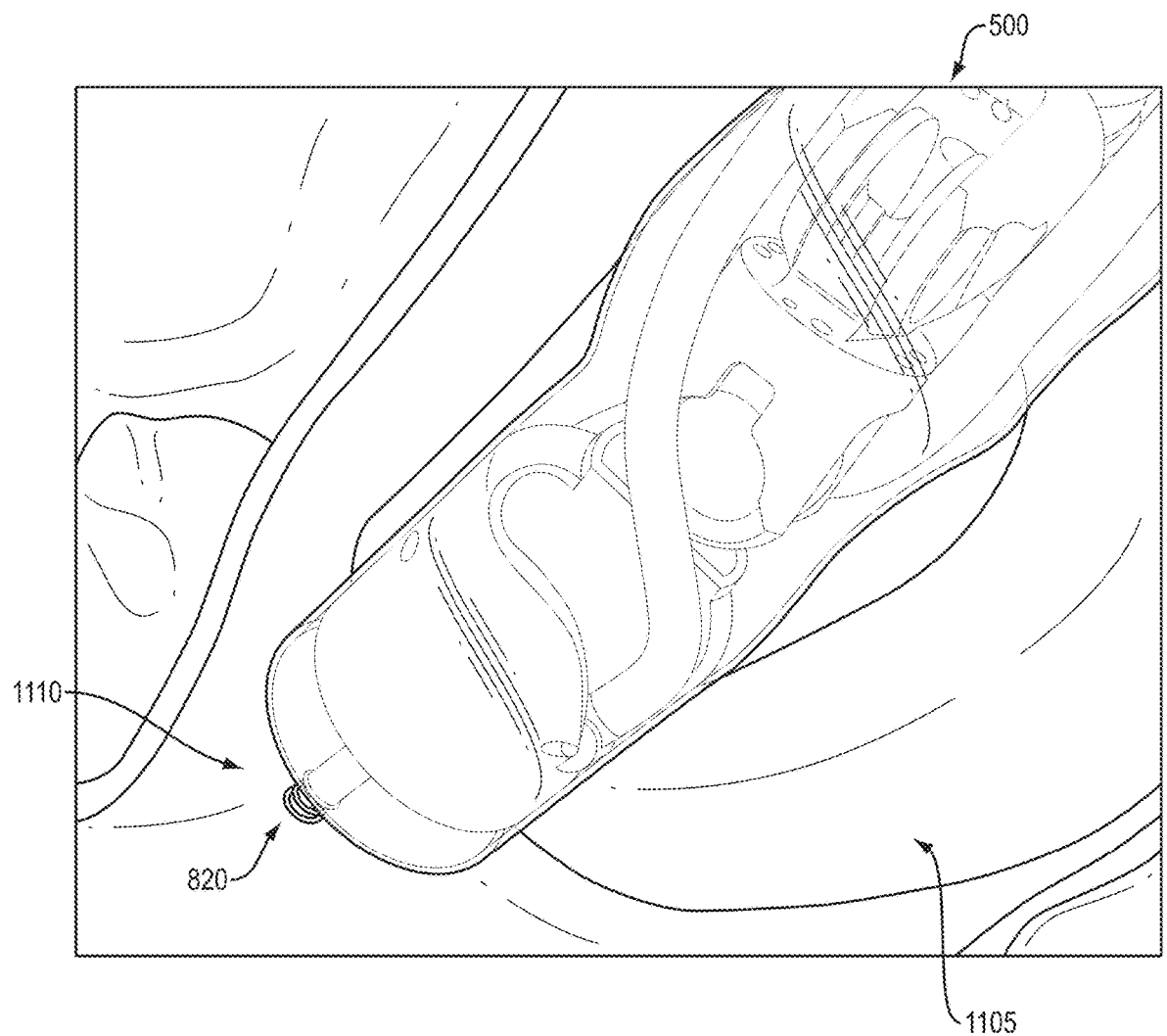
FIGS. 13A-13B illustrate an exemplary embodiment of an anchor delivery method of anchoring an anchor delivery catheter at a valve in accordance with the present disclosure.
Figure 13B:
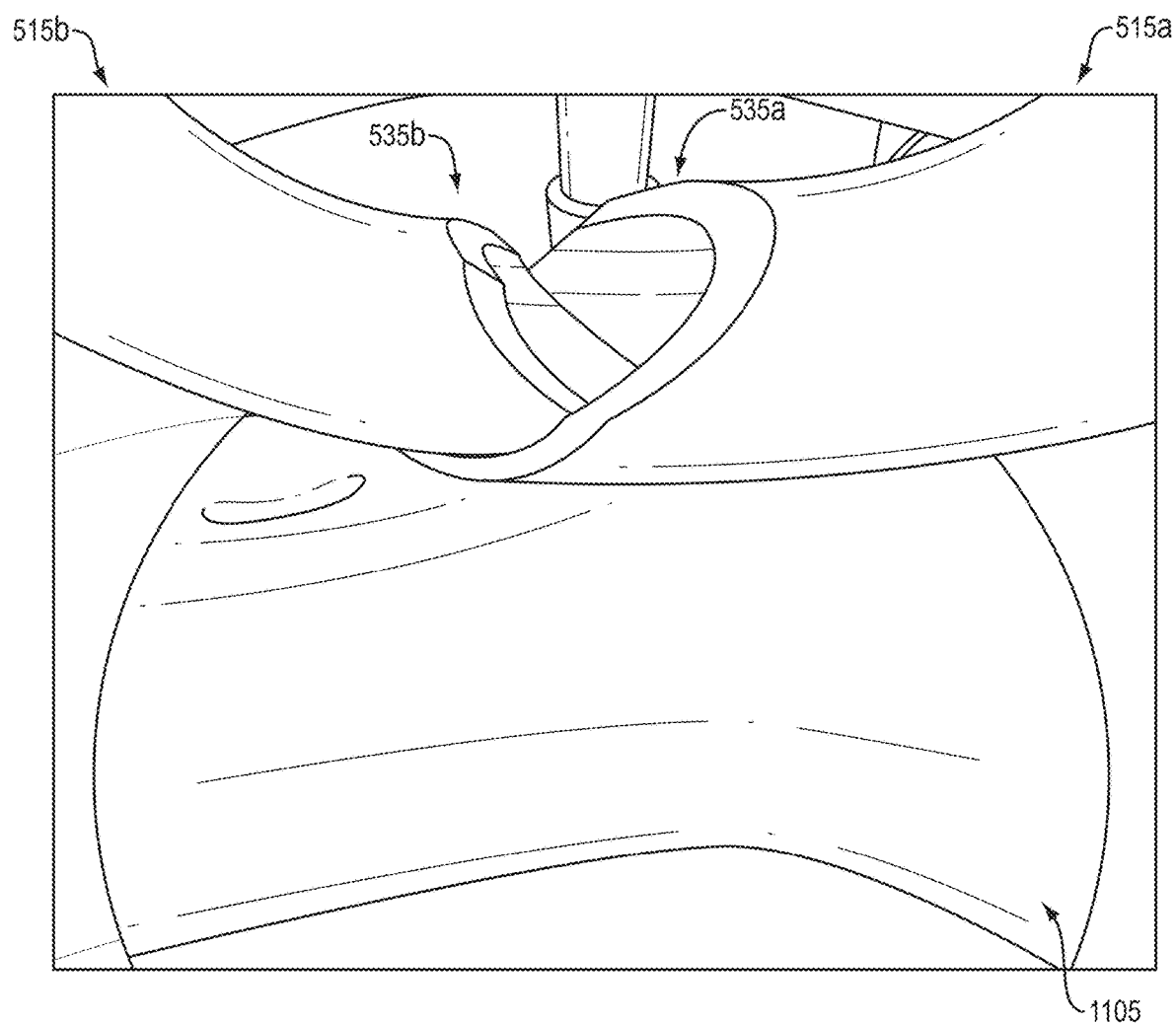
Figure 14A:
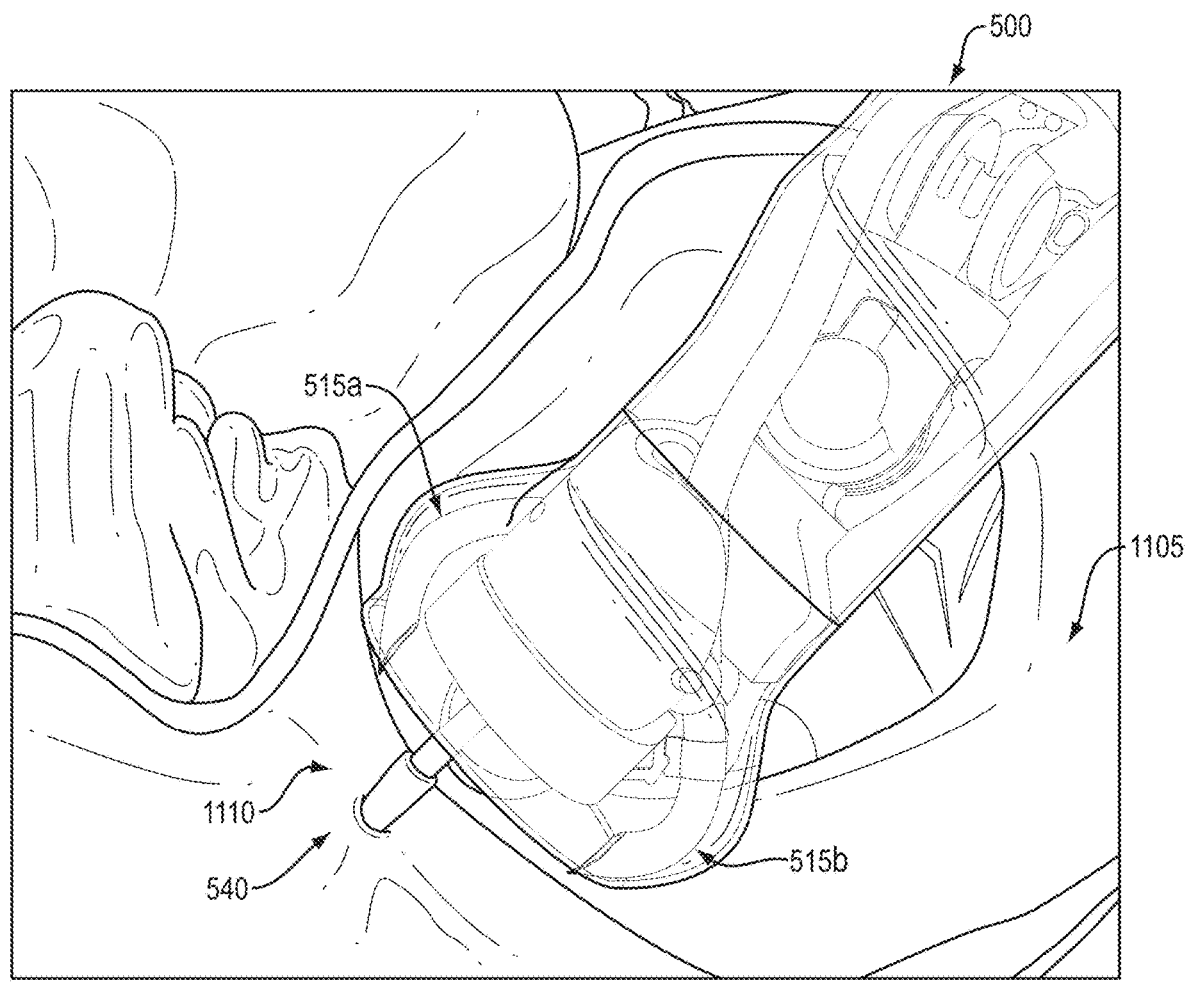
FIGS. 14A-14B illustrate an exemplary embodiment of an anchor delivery method of opening pincer arms of an anchor delivery catheter in accordance with the present disclosure.
Figure 14B:
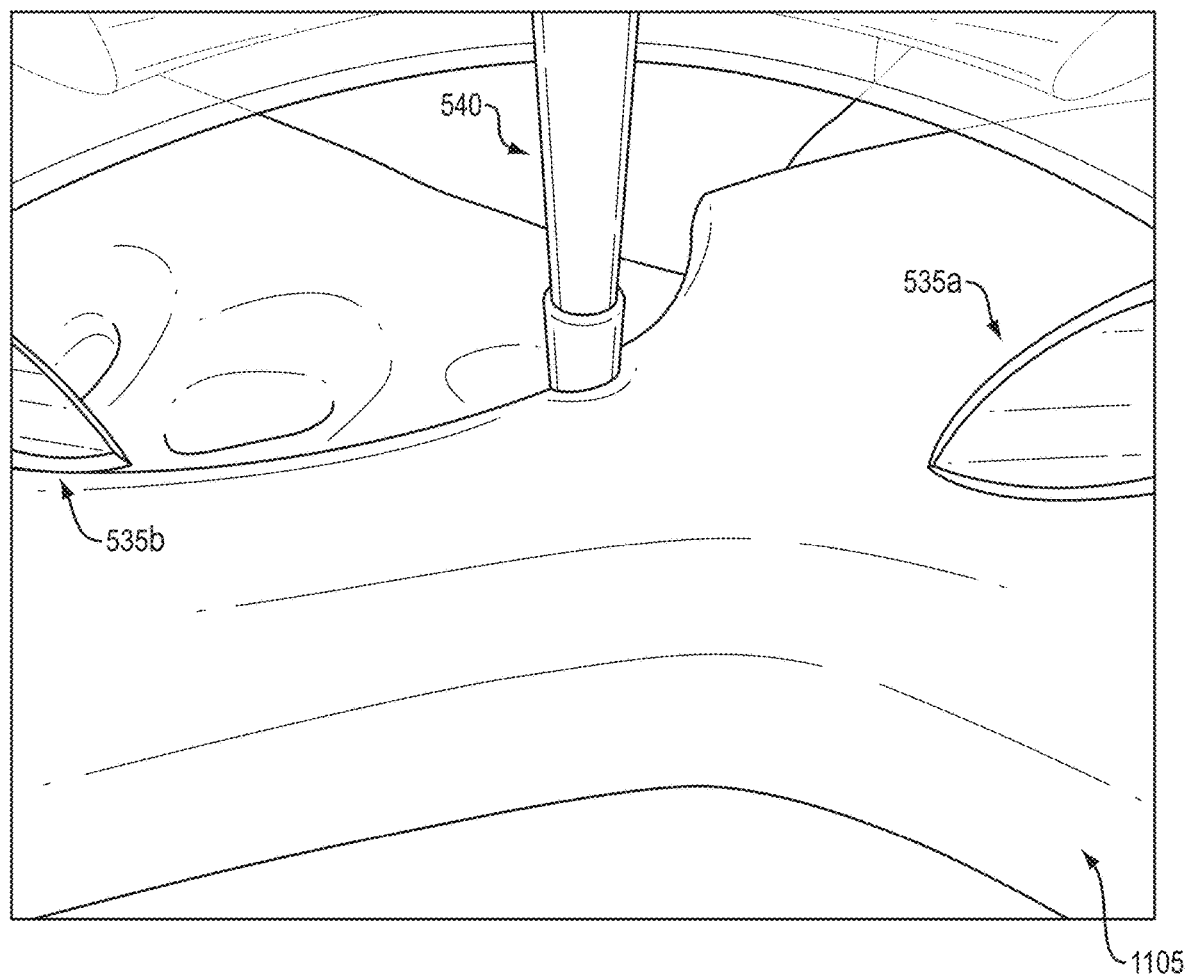

When the A1-P1 position has been located and the distal end 510 of the delivery catheter 500 has been positioned, the helical anchor 820 may be embedded, or anchored, into tissue of the annulus 1110 at step 2315 and as shown in FIGS. 13A-13B. The helical anchor 820 may be fully embedded in the tissue of the annulus 1110 to stabilize the delivery catheter 500 via the helical stabilizer 540 during anchor insertion. When the helical anchor 820 is embedded in the annulus 1110 and the helical stabilizer 540 is stabilizing the delivery catheter 500 to prevent unintentional movement from the desired anchor insertion location (e.g., the A1-P1 location), at step 2320 and shown in FIGS.

14A-14B, the first and second pincer arms 515*a*, 515*a*', 515*a*", 515*b*, 515*b*', 515*b*" may be actuated, or rotated, to an open position.

Figure 15:
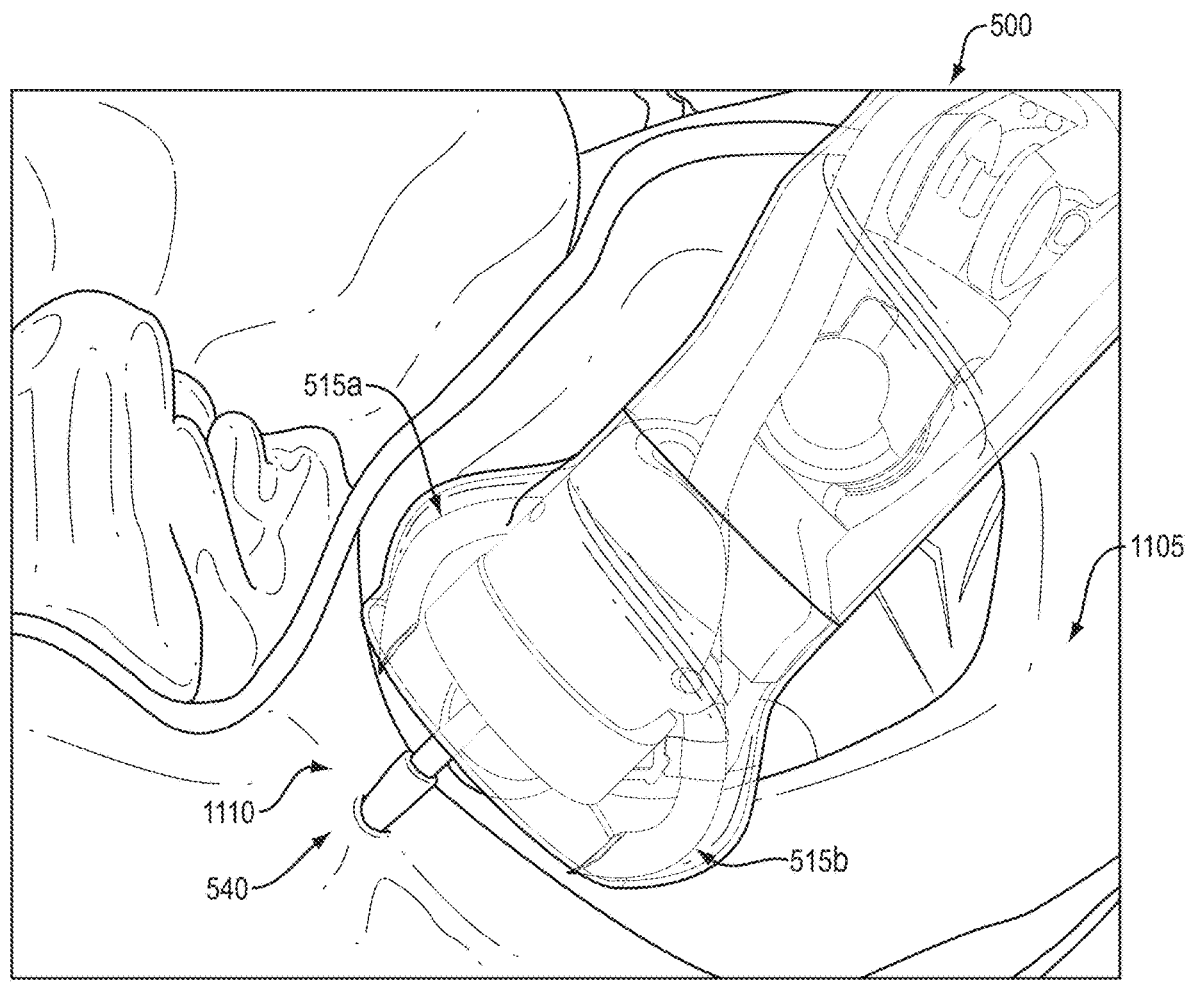
FIGS. 15-17 illustrate an exemplary embodiment of an anchor delivery method of in accordance with the present disclosure.
Figure 16:
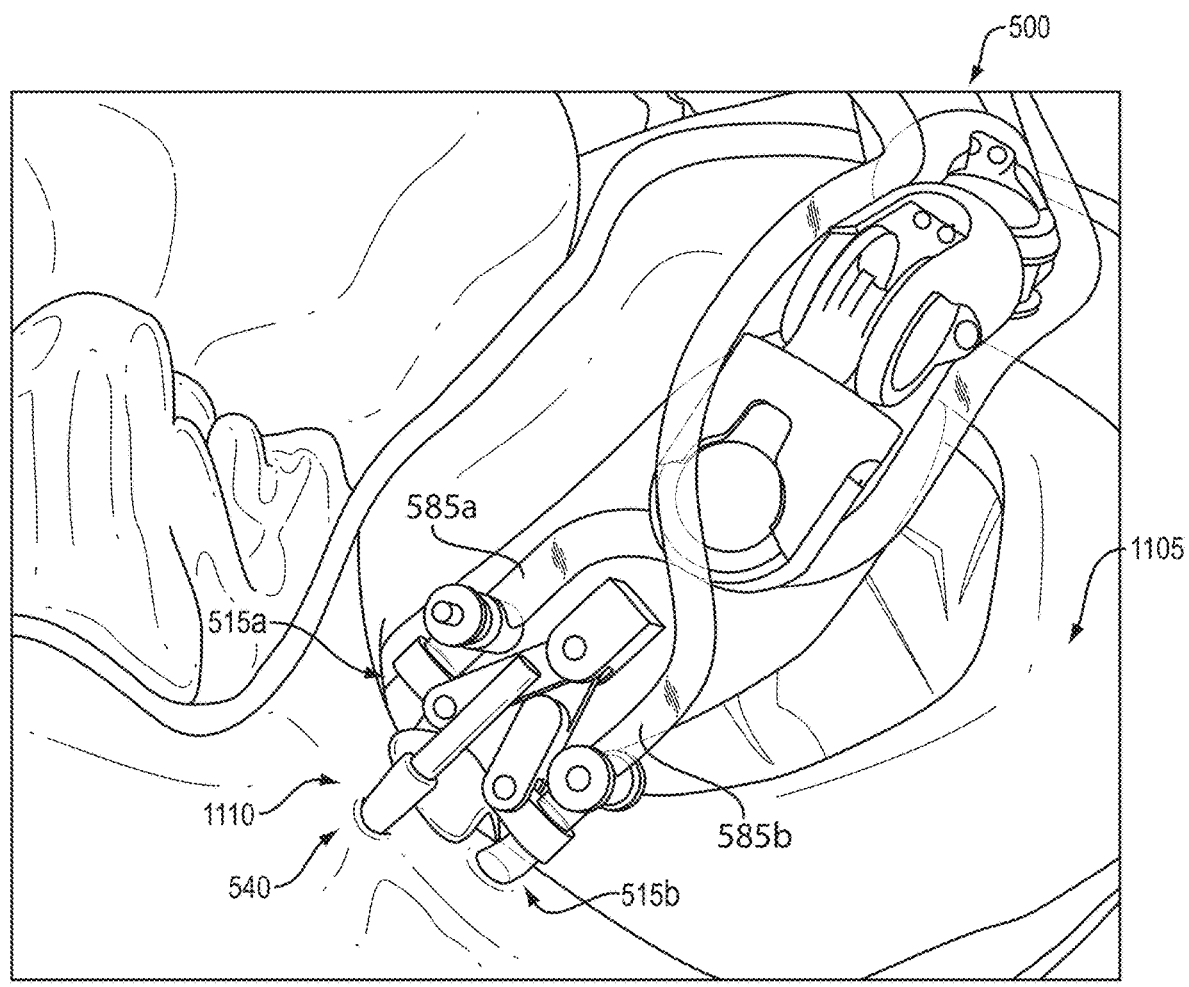

When the first and second pincer arms 515*a*, 515*a*', 515*a*", 515*b*, 515*b*', 515*b*" are in an open position, the delivery catheter 500 may be translated in a direction towards the annulus, and the first and second pincer arms 515*a*, 515*a*', 515*a*", 515*b*, 515*b*', 515*b*" may be closed, thereby piercing, or plicating, tissue, e.g., the annulus, by the distal ends 535*a*, 535*a*', 535*a*", 535*b*, 535*b*', 535*b*" of the respective first and second pincer arms 515*a*, 515*a*', 515*a*", 515*b*, 515*b*', 515*b*" at step 2325 and shown in FIGS. 15-16. The distal ends 535*a*, 535*a*', 535*a*", 535*b*, 535*b*', 535*b*" of the respective first and second pincer arms 515*a*, 515*a*', 515*a*", 515*b*, 515*b*', 515*b*" may be sharp points to ensure piercing of the tissue. When the first and second pincer arms 515*a*, 515*a*', 515*a*", 515*b*, 515*b*', 515*b*" are actuated back to the closed position within the annulus tissue, the respective distal ends 535*a*, 535*a*', 535*a*", 535*b*, 535*b*', 535*b*" may once again mate with each other. FIG. 16 shows a portion of the delivery catheter 500, without the sheath 505 and first and second curved plates 570*a*, 570*b* in order to illustrate the first and second pincer arms 515*a*, 515*a*', 515*a*", 515*b*, 515*b*', 515*b*" closed within the annulus 1110. The actuation of the first and second pincer arms 515*a*, 515*a*', 515*a*", 515*b*, 515*b*', 515*b*" may ensure that anchor placement manages tissue depth and a length of tissue captured so as to be repeatable for a plurality of anchor insertions.

At step 2327, the process may vary depending on the configuration of the delivery catheter. For example, as described above, if the first and second pincer arms 515*a*, 515*b*, are hollow tubes which are not at least partially open, for example, as shown in FIGS. 5 and 6-8, then the process may continue to step 2330. If the first and second pincer arms 515*a*', 515*a*", 515*b*', 515*b*" as formed as at least partially open tubes, for example, as shown in FIGS. 5A-5F, then the process may continue to step 2332.

At step 2330 and shown in FIG. 17, an anchor, e.g., anchor 300, 400*a*-400*h* may be towed to the first and second pincer arms 515*a*, 515*a*', 515*a*", 515*b*, 515*b*', 515*b*" via the anchor delivery tubes 585*a*, 585*b*. In some embodiments, the anchor 300, 400*a*-400*h* may be towed through via a suture or stylet. As described above, the first and second pincer arms 515*a*, 515*b* may be hollow tubes so that an anchor may be delivered to the distal ends 535*a*, 535*b*, of the first and second pincer arms 515*a*, 515*b*, for insertion into the annulus. In some embodiments, the first and second pincer arms 515*a*', 515*a*", 515*b*', 515*b*" may be at least partially open, for example, formed as a pass-through needle and a side shooter passage (see FIGS. 5A-5F). In some embodiments, due to the mating, or positioning, of the distal ends of the first and second pincer arms 515*a*, 515*b*, the anchor 300, 400*a*-400*h* may be positioned in both the first and second pincer arms 515*a*, 515*b*, while the arms are in the closed position. Any of the anchors 300, 400*a*-400*h* described above may be used for insertion in the delivery catheter 500.

Figure 18A:
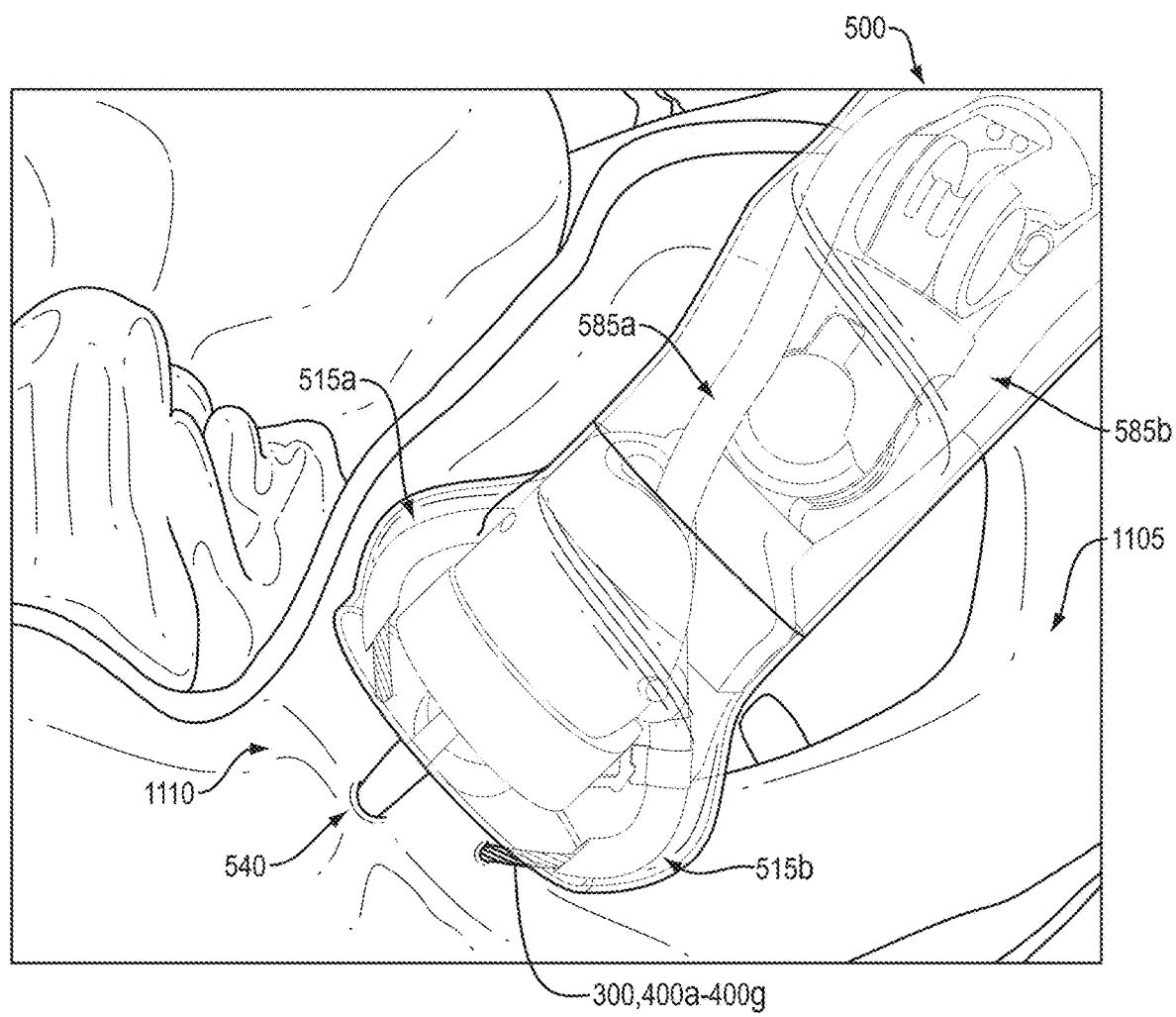
FIGS. 18A-18B illustrate an exemplary embodiment of an anchor delivery method of retracting pincer arms in accordance with the present disclosure.
Figure 18B:
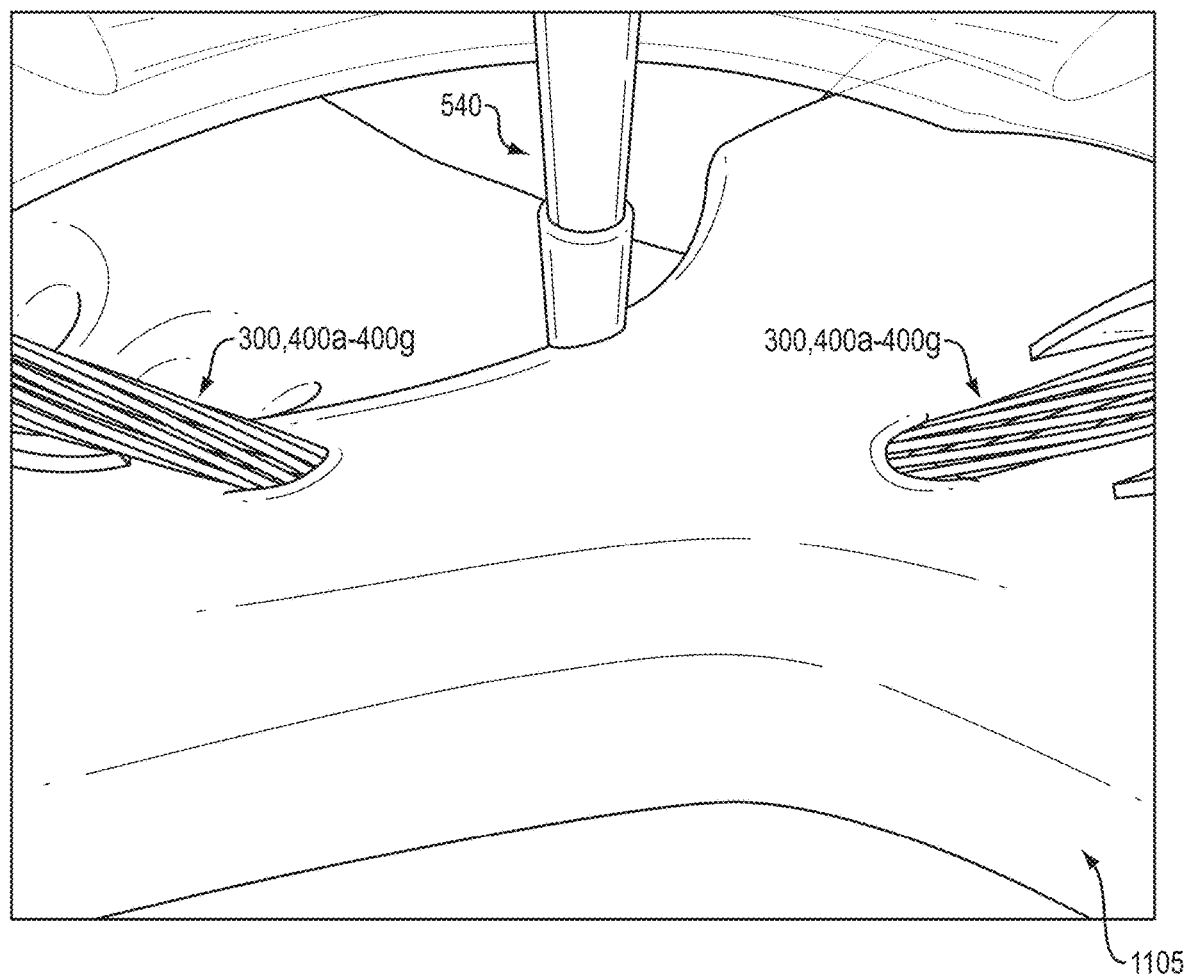
Figure 19A:
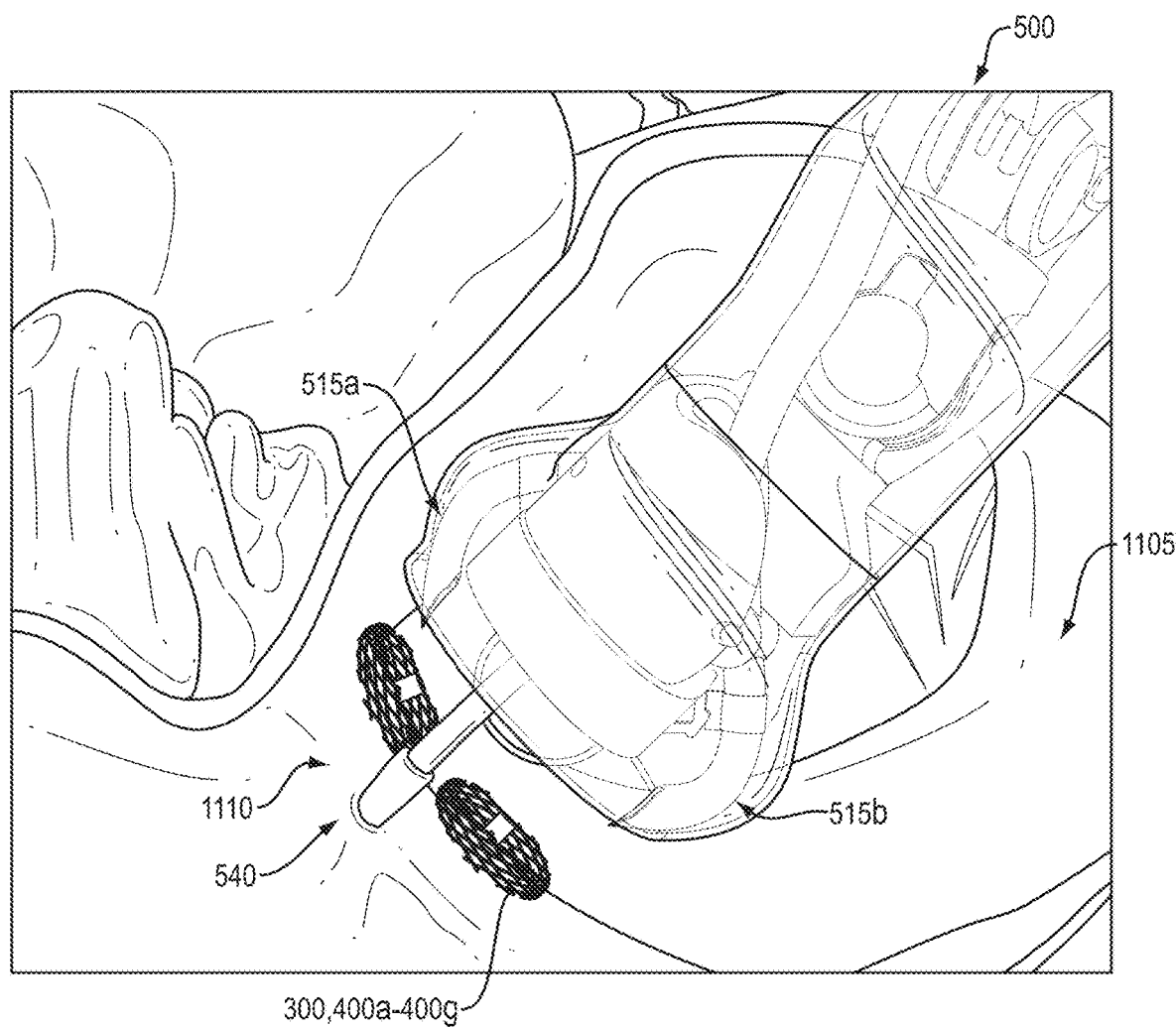
FIGS. 19A-19B illustrate an exemplary embodiment of an anchor delivery method of anchor placement in accordance with the present disclosure.
Figure 19B:
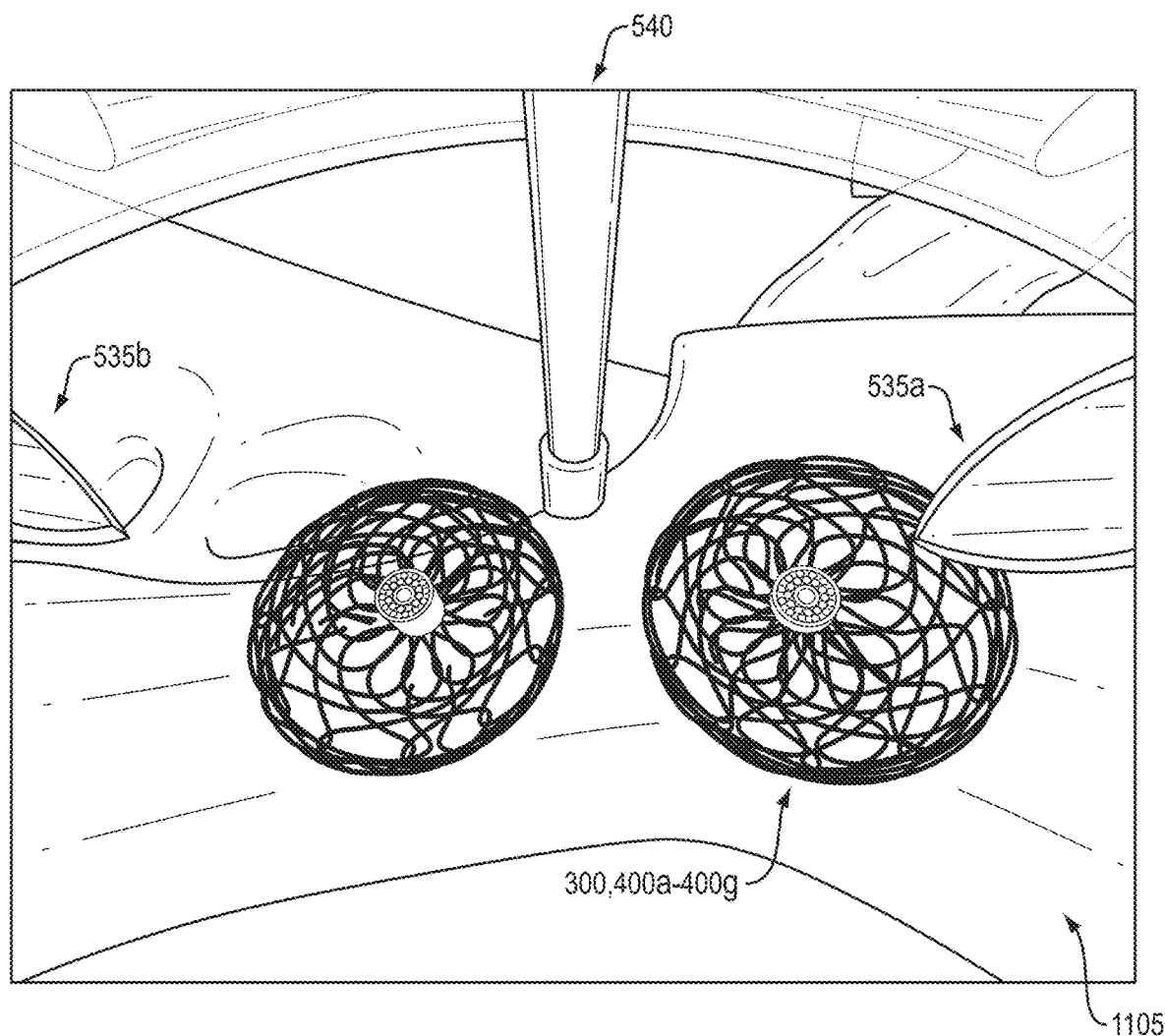

Referring back to the process described in FIG. 23, when the anchor 300, 400*a*-400*h* is positioned in the distal ends 535*a*, 535*b* of the first and second pincer arms 515*a*, 515*b*, the first and second pincer arms 515*a*, 515*b* may be rotated to an open position in step 2335 and shown in FIGS. 18A-18B. When the first and second pincer arms 515*a*, 515*b*, are actuated, rotated, to an open position, they are retracted from the tissue of the annulus 1110, with the anchor 300, 400*a*-400*h* being left in place in the annulus 1110. For example, the connector 305, 405 portion of the anchor 300, 400*a*-400*h* may be embedded in the annulus 1110. In some embodiments, the first and second pincer arms 515*a*, 515*b* may be rotatable from the tissue simultaneously or individually as an inner coil from an anchor delivery stylet is retracted to release the anchor from the stylet. Upon rotation of the first and second pincer arms 515*a*, 515*b*, the first and second disks 310*a*-310*b*, 410*a*-410*b*, 440*a*-440*b*, 445*a*-445*b*, 450*a*-450*b*, 465*a*-465*b* may be disposed on the annulus 1110 adjacent the valve 1105, and may be self-expandable in a radial direction upon rotation of the first and second pincer arms 515*a*, 515*b*, to the formed shapes described above and shown in FIG. 23A.

In alternate embodiments, e.g., instead of steps 2330 and 2335, at step 2332, when pincer arms 515*a*', 515*a*", 515*b*', 515*b*" are included in the delivery catheter 500, the anchor 300, 400*a*-400*h* may be towed through the first pincer arm 515*a*', 515*a*" and the second pincer arm 515*b*', 515*b*" while the distal ends 535*a*', 535*a*", 535*b*', 535*b*" are in a closed position. The anchor 300, 400*a*-400*h* may be towed through the first pincer arm 515*a*', 515*a*" (e.g., the pass-through needle) and the second pincer arm 515*b*', 515*b*" (side shooter passage), while the distal ends 535*a*', 535*a*", 535*b*', 535*b*" are in a closed position.

As shown in FIG. 17F, the anchor 300, 400*a*-400*h* may be positioned in a compressed state by an inner coil 489. The inner coil 489 may extend from the proximal end of the stylet 486 through the anchor 300, 400*a*-400*h* to be formed in a compressed state (see FIG. 17G). The stylet 486 may be extended through a working channel of the catheter, to the first pincer arm 515*a*', 515*a*". The anchor 300, 400*a*-400*h* may be pushed along the inner surface 517 of the first pincer arm 515*a*', 515*a*", and into the second pincer arm 515*b*', 515*b*". The anchor 300, 400*a*-400*h* may be pushed along the inner surface 519 of the second pincer arm 515*b*', 515*b*". Due to the open curvature 518 and the opening 518*a* of the surface of second pincer arm 515*b*', 515*b*", a distal end of the anchor 300, 400*a*-400*h* may extend through the tissue surface. As shown in FIG. 17A, when the first and second pincer arms 515*a*', 515*a*", 515*b*', 515*b*" are in a closed position after plicating the tissue, the anchor 300, 400*a*-400*h* may be pushed through the tissue so that a distal end extends out of the tissue, as indicated at reference numeral 1705, in a direction indicated by arrow 1710. The medical professional may visualize when a sufficient portion is extended out of the tissue, and then partially retract the inner coil 489 such that the bulb of the anchor 300, 400*a*-400*h* may expand (see FIG. 17B) at step 2334. For example, as shown in FIG. 17G, the inner coil 489 may be moved in a proximal direction, e.g., in a direction indicated by arrow 1715. The inner coil 489 may only be partially retracted from the anchor 300, 400*a*-400*h*, for example, an approximate amount indicated by reference numeral 1720, so that the first bulb or disk 310*a*-310*b*, 410*a*-410*b*, 440*a*-440*b*, 445*a*-445*b*, 450*a*-450*b*, or umbrella ends 465*a*-465*b*, of the anchor 300, 400*a*-400*h* may expand but the anchor is still connected to the stylet.

Figure 17H:
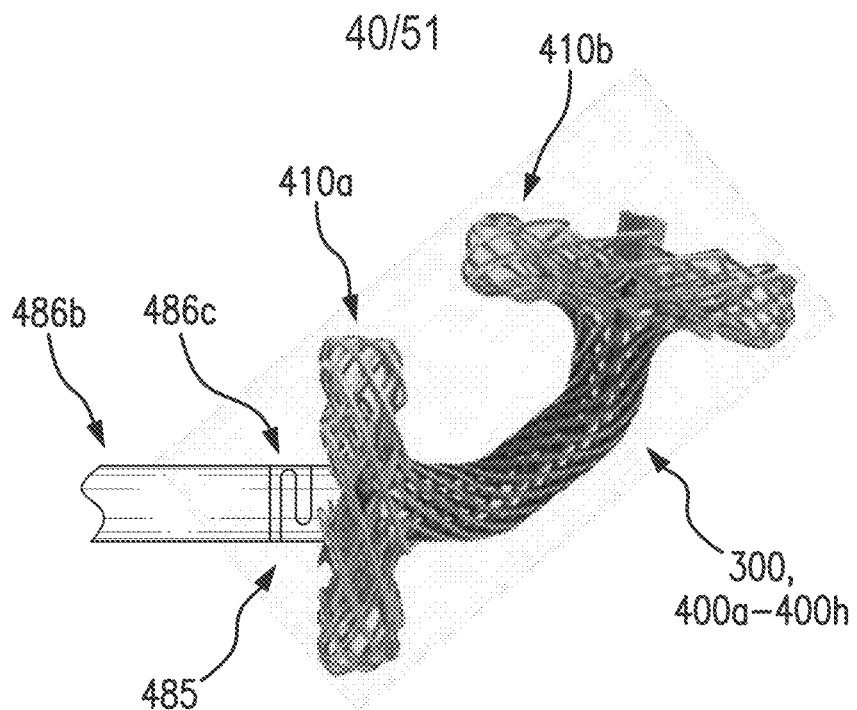

As shown in FIG. 17C, when the first bulb is in an expanded state, and the remaining portion of the anchor 300, 400*a*-400*h* is still in the compressed state held by the stylet 486, the second pincer arm 515*b*', 515*b*" may be rotated to an open position. The open curvature 518 of the second pincer arm 515*b*', 515*b*" may have a curved inner surface 519 so that when the second pincer arm 515*b*', 515*b*" is rotated open, the arm may not interfere with the anchor 300, 400*a*-400*h*. For example, the open curvature 518 may allow the arm to rotate, or retract, out of the tissue 1110 while leaving the partially deployed anchor undisturbed. For example, as shown in FIG. 17H, arrow 1725 indicates that an inner coil 489 has not yet been fully retracted, e.g., the inner coil 489 maintains a "locked" position of the anchor 300, 400a-400h to the stylet 486. It is understood that in some embodiments, the first pincer arm 515a', 515a" may still be in a closed position, e.g., plicating the tissue 1110, such that at least a portion of the stylet and/or the attached anchor are held in position in the tissue.

Figure 17I:
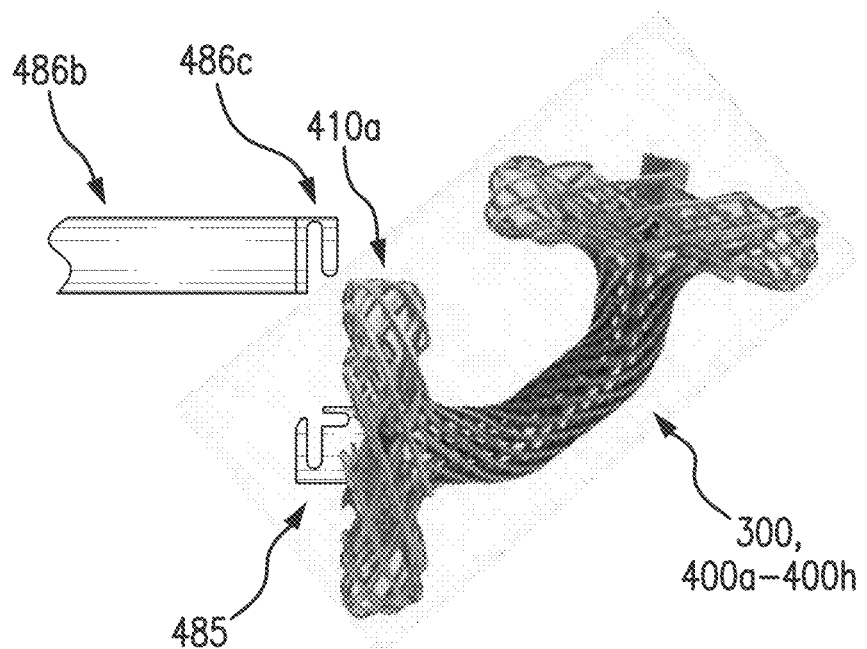

When the second pincer arm 515b', 515b" has been rotated out of the tissue, the first pincer arm 515a', 515a" may be rotated, or retracted, out of the tissue, as shown in FIG. 17D. The at least partially open tube 517 (e.g., the slide, or canoe-like shape) of the first pincer arm 515a', 515a" may allow the arm to rotate, or retract, out of the tissue without disturbing the anchor 300, 400a-400h. The anchor may be fully deployed by full retraction of the inner coil 489. For example, the inner coil 489 may be retracted in a proximal direction (e.g., as indicated by arrow 1715) so that the inner coil does not extend at all through the anchor 300, 400a-400h (e.g., the inner coil 489 is retracted to at least the distal tip 486c of the stylet 486). Retraction of the inner coil 489 at step 2336 may allow the anchor 300, 400a-400h to fully expand, so that a second bulb is formed on the tissue. Full retraction of the inner coil 489 may also allow the anchor 300, 400a-400h to "unlock" from the stylet 486, and the connector 485 may disengage from the distal tip 486c of the stylet 486, as shown in FIG. 17I. For example, arrow 1730 may indicate that the inner coil 489 has been fully retracted proximally into the stylet 486, such that the anchor 300, 400a-400h may "unlock" from the stylet 486. The stylet 486 may be fully retracted in a proximal direction out of the distal end 510 of the delivery catheter 500, leaving the deployed anchor in the annulus 1110.

For the various embodiments of deployment, when the anchor 300, 400a-400h is properly inserted, the first and second disk 310a-310b, 410a-410b, 440a-440b, 445a-445b, 450a-450b, 465a-465b may lie against the annulus 1110 facing the valve 1105. For example, first inward surface 475a of the first disk 410a and second inward surface 475b of the second disk 410b may contact a surface of the annulus 1110. The anchor 400f shown in FIG. 4F having the reverse concave ends 465a, 465b, a first and second bottom portion 480a, 480b may contact the annulus 1110. A portion of the annulus 1110 may therefore be pinched between the anchor disks to create a plication or fold, reducing the perimeter of the valve. By creating plications and holding them in place via the anchors 300, 400a-400h, annular tissue around the valve may be tightened or reduced by forces between the annulus 1110 and the anchor 300, 400a-400h, allowing the valve to fully close or close more fully. The anchor 300, 400a-400h may hold the annulus in position so that the mitral and/or tricuspid valve may fully close or close more fully, thereby repairing or significantly improving the function of the valve. The various anchor sizes and variations described herein allow for customization to the particular patient and valve defect. For example, a larger valve defect may require greater forces acting between the annulus 1110 and the anchor 300, 400a-400h, and therefore an anchor having a larger disk diameter may be necessary. In contrast, a smaller defect may necessitate a smaller disk diameter. By customizing the particular anchor to the patient and defect, the delivery catheter 500 according to the present disclosure overcomes disadvantage of annulus tearing and subsequent replacement of the one-size-fits-all annuloplasty rings and bands.

Figure 20A:
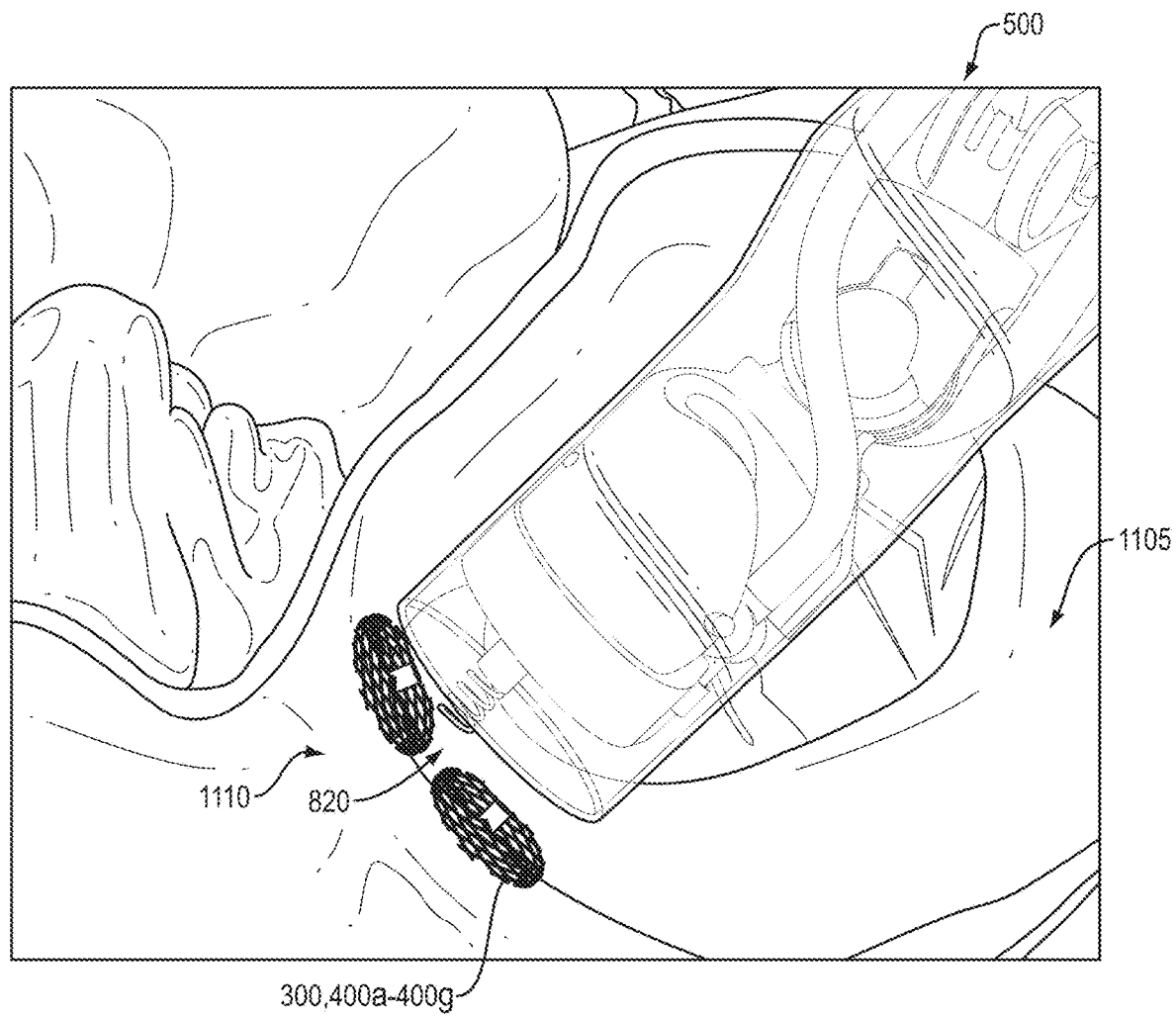
FIGS. 20A-20B illustrate an exemplary embodiment of an anchor delivery method of disengaging the anchor delivery catheter in accordance with the present disclosure.
Figure 20B:
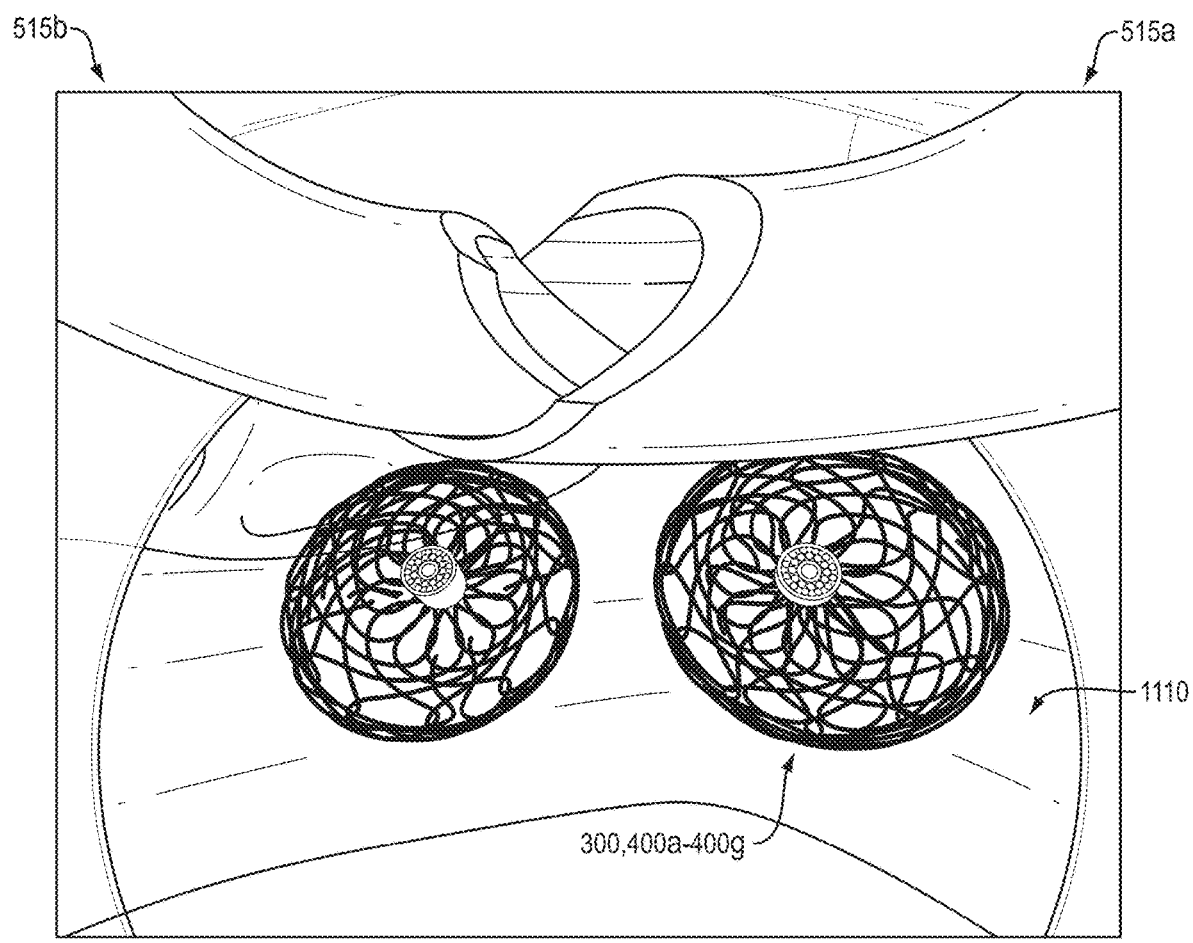

At step 2340 and shown in FIGS. 20A-20B, the delivery catheter 500 may be disengaged from the annulus by translating the delivery catheter 500 in a direction away from the annulus 1110 so that the first and second pincer arms 515a, 515a', 515a", 515b, 515b', 515b" may be rotatable to a closed position without piercing the annulus 1110 or otherwise interfering with the inserted anchor 300, 400a-400h. Additionally, the helical anchor 820 may be rotated to withdraw from the annulus 1110, and the helical stabilizer 540 may be retracted in a direction away from the annulus 1110 to avoid interference with the inserted anchor 300, 400a-400h.

Figure 21A:
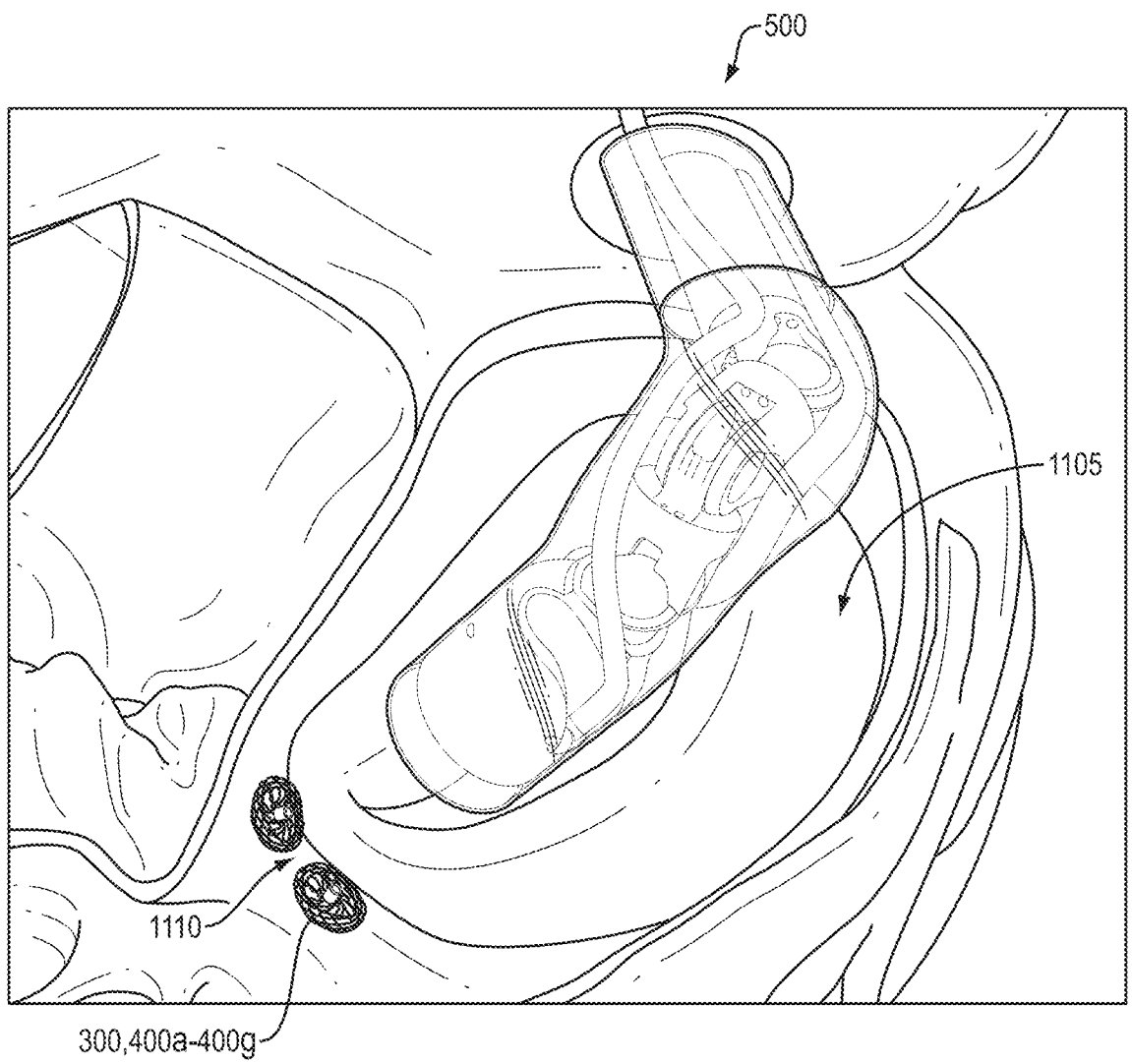
FIGS. 21A-21B illustrate an exemplary embodiment of an anchor delivery method of inspecting anchor placement in accordance with the present disclosure.
Figure 21B:
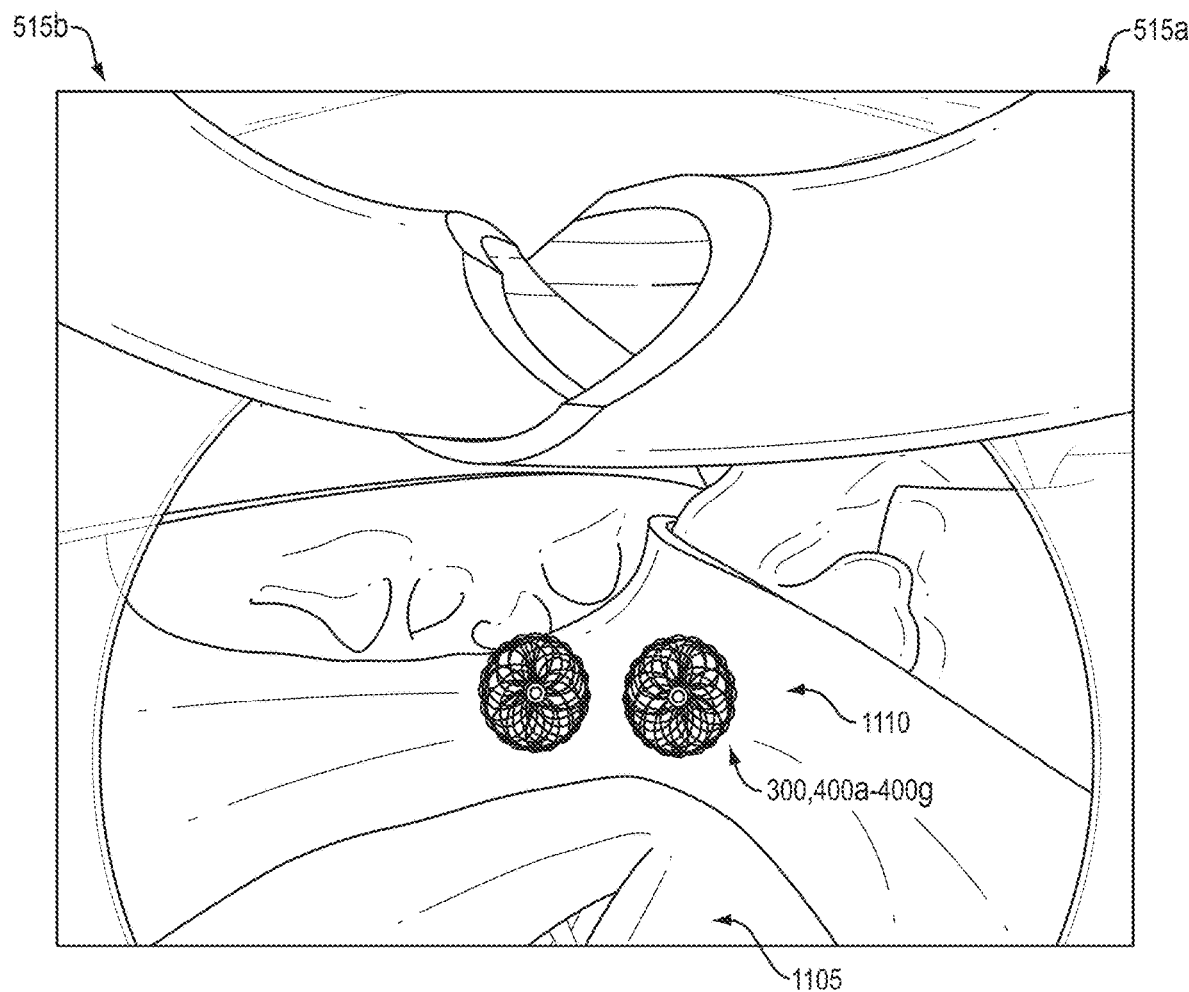

At step 2345 and shown in FIGS. 21A-21B, the delivery catheter 500 may be further translated in a direction away from the annulus 1110 and the valve 1105 so that the user may inspect the anchor 300, 400a-400h. The camera 545, light 550, and/or sensors 555, 565 may assist the user in visually inspecting placement with respect to the valve 1105, and to verify accuracy of the disk placement.

If the inspection determines that additional anchors are needed at step 2350, steps 2310 through 2345 may be repeated to insert a plurality of anchors 300, 400a-400h around the valve 1105 and surrounding annulus 1110, placing anchors at least partially around the valve 1105 as shown in FIGS. 22A-22B. It is understood that any number "n" of anchors may be delivered and deployed in the patient. In some embodiments, anchors may only be needed at a portion of the bicuspid and/or tricuspid valve to support closure, whereas in other embodiments a plurality of anchors fully around the valve may be necessary for closure. Anchors may be insertable in any order around the valve 1105, e.g., a medical professional may insert anchors in an order around the valve 1105 according to their own preference. When the inspection at step 2345 indicates that additional anchors are not needed at step 2350, the process ends at step 2355. In some embodiments, anchors may not be placed fully around the valve 1105, e.g., no anchors may be inserted in the annulus around the anterior leaflet, because tissue is fibrous and is adjacent to the aortic valve.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An anchor delivery system for repairing a valve in a body of a patient, the anchor delivery system comprising:
   a delivery catheter having a distal end with two or more rotatably coupled knuckles, wherein an axis of rotation of a first knuckle is substantially perpendicular to an axis of rotation of a second knuckle such that the two or more knuckles form an articulable distal end of the delivery catheter; and
   an anchor delivery mechanism disposed distally of the two or more knuckles, the anchor delivery mechanism including:
      a first pincer arm having a distal end and a proximal end rotatably coupled with respect to the delivery catheter;
      a second pincer arm having a distal end and a proximal end rotatably coupled with respect to the delivery catheter; and
      an anchor having a first end expandable from a compressed configuration to an expanded configuration, and a second end expandable from a compressed configuration to an expanded configuration;
   wherein:
   in a closed position, the distal ends of the first and second pincer arms are positioned together to deliver the anchor, extending between the proximal ends of the pincer arms with the first and second ends in respective compressed configurations, to the valve; and
   in an open position, the distal ends of the first and second pincer arms are rotated apart from each other to release the anchor with each of the first and second ends of the anchor in a respective expanded configuration lying against the valve.

2. The anchor delivery system according to claim 1, wherein the distal end of the anchor delivery mechanism includes at least one of:
   a five degree-of-freedom (DOF) navigation sensor;
   a six DOF navigation sensor;
   a camera;
   a light; and
   an ultrasonic sensor.

3. The anchor delivery system according to claim 1, wherein the distal end of the anchor delivery mechanism includes a weeping balloon capable of delivering saline.

4. The anchor delivery system according to claim 1, further comprising a fixation device disposed at the distal end of the anchor delivery mechanism, and insertable into tissue to anchor the delivery catheter to the tissue.

5. The anchor delivery system according to claim 1, further comprising a plurality of cables extending from a proximal end of the delivery catheter to the two or more knuckles, to control flexing of the knuckles.

6. An anchor delivery system for repairing a heart valve, the anchor delivery system comprising:
   an anchor delivery mechanism disposed at a distal end of a delivery catheter, the anchor delivery mechanism including:
      a first pincer arm having a distal end and a proximal end rotatably coupled with respect to the delivery catheter;
      a second pincer arm having a distal end and a proximal end rotatably coupled with respect to the delivery catheter; and
      an anchor having a first end expandable from a compressed configuration to an expanded configuration, and a second end expandable from a compressed configuration to an expanded configuration;
   wherein:
   in a closed position, the distal ends of the first and second pincer arms are positioned together to deliver the anchor, extending between the proximal ends of the pincer arms with the first and second ends in respective compressed configurations, to the valve; and
   in an open position, the distal ends of the first and second pincer arms are rotated apart from each other to release the anchor with each of the first and second ends of the anchor in a respective expanded configuration lying against the valve.

7. The anchor delivery system according to claim 6, further comprising more than one anchor deliverable to tissue of a valve by the first and second pincer arms.

8. The anchor delivery system according to claim 6, wherein the first and second pincer arms are configured to pierce the tissue by the distal ends of the first and second pincer arms to the closed position, and are further configured such that the anchor is deliverable through the first pincer arm and the second pincer arm.

9. The anchor delivery system according to claim 8, wherein the first and second pincers arms are retractable to the open position such that the anchor remains in the tissue, the anchor being configured to reduce a perimeter of the valve.

10. The anchor delivery system according to claim 6, wherein the first pincer arm is formed of an at least partially open tube and the second pincer arm has an open curvature, such that the anchor is towable through the first and second pincer arms.

11. The anchor delivery system according to claim 6, wherein the distal ends of the first and second pincer arms are configured to pierce a tissue of the heart valve.

12. The anchor delivery system according to claim 11, wherein the anchor is deliverable to the distal ends of the first and second pincer arms when the first and second pincer arms are in the closed position.

13. The anchor delivery system according to claim 12, wherein the first and second pincers arms are retractable to the open position such that the anchor remains in the tissue, the anchor being configured to reduce a perimeter of the heart valve.

14. A method for delivering an anchor by an anchor delivery system for repairing a valve in a body of a patient, the method comprising:
   inspecting tissue of the valve by a distal end of a delivery catheter, the distal end of the delivery catheter being comprised of two or more rotatably coupled knuckles;
   opening first and second pincer arms of an anchor delivery mechanism disposed distally of the two or more knuckles, the first pincer arm rotatably coupled with respect to the delivery catheter, and the second pincer arm rotatably coupled with respect to the delivery catheter;

rotating the first and second pincer arms into a closed position to pierce the tissue and position distal ends of the first and second pincer arms together toward a center of the anchor delivery mechanism;

delivering a first anchor, having a first end expandable from a compressed configuration to an expanded configuration and a second end expandable from a compressed configuration to an expanded configuration, to the first and second pincer arms with the first and second ends in respective compressed configurations;

rotatably opening the first and second pincer arms to retract from the tissue, the delivered first anchor remaining in the tissue with each of the first end and the second end thereof in a respective expanded configuration lying against the tissue; and inserting additional anchors around the tissue as necessary to repair the valve.

15. The method according to claim 14, wherein upon opening the first and second pincer arms for piercing the tissue, the delivery catheter is translatable such that the first and second pincer arms pierce into the tissue at a repeatable tissue depth.

16. The method according to claim 14, wherein the first anchor is delivered by towing the first anchor by a stylet through the first and second pincer arms such that a portion of the first anchor extends out of the tissue.

17. The method according to claim 16, further comprising:

retracting an inner coil extended through the stylet and the first anchor;

rotating the second pincer arm out of the tissue;

retracting the inner coil from a remaining portion of the first anchor to plicate the tissue; and rotating the first pincer arm out of the tissue.

18. The method according to claim 14, wherein the first pincer arm is formed of an at least partially open tube and the second pincer arm has an open curvature, such that the first anchor is towable through the first and second pincer arms.

19. The method according to claim 14, further comprising inserting a fixation device in the tissue to anchor the delivery catheter before delivering the first anchor, and disengaging the delivery catheter from the tissue by retracting the fixation device after delivering the first anchor.

20. The method according to claim 14, wherein: the delivery catheter further comprises a plurality of cables; each cable of the plurality of cables is connected at a distal end to a respective knuckle of the two or more rotatably coupled knuckles, and operable by a motor connected at a proximal end of the cables; and the distal end of the delivery catheter is movable by flexing joints between the knuckles of the two or more rotatably couped knuckles, and minimizing tension on the respectively connected cable.

* * * * *